(12) United States Patent
Moore et al.

(10) Patent No.: US 11,396,496 B2
(45) Date of Patent: Jul. 26, 2022

(54) 1,4-SUBSTITUTED ISOQUINOLINE INHIBITORS OF KEAP1/NRF2 PROTEIN-PROTEIN INTERACTION

(71) Applicant: THE BOARD OF TRUSTEES OF THE UNIVERSITY OF ILLINOIS, Urbana, IL (US)

(72) Inventors: Terry Moore, Chicago, IL (US); Phillip Lazzara, Chicago, IL (US); Brian David, Chicago, IL (US); Benjamin Richardson, West Palm Beach, FL (US); Atul D. Jain, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 17/044,554

(22) PCT Filed: Apr. 2, 2019

(86) PCT No.: PCT/US2019/025464
§ 371 (c)(1),
(2) Date: Oct. 1, 2020

(87) PCT Pub. No.: WO2019/195348
PCT Pub. Date: Oct. 10, 2019

(65) Prior Publication Data
US 2021/0017135 A1 Jan. 21, 2021

Related U.S. Application Data

(60) Provisional application No. 62/653,650, filed on Apr. 6, 2018.

(51) Int. Cl.
*C07D 217/22* (2006.01)

(52) U.S. Cl.
CPC .................... *C07D 217/22* (2013.01)

(58) Field of Classification Search
CPC .................................................. C07D 217/22
See application file for complete search history.

(56) References Cited

U.S. PATENT DOCUMENTS 5,416,094 A 5/1995 Lal et al.

FOREIGN PATENT DOCUMENTS

EP 2998292 A1 3/2016

OTHER PUBLICATIONS

Richardson, J Med Chem, 2018, vol. 61, 8029-8047. (Year: 2018).*
Keleku-Lukwete, Antioxidants & Redox Signaling, vol. 29(17), 2018, 1746-1755. (Year: 2018).*
Jaramillo, Gene & Development, vol. 27, 2179-2191, 2021. (Year: 2021).*
Cuadrado, Nature Reviews: Drug Discovery, vol. 18, Apr. 2019, 295-317. (Year: 2019).*
Salim, J Org Chem, vol. 85, 1416-1424, 2020. (Year: 2020).*
Lee, Med Chem Research, vol. 29, 846-867, 2020. (Year: 2020).*
Apelqvist et al., Diabetes/metabolism research and reviews, Suppl 1:S75-S83 (2000).
Barrientos et al., official publication of the wound healing society [and] the european tissue repair society, 16(5):585-601 (2008).
Bennett et al., Growth factors in the treatment of diabetic foot ulcers, Br. J. Surg., 90(2):133-146 (2003).
Beyer et al., Roles and mechanisms of action of the Nrf2 transcription factor in skin morphogenesis, wound repair and skin cancer, Cell Death Differ., 14(7):1250-1254 (2007).
Bitar et al., A defect in Nrf2 signaling constitutes a mechanism for cellular stress hypersensitivity in a genetic rat model of type 2 diabetes, Am. J. Physiol. Endocrinol. Metab., 301(6):E1119-E1129 (2011).
Bitar et al., The GSK-3β/Fyn/Nrf2 pathway in fibroblasts and wounds of type 2 diabetes: On the road to an evidence-based therapy of non-healing wounds, Adipocyte, 1(3):161-163 (2012).
Braun et al., Nrf2 transcription factor, a novel target of keratinocyte growth factor action which regulates gene expression and inflammation in the healing skin wound, Mol. Cell. Biol., 22(15):5492-5505 (2002).
Cuadrado et al., Therapeutic targeting of the NRF2 and KEAP1 partnership in chronic diseases, Nat. Rev. Drug Discov., 18(4):295-317 (2019).

(Continued)

*Primary Examiner* — D Margaret M Seaman
(74) *Attorney, Agent, or Firm* — Marshall, Gerstein & Borun LLP

(57) ABSTRACT

Disclosed herein are compounds that can act as inhibitors of the Kelch-like ECH-associated protein 1/nuclear factor (erythroid-derived 2)-like 2 ("KEAP1/NRF2") protein-protein interaction, and methods of using the compounds to treat and prevent diseases and disorders, such as COPD, multiple sclerosis, and diabetes, and in the promotion of wound healing. The compounds described herein can include compounds of Formula (I) and pharmaceutically acceptable salts thereof: formula (I), wherein the substituents are as described.

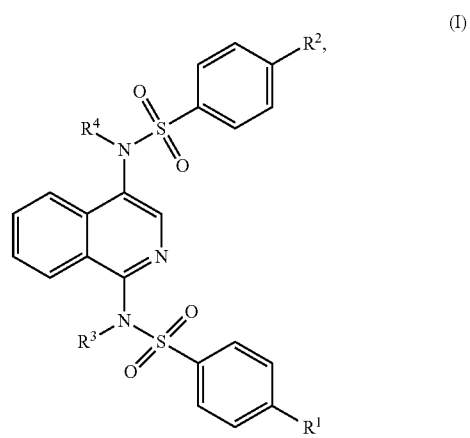

15 Claims, 2 Drawing Sheets

(56) References Cited

OTHER PUBLICATIONS

Daeschlein et al., Antimicrobial and antiseptic strategies in wound management, Int. Wound J., Suppl 1:9-14 (2013).
Dandona et al., Inflammation: the link between insulin resistance, obesity and diabetes, Trends immunol., 25(1):4-7 (2004).
Dissemond et al., Modern wound care—practical aspects of non-Interventional topical treatment of patients with chronic wounds, J. Dtsch. Dermatol. Ges., 12(7):541-554 (2014).
Dong et al., Effect of ibuprofen on the inflammatory response to surgical wounds, J. Trauma., 35(3):340-343 (1993).
Dvivedi et al., Effect of ibuprofen and diclofenac sodium on experimental would healing, Indian J. Exp. Biol., 35(11): 1243-1245 (1997).
Edwards et al., Debridement of diabetic foot ulcers, Cochrane Database Syst. Rev., 2010(1):CD003556 (2010).
Ennis et al., Ultrasound therapy for recalcitrant diabetic foot ulcers: resultsofa randomized, double-blind, controlled, multicenter study, Ostomy Wound Manage., 51(8):24-39 (2005).
Franz et al., Optimizing healing of the acute wound by minimizing complications, Curr. Probl. Surg., 44(11):691-763 (2007).
Futagami et a., Wound healing involves induction of cyclooxygenase-2 expression in rat skin, Lab. Invest., 82(11):1503-1513 (2002).
Gonzalez-Chavez et al., Pathophysiological implications between chronic inflammation and the development of diabetes and obesity, Cir. Cir., 79(2):209-216 (2011).
Gosain et al., Aging and wound healing, World J. Surg., 28(3):321-326 (2004).
Guo et al., Factors affecting wound healing, J. Dent Res., 89(3):219-229 (2010).
Hofman et al., Use of topical corticosteroids on chronic leg ulcers, J. Wound Care., 16(5):227-230 (2007).
Inoyama et al., Optimization of fluorescently labeled Nrf2 peptide probes and the development of a fluorescence polarization assay for the discovery of inhibitors of Keap1-Nrf2 interaction, J. Biomol. Screen., 17:435-447 (2012).
International Application No. PCT/US2019/025464, International Search Report and Written Opinion, dated May 29, 2019.
Jones et al., Inhibition of angiogenesis by nonsteroidal anti-inflammatory drugs: insight into mechanisms and implications for cancer growth and ulcer healing, Nat. Med., 5(12):1418-1423 (1999).
Khanna et al., Macrophage dysfunction impairs resolution of inflammation in the wounds of diabetic mice, PLoS ONE, 6(3):e9539 (2010).
Kramer et al., Suitability of tissue tolerable plasmas (TTP) for the management of chronic wounds, Clin. Plasma Med., 1(1):11-18(2013).
Lantis et a., Analysis of patient cost for recombinant human platelet-derived growth factor therapy as the first-line treatment of the insured patient with a diabetic foot ulcer, Adv. Skin Wound Care., 22(4):167-171 (2009).
Lazarus et al., Definitions and guidelines for assessment of wounds and evaluation of healing, Wound Repair Regen, 2(3):165-170 (1994).
Lebrun et al., The role of surgical debridement in healing of diabetic foot ulcers, Wound Repair Regen, 18(5):433-438 (2010).
Lee et al., Increased protein oxidation and decreased expression of nuclear factor E2-related factor 2 protein in skin tissue of patients with diabetes, Clin. Exp. Dermatol., 40(2):192-200 (2015).
Long et al., An essential role of NRF2 in diabetic wound healing, Diabetes, 65(3):780-793 (2016).
Menke et al., Impaired wound healing, Clin. Dermatol., 25(1):19-25 (2007).
Mosser et al., Exploring the full spectrum of macrophage activation, Nat. Rev. Immunol., 8(12):958-969 (2008).
Moura et al., Recent advances on the development of wound dressings for diabetic foot ulcer treatment—a review, Acta Biomater., 9(7):7093-114 (2013).
Pubchem, Substance Record for SID 318395779, Available Date: Oct. 26, 2016, [retrieved on May 10, 2019], Retrieved from the Internet: <https://pubchem.ncbi.nlm.nih.gov/substance/318395779>.
Raffetto et al., Phlebology venous forum of the royal society of medicine, 29(1 suppl):157-164 (2014).
Richardson et al., Replacement of a Naphthalene Scaffold in Kelch-like ECH-Associated Protein 1 (KEAP1)/Nuclear Factor (Erythroid-derived 2)-like 2 (NRF2) Inhibitors, J. med. Chem., 61(17):8029-8047 (2018).
Rosner et al., Immunohistochemical characterization of the cutaneous cellular infiltrate in different areas of chronic leg ulcers, APMIS., 103(4):293-299 (1995).
Schmidt et al., Non-thermal plasma activates human keratinocytes by stimulation of antioxidant and phase II pathways, J. Biol. Chem., 290(11):6731-6750 (2015).
Sen et al., Human skin wounds: A major and snowballing threat to public health and the economy, Wound Repair Regen, 17(6):763-771 (2009).
Tallis et al., Clinical and economic assessment of diabetic foot ulcer debridement with collagenase: results of a randomized controlled study, Clin. Ther., 35(11):1805-1820 (2013).
Wellen et al., Inflammation, stress, and diabetes, J. Clin. Invest., 115(5):1111-1119 (2005).
Wollina et al., Effects of low-frequency ultrasound on microcirculation in venous leg ulcere, Indian J. Dermatol., 56(2):174-179 (2011).
Cuadrado et al., Transcription factor NRF2 as a therapeutic target for chronic diseases: a systems medicine approach, Pharm. Rev., 70(2):348-83 (Apr. 2018).
Sun et al., Recent progress in the development of small molecule Nrf2 modulators: a patent review (2012-2016), Exp. Opin. Therap. Patents, 27(7):763-85 (May 2017).
European Patent Application No. 19781449.4, Extended European Search Report, dated Dec. 3, 2021.

* cited by examiner

1,4-SUBSTITUTED ISOQUINOLINE INHIBITORS OF KEAP1/NRF2 PROTEIN-PROTEIN INTERACTION

CROSS REFERENCE TO RELATED APPLICATION

This application is the U.S. national phase of International Application No. PCT/US2019/025464, filed Apr. 2, 2019, which claims priority to U.S. Provisional Patent Application No. 63/653,650, filed Apr. 6, 2018, the disclosure of which is hereby incorporated by reference in its entirety.

STATEMENT OF GOVERNMENT SUPPORT

This invention was made with government support under R01 AR069541 awarded by the National Institutes of Health. The government has certain rights in the invention.

BACKGROUND

Field of the Invention

The present disclosure relates to compounds that can act as inhibitors of the Kelch-like ECH-associated protein 1/nuclear factor (erythroid-derived 2)-like 2 ("KEAP1/NRF2") protein-protein interaction, and methods of using the compounds to treat and prevent diseases and disorders, such as COPD, multiple sclerosis, and diabetes, and to accelerate wound healing.

Description of Related Technology

Chronic oxidative stress is implicated as a major factor in a number of disease states such as chronic obstructive pulmonary disease ("COPD"), multiple sclerosis, diabetic chronic wounds, and chronic kidney disease. Thus, upregulating cellular defenses against oxidative stress can be a viable pathway for treatment or management of such diseases. Nuclear factor (erythroid-derived 2)-like 2 ("NRF2"), a basic leucine zipper protein ("bZIP"), regulates cellular expression of antioxidant proteins. This oxidative stress response is gated primarily by Kelch-like ECH-associated protein 1 ("KEAP1"), which sequesters NRF2 and assists in poly-ubiquinating it, tagging it for proteosomal degradation. If the KEAP1-NRF2 protein-protein interaction is inhibited, NRF2 can no longer be sequestered and tagged for degradation, which allows NRF2 to translocate into the nucleus where it promotes the transcription of antioxidant response elements such as NQO1, heme oxygenase ("HO1"), and glutathione S-transferase.

In the absence of pharmaceutical intervention, the KEAP1-NRF2 interaction is inhibited in the presence of electrophiles, reactive oxygen, or nitrogen species, which leads to a cytoprotective response in the cell. Current therapies which inhibit the KEAP1-NRF2 interaction utilize KEAP1's sensitivity to electrophiles to upregulate cellular NRF2 levels. This approach can be problematic as potent electrophiles are traditionally seen as promiscuous in vivo and their lack of specificity may obscure their true mechanism of action. For example, the beneficial effects of dimethyl fumarate (TECFIDERA) in the treatment of multiple sclerosis was originally thought to be derived from inhibition of the KEAP1-NRF2 interaction. It is currently believed, however, to be operating through many biological pathways to generate its therapeutic effect.

To accurately understand the role NRF2 plays in the treatment of chronic inflammatory conditions, selective non-electrophilic inhibitors of the KEAP1-NRF2 interaction have been developed. Non-electrophilic inhibitors of the KEAP1-NRF2 protein-protein interaction typically focus on targeting the KELCH-domain of KEAP1 to inhibit the adoption of a KEAP1-NRF2 complex capable of NRF2 ubiquitination. It has been previously reported that 1,4-substituted naphthalene compounds can act as NRF2 activators with low nanomolar potencies in vitro, and can increase transcription of NRF2 target genes in cells. It has been found, however, that these compounds suffer from poor solubility and/or poor metabolic stability, and also exhibit mutagenic properties.

Accordingly, there is a need for inhibitors of the KEAP1-NRF2 interaction that have high binding affinity and a more favorable solubility and metabolic profile than the traditional inhibitors.

SUMMARY

In one aspect, the disclosure provides compounds of Formula (I), or pharmaceutically acceptable salts thereof:

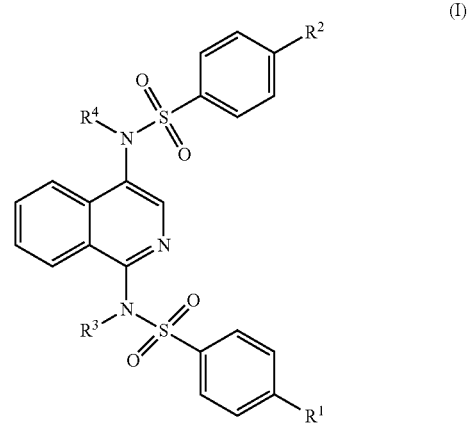

wherein
each of $R^1$ and $R^2$ independently is halo, OH, CN, $C_{1-6}$haloalkyl, $C_{1-6}$alkoxy, $C_{1-6}$haloalkoxy, or $C(O)R^6$;
each of $R^3$ and $R^4$ independently is H, $C_{1-6}$alkyl, deuterated $C_{1-6}$alkyl, $C_{1-6}$haloalkyl, $C_{1-6}$ alkylene-CN, $C_{0-6}$alkylene-$C_{1-6}$heteroaryl having 1, 2, 3, or 4 heteroatoms selected from N, O, and S, $C_{0-6}$alkylene-C(O)$R^6$, $C_{0-6}$alkylene-N($R^5$)SO$_2R^7$, $C_{0-6}$alkylene-C(O)N($R^5$)SO$_2R^7$, $C_{0-6}$alkylene-C(O)NHOH, or $C_{0-6}$alkylene-C=N(OH)N($R^5$)$_2$;
each $R^5$ independently is H or $C_{1-6}$alkyl;
$R^6$ is OH, $C_{1-6}$haloalkyl, or $C_{1-6}$alkoxy; and
$R^7$ is $C_{1-6}$alkyl or N($R^5$)$_2$.

In some embodiments, each of $R^1$ and $R^2$ independently is Cl, F, $C_{1-3}$haloalkyl, $C_{1-3}$alkoxy, $C_{1-3}$haloalkoxy, or C(O)$C_{1-3}$alkoxy. In various embodiments, each of $R^1$ and $R^2$ independently is OCH$_3$, F, Cl, CN, CF$_3$, OCF$_3$, or C(O)CF$_3$. In some cases, each of $R^1$ and $R^2$ independently is OCH$_3$ or F. In various cases, $R^3$ is $C_{0-6}$alkylene-COOH, $C_{0-6}$alkylene-C(O)C$_{1-6}$alkoxy, $C_{0-6}$alkylene-C$_{1-5}$heteroaryl having 1, 2, 3, or 4 heteroatoms selected from N, O, and S, $C_{0-6}$alkylene-N($R^5$)SO$_2R^7$, $C_{0-6}$alkylene-C(O)N($R^5$)SO$_2R^7$, $C_{0-6}$alkylene-C(O)NHOH, or $C_{0-6}$alkylene-C=N(OH)N($R^5$)$_2$;

each $R^5$ independently is H or $C_{1-6}$alkyl; and $R^7$ is $C_{1-6}$alkyl or $N(R^5)_2$. In some embodiments, $R^3$ is $CH_2COOH$, $CH(CH_3)COOH$,

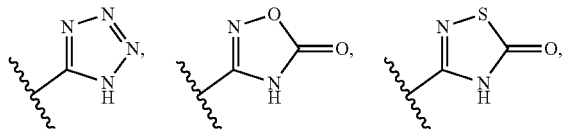

$CH_2C(O)NHOH$, $CH_2C(O)NHSO_2CH_3$, $CH_2C(O)NHSO_2N(CH_3)_2$, $CH_2CH_2NHSO_2CH_3$, $CH_2CH_2NHSO_2N(CH_3)_2$, or $CH_2C=N(OH)NH_2$. In various embodiments, $R^3$ is $CH_2COOH$. In some cases, $R^4$ is H, $C_{1-6}$haloalkyl, $C_{1-6}$alkylene-CN, or $C_{0-6}$alkylene-C(O)$C_{1-6}$haloalkyl. In various cases, $R^4$ is H, $CF_3$, $CH_2CF_3$, $CF_2CH_3$, $CH_2CF_2H$, $CH_2CFH_2$, $CH_2CH_2CF_3$, $CH_2CN$, or $CH_2C(O)CF_3$. In some embodiments, $R^4$ is $CH_2CF_3$. Specifically contemplated compounds of the disclosure include the compounds listed in Table A or pharmaceutically acceptable salts thereof. Specifically contemplated compounds of the disclosure include the compounds listed in Table B or pharmaceutically acceptable salts thereof. In some embodiments, the disclosure provides a compound having a structure selected from the group consisting of:

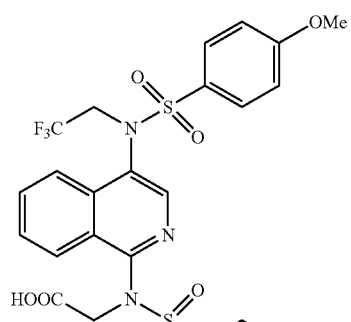

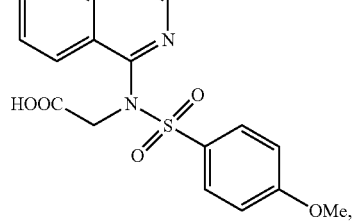

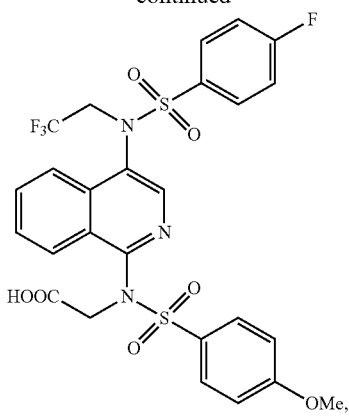

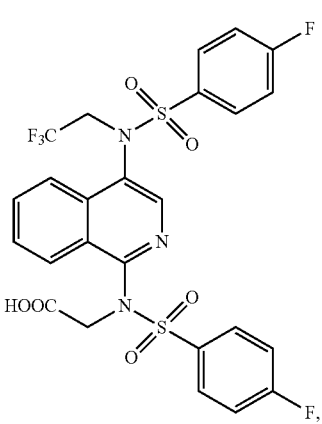

and

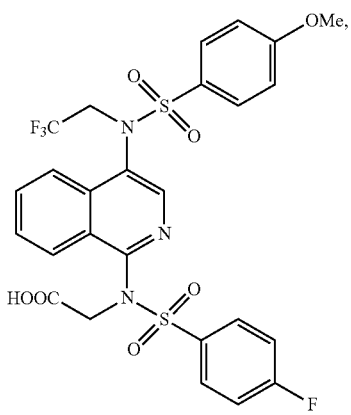

or pharmaceutically acceptable salts thereof. In various embodiments, the compound of Formula (I) is has a structure

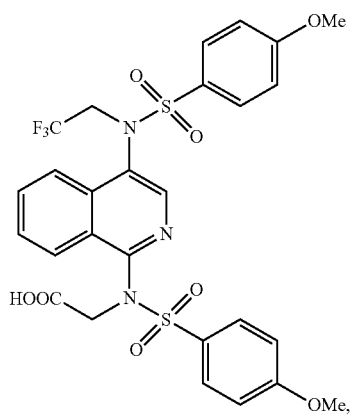

or a pharmaceutically acceptable salt thereof.

Another aspect of the disclosure provides a pharmaceutical composition comprising a compound or salt described herein and a pharmaceutically acceptable carrier.

Yet another aspect of the disclosure provides a method of inhibiting the KEAP-1/NRF2 interaction in a cell comprising contacting the cell with a compound or salt described herein, or the pharmaceutical composition described herein, in an amount effective to inhibit the KEAP-1/NRF2 interaction.

Still another aspect of the disclosure provides a method of treating a clinical or preclinical disease or disorder associated with dysregulation of the KEAP1-NRF2 interaction comprising administering to a subject in need thereof a therapeutically effective amount of a compound or salt described herein, or the pharmaceutical composition described herein. In some embodiments, the clinical disease or disorder is selected from the group consisting of Alport syndrome, amyotrophic lateral sclerosis, autosomal dominant polycystic kidney disease, bone disease, blood disease, chronic kidney disease, chronic obstructive pulmonary disease, connective tissue disease, dry eye macular degeneration, estrogen receptor-positive breast cancer, eye disease, focal segmental glomerulosclerosis, Friedreich ataxia, immunoglobulin A nephropathy, interstitial lung disease, lung diseases, multiple sclerosis, kidney disease, neurodegenerative disease, primary focal segmental glomerulosclerosis, psoriasis, pulmonary arterial hypertension, retinovascular disease, subarachnoid hemorrhage, type 1 diabetes, and type 2 diabetes mellitus. In various embodiments, the preclinical disease or disorder is selected from the group consisting of, autoimmune diseases (e.g., rheumatoid arthritis, Sjogren syndrome, STING-dependent interferonopathies, systemic lupus erythematous, vitiligo); respiratory diseases (e.g., chronic obstructive pulmonary disease, chronic sarcoidosis, emphysema, hypersensitivity pneumonitis, idiopathic pulmonary fibrosis, pulmonary fibrosis); gastrointestinal diseases (e.g., hemochromatosis, hepatic fibrosis, primary biliary cholangitis and cirrhosis); metabolic diseases (e.g., insulin resistance, glomerulonephritis, nonalcoholic steatohepatitis, type 2 diabetes melliltus, vascular dysfunction); cardiovascular diseases (e.g., atherosclerosis, diabetic vascular disease, hypertension, myocardial ischemia-reperfusion injury, heart failure); neurodegenerative diseases (e.g., Alzheimer disease, Huntington disease, Friedrich ataxia, Parkinson disease); skin diseases (e.g., chronic/diabetic wound healing); and cancer chemoprevention.

Another aspect of the disclosure provides a method of accelerating healing of a wound comprising administering to a subject in need thereof a therapeutically effective amount of the compound or salt described herein or the pharmaceutical composition described herein. In some embodiments, the wound is a chronic wound. Specifically contemplated chronic wounds include, for example, a venous ulcer and a pressure sore. In various embodiments, the wound is a diabetic wound. Specifically contemplated diabetic wounds include, for example, a diabetic foot ulcer.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE INVENTION

Figure 1:
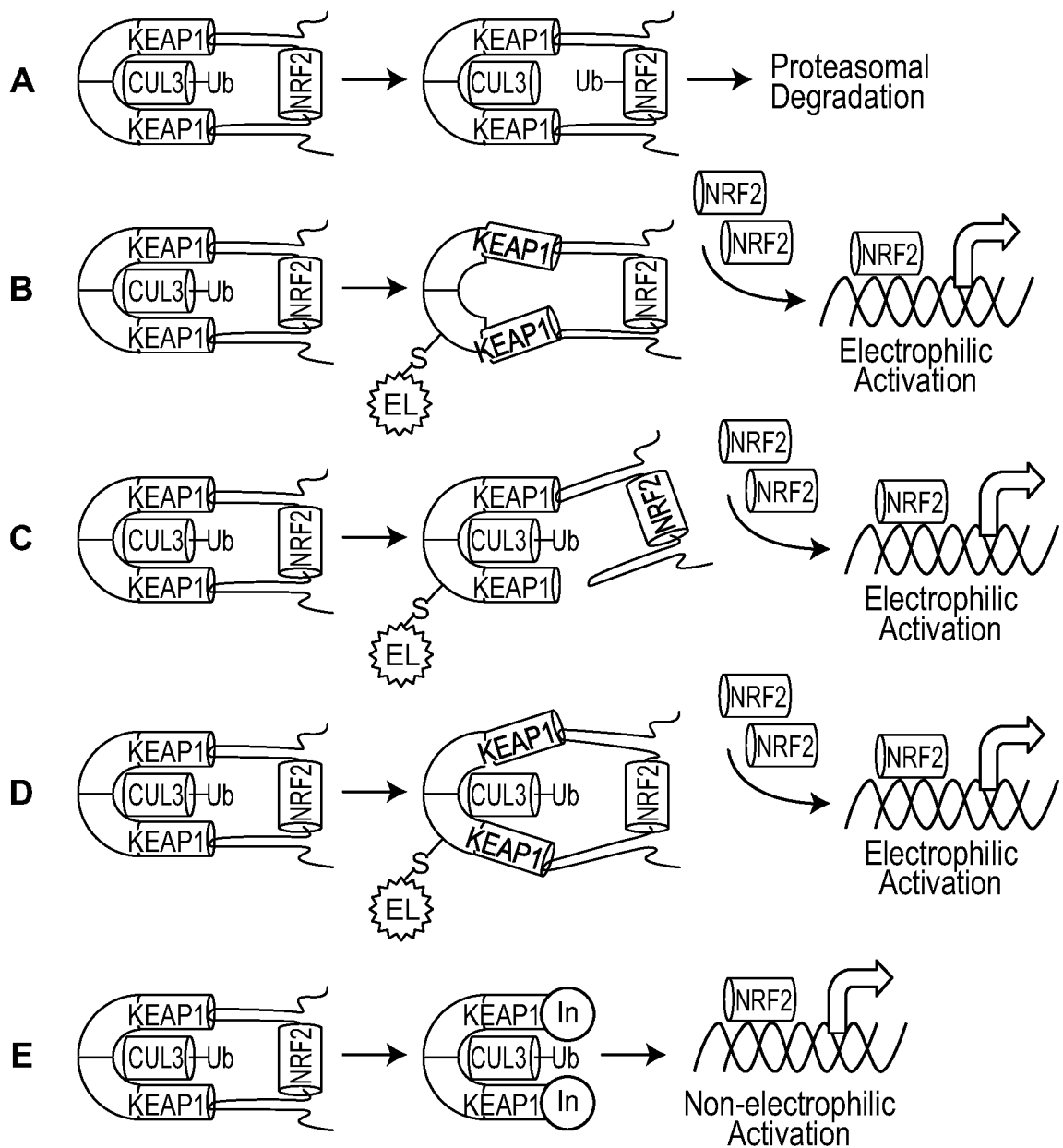
FIG. 1 (A) Transcription factor NRF2, when bound to substrate adaptor KEAP1, is ubiquitinated by E3 ligase CUL3, leading to proteosomal degradation. Three mechanisms explain activation of NRF2 by electrophiles. (B) In the CUL3 dissociation mechanism, cysteine modification by an electrophile causes dissociation of CUL3, leading to accumulation of NRF2. (C) In the hinge-and-latch mechanism, cysteine modification causes nonoptimal placement of NRF2 for degradation. (D) In the conformational cycling model, cysteine modification locks KEAP1 and NRF2 in a conformation not ideal for ubiquitination, preventing KEAP1 from binding nascent NRF2, leading to accumulation of NRF2. (E) The nonelectrophilic mechanism aims to create a noncovalent inhibitor of the protein-protein interaction between KEAP1 and NRF2 to activate NRF2.

Provided herein are compounds having a 1,4-substituted isoquinoline core that can act as inhibitors of the Kelch-like ECH-associated protein 1/nuclear factor (erythroid-derived 2)-like 2 ("KEAP1-NRF2") protein-protein interaction, and methods of using the compounds to treat and prevent diseases and disorders associated with dysregulation of the KEAP1-NRF2 interaction, such as chronic obstructive pulmonary disease ("COPD"), multiple sclerosis, diabetic chronic wounds, and chronic kidney disease. The compounds disclosed herein include a and exhibit similar or superior potency, aqueous solubility, and metabolic stability to the 1,4-naphthalene compounds, but also display an improved mutagenic profile.

The compounds of the disclosure can inhibit the KEAP1-NRF2 interaction by more than about 50%, 55%, 60%, 65%, 70%, 75%, 80%, 85%, 90%, 95%, 97%, or 99% of the positive control. In some embodiments, the compounds of the disclosure can inhibit the KEAP1-NRF2 interaction by more than about 75%, 80%, 85%, 90%, 95%, 97%, or 99% of the positive control. For example, the compounds disclosed herein can inhibit the KEAP1-NRF2 interaction by more than about 85%, 86%, 87%, 88%, 89%, 90%, 91%, 92%, 93%, 94%, 95%, 96%, 97%, 98%, or 99% of the positive control. Furthermore, the compounds disclosed herein can inhibit the KEAP1-NRF2 interaction with an $IC_{50}$ of less than about 3 µM, or less than about 2 µM, or less than about 1 µM, or less than about 0.5 µM, or less than about 0.4 µM, or less than about 0.3 µM, or less than about 0.2 µM, or less than about 0.1 µM, or less than about 90 nM, or less than about 80 nM, or less than about 70 nM, or less than about 60 nM, or less than about 50 nM, or less than about 40 nM, or less than about 30 nM, or less than about 20 nM, or less than about 10 nM.

Chemical Definitions

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), isobutyl (2,2-dimethylethyl), t-butyl (1,1-dimethylethyl), 3,3-dimethylpentyl, and 2-ethylhexyl. Unless otherwise indicated, an alkyl group can be an unsubstituted alkyl group or a substituted alkyl group. A deuterated alkyl group refers to an alkyl group in which at least one carbon atom has been substituted with deuterium. For example, "deuterated $C_{1-6}$alkyl" refers an alkyl group having 1 to 6 carbon atoms in which at least one carbon atom is substituted with deuterium (e.g., $CD_3$). As used herein, "haloalkyl" refers to an alkyl group in which at least one carbon atom has been substituted with a halogen. For example, $C_{1-6}$haloalkyl refers an alkyl group having 1 to 6 carbon atoms in which at least one carbon atom is substituted with a halogen (e.g., $CF_3$, $CH_2CF_3$, $CF_2CH_3$, $CH_2CF_2H$, $CH_2CFH_2$, or $CH_2CH_2CF$).

As used herein, the term "alkylene" refers to an alkyl group having a substituent. For example, the term "alkylene-CN" refers to an alkyl group substituted with a CN group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. As described previously, the term "haloalkyl" refers to an alkyl group that is substituted with at least one halogen.

As used herein, the term "alkoxy" refers to —OR, wherein 'R' is a radical (e.g., $OCH_3$). The term "haloalkoxy" refers to an alkoxy group that is substituted with at least one halogen (e.g., $OCF_3$).

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

The chemical structures having one or more stereocenters depicted with dashed and bold bonds (i.e., ⋯ and ▬) are meant to indicate absolute stereochemistry of the stereocenter(s) present in the chemical structure. Bonds symbolized by a simple line do not indicate a stereo-preference. Unless otherwise indicated to the contrary, chemical structures that include one or more stereocenters which are illustrated herein without indicating absolute or relative stereochemistry, encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

KEAP1/NRF2 Protein-Protein Interaction Inhibitors

Disclosed herein are compounds that can inhibit the interaction of the proteins KEAP1 and NRF2 ("KEAP-1/NRF2 inhibitors") having a structure of Formula (I), or a pharmaceutically acceptable salt thereof:

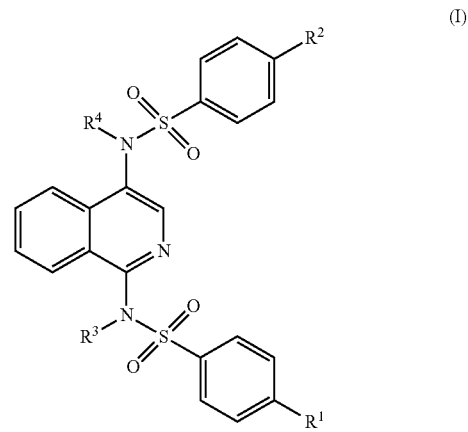

(I)

wherein
each of $R^1$ and $R^2$ independently is halo, OH, CN, $C_{1-6}$haloalkyl, $C_{1-6}$alkoxy, $C_{1-6}$haloalkoxy, or $C(O)R^6$;

each of $R^3$ and $R^4$ independently is H, $C_{1-6}$alkyl, deuterated $C_{1-6}$alkyl, $C_{1-6}$haloalkyl, $C_{1-6}$alkylene-CN, $C_{0-6}$alkylene-$C_{1-5}$heteroaryl having 1, 2, 3, or 4 heteroatoms selected from N, O, and S, $C_{0-6}$alkylene-C(O)$R^6$, $C_{0-6}$alkylene-N($R^5$)SO$_2$$R^7$, $C_{0-6}$alkylene-C(O)N($R^5$)SO$_2$$R^7$, $C_{0-6}$alkylene-C(O)NHOH, or $C_{0-6}$alkylene-C=N(OH)N($R^5$)$_2$;
each $R^5$ independently is H or $C_{1-6}$alkyl;
$R^6$ is OH, $C_{1-6}$haloalkyl, or $C_{1-6}$alkoxy; and
$R^7$ is $C_{1-6}$alkyl or N($R^5$)$_2$.

In some embodiments, at least one of $R^1$ and $R^2$ is halo. In various embodiments, each of $R^1$ and $R^2$ is halo. In some cases, at least one of $R^1$ and $R^2$ is F or Cl. In various cases, each of $R^1$ and $R^2$ independently is F or Cl. In some embodiments, at least one of $R^1$ and $R^2$ is F. In various embodiments, each of $R^1$ and $R^2$ is F. In some cases, at least one of $R^1$ and $R^2$ is OH. In various cases, each of $R^1$ and $R^2$ is OH. In some embodiments, at least one of $R^1$ and $R^2$ is CN. In various embodiments, each of $R^1$ and $R^2$ is CN. In some cases, at least one of $R^1$ and $R^2$ is $C_{1-6}$alkoxy. In various, cases, each of $R^1$ and $R^2$ is $C_{1-6}$alkoxy. In some embodiments, at least one of $R^1$ and $R^2$ is $C_{1-6}$alkoxy. In various, cases, each of $R^1$ and $R^2$ is $C_{1-6}$alkoxy. In some cases, at least one of $R^1$ and $R^2$ is OCH$_3$. In various cases, each of $R^1$ and $R^2$ is OCH$_3$. In some embodiments, at least one of $R^1$ and $R^2$ is COOH or C(O)$C_{1-6}$alkoxy. In various embodiments, at least one of $R^1$ and $R^2$ is COOH or C(O)$C_{1-3}$alkoxy. In some cases, at least one of $R^1$ and $R^2$ is COOH. In various cases, each of $R^1$ and $R^2$ is COOH. In some embodiments, at least one of $R^1$ and $R^2$ is C(O)OCH$_3$. In various cases, each of $R^1$ and $R^2$ is C(O)OCH$_3$. In some cases, at least one of $R^1$ and $R^2$ independently is $C_{1-6}$haloalkyl, $C_{1-6}$haloalkoxy, or C(O)$C_{1-6}$haloalkyl. In some embodiments, at least one of $R^1$ and $R^2$ independently is CF$_3$, OCF$_3$, or C(O)CF$_3$. In various embodiments, each of $R^1$ and $R^2$ independently is $C_{1-6}$haloalkyl, $C_{1-6}$haloalkoxy, or C(O)$C_{1-6}$haloalkyl. In some cases, each of $R^1$ and $R^2$ independently is CF$_3$, OCF$_3$, or C(O)CF$_3$. In various cases, each of $R^1$ and $R^2$ is F, or each of $R^1$ and $R^2$ is Cl, or each of $R^1$ and $R^2$ is CN, or each of $R^1$ and $R^2$ is CF$_3$, or each of $R^1$ and $R^2$ is OCF$_3$, or each of $R^1$ and $R^2$ is C(O)CF$_3$. In some cases, each of $R^1$ and $R^2$ independently is OCH$_3$, F, Cl, CN, CF$_3$, OCF$_3$, or C(O)CF$_3$. In various cases, each of $R^1$ and $R^2$ independently is OCH$_3$ or F. In some embodiments, $R^1$ is Cl, and $R^2$ is F. In various embodiments, $R^1$ is CN, and $R^2$ is F. In some cases, $R^1$ is CF$_3$, and $R^2$ is F. In various cases, $R^1$ is OCF$_3$, and $R^2$ is F. In some embodiments, $R^1$ is C(O)CF$_3$, and $R^2$ is F. In various embodiments, $R^1$ is F, and $R^2$ is C. In some cases, $R^1$ is F, and $R^2$ is CN. In various cases, $R^1$ is F, and $R^2$ is CF$_3$. In some embodiments, $R^1$ is F, and $R^2$ is OCF$_3$. In some embodiments, $R^1$ is F and $R^2$ is C(O)CF$_3$. In various embodiments, $R^1$ is CN and $R^2$ is C. In some cases, $R^1$ is CF$_3$ and $R^2$ is Cl. In various cases, $R^1$ is OCF$_3$ and $R^2$ is C. In some embodiments, $R^1$ is C(O)CF$_3$ and $R^2$ is Cl. In various cases, $R^1$ is C and $R^2$ is CN. In some cases, $R^1$ is Cl and $R^2$ is CF$_3$. In some cases, $R^1$ is C and $R^2$ is OCF$_3$. In various cases, $R^1$ is C and $R^2$ is C(O)CF$_3$. In some cases, $R^1$ is CF$_3$ and $R^2$ is CN. In various cases, $R^1$ is OCF$_3$ and $R^2$ is CN. In some embodiments, $R^1$ is C(O)CF$_3$ and $R^2$ is CN. In various cases, $R^1$ is CN and $R^2$ is CF$_3$. In some cases, $R^1$ is CN and $R^2$ is OCF$_3$. In various cases, $R^1$ is CN and $R^2$ is C(O)CF$_3$. In some embodiments, $R^1$ is OCF$_3$ and $R^2$ is CF$_3$. In various embodiments, $R^1$ is C(O)CF$_3$ and $R^2$ is CF$_3$. In some cases, $R^1$ is CF$_3$ and $R^2$ is OCF$_3$. In various cases, $R^1$ is CF$_3$ and $R^2$ is C(O)CF$_3$. In some embodiments, $R^1$ is C(O)CF$_3$ and $R^2$ is OCF$_3$. In various embodiments, $R^1$ is OCF$_3$ and $R^2$ is C(O)CF$_3$.

In some embodiments, at least one of $R^3$ and $R^4$ is H. In various embodiments, $R^3$ is H. In some cases, $R^3$ is H and $R^4$ is not H. In various cases, at least one of $R^3$ and $R^4$ is $C_{1-6}$alkyl or deuterated $C_{1-6}$alkyl. In some embodiments, at least one of $R^3$ and $R^4$ is $C_{1-3}$alkyl or deuterated $C_{1-3}$alkyl. In various embodiments, at least one of $R^3$ and $R^4$ is CH$_3$ or CD$_3$. In some cases, $R^4$ is CH$_3$ or CD$_3$. In various cases, at least one of $R^3$ and $R^4$ is $C_{0-6}$alkylene-C(O)$R^6$. In some embodiments, at least one of $R^3$ and $R^4$ is CH$_2$COOH, CH(CH$_3$)COOH, or CH$_2$C(O)CF$_3$. In various embodiments each of $R^3$ and $R^4$ independently is CH$_2$COOH, CH(CH$_3$)COOH, or CH$_2$C(O)CF$_3$. In some cases, $R^3$ is CH$_2$COOH or CH(CH$_3$)COOH. In various cases, $R^3$ is CH$_2$COOH. In some embodiments, $R^4$ is CH$_2$C(O)CF$_3$. In various embodiments, at least one of $R^3$ and $R^4$ is $C_{1-6}$haloalkyl or $C_{1-6}$alkylene-CN. In some cases, at least one of $R^3$ and $R^4$ is CF$_3$, CH$_2$CF$_3$, CF$_2$CH$_3$, CH$_2$CF$_2$H, CH$_2$CFH$_2$, CH$_2$CH$_2$CF$_3$ or CH$_2$CN. In various cases, $R^4$ is CF$_3$, CH$_2$CF$_3$, CF$_2$CH$_3$, CH$_2$CF$_2$H, CH$_2$CFH$_2$, CH$_2$CH$_2$CF$_3$ or CH$_2$CN. In some embodiments, $R^4$ is CH$_2$CF$_3$. In some embodiments, at least one of $R^3$ and $R^4$ is $C_{0-6}$alkylene-$C_{1-5}$heteroaryl having 1, 2, 3, or 4 heteroatoms selected from N, O, and S. In various embodiments, at least one of $R^3$ and $R^4$ is tetrazolyl, oxadiazolonyl, thiadiazolonyl, oxathadiazolyl oxide, or oxadiazolthionyl. In some cases, at least one of $R^3$ and $R^4$ is

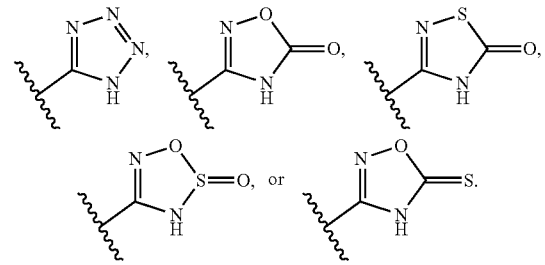

In various cases, $R^3$ is tetrazolyl, oxadiazolonyl, thiadiazolonyl, oxathadiazolyl oxide, or oxadiazolthionyl. In some embodiments, $R^3$ is

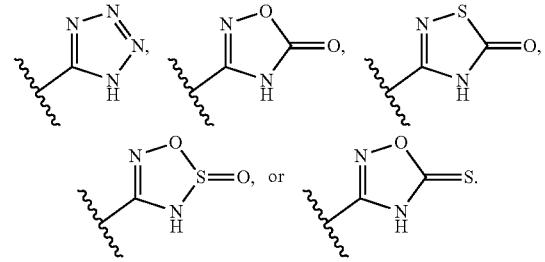

In various embodiments, at least one of $R^3$ and $R^4$ is $C_{0-6}$alkylene-N($R^5$)SO$_2$$R^7$, $C_{0-6}$alkylene-C(O)N($R^5$)SO$_2$$R^7$, $C_{0-6}$alkylene-C(O)NHOH, or $C_{1-6}$alkylene-C=N(OH)N($R^5$)$_2$. In some cases, each $R^5$ independently is H or CH$_3$. In various cases, $R^7$ is CH$_3$ or N(CH$_3$)$_2$. In some embodiments, at least one of $R^3$ and $R^4$ is CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$. In various embodiments, $R^3$ is CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$. In some cases, $R^3$ is CH$_2$COOH, CH(CH$_3$)COOH,

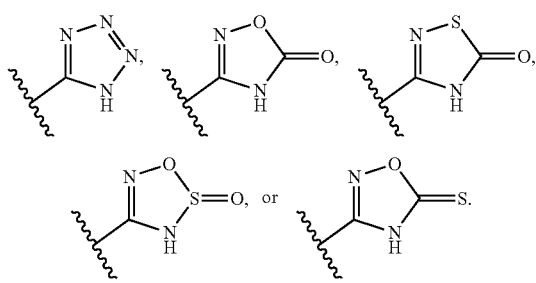

CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$. In various cases, R$^3$ is H and R$^4$ is CH$_2$COOH. In some embodiments, R$^3$ is CH$_3$ and R$^4$ is CH$_2$COOH. In various embodiments, R$^3$ is CH$_2$COOH and R$^4$ is H. In some cases, R$^3$ is CH(CH$_3$)COOH and R$^4$ is H. In various cases, R$^3$ is CH$_2$COOH and R$^4$ is CH$_3$. In some embodiments, R$^3$ is CH$_2$COOH and R$^4$ is CD$_3$. In various embodiments, R$^3$ is CH$_2$C(O)NHOH and R$^4$ is CH$_2$CF$_3$. In some cases, R$^3$ is CH$_2$C(O)NHSO$_2$CH$_3$ and R$^4$ is CH$_2$CF$_3$. In various cases, R$^3$ is CH$_2$C(O)NHSO$_2$N(CH$_3$)$_2$ and R$^4$ is CH$_2$CF$_3$. In some embodiments, R$^3$ is CH$_2$CH$_2$NHSO$_2$CH$_3$ and R$^4$ is CH$_2$CF$_3$. In various embodiments, R$^3$ is CH$_2$C=N(OH)NH$_2$ and R$^4$ is CH$_2$CF$_3$. In some cases, R$^3$ is

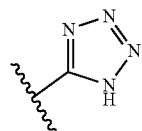

and R$^4$ is CH$_2$CF$_3$. In various cases, R$^3$ is

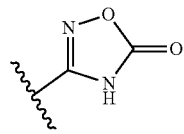 [SMILES: *c1noc(=O)[nH]1]

and R$^4$ is CH$_2$CF$_3$. In some embodiments cases, R$^3$ is

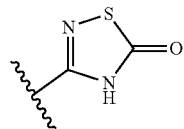 [SMILES: *c1nsc(=O)[nH]1]

and R$^4$ is CH$_2$CF$_3$. In various embodiments, R$^3$ is

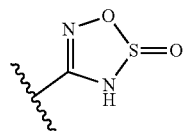 [SMILES: *C1=NOS(=O)N1]

and R$^4$ is CH$_2$CF$_3$. In some cases, R$^3$ is

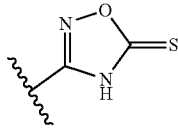

and R$^4$ is CH$_2$CF$_3$. In various cases, R$^3$ is CH$_2$COOH and R$^4$ is CF$_3$. In some embodiments, R$^3$ is CH$_2$COOH and R$^4$ is CH$_2$CF$_2$H. In various embodiments, R$^3$ is CH$_2$COOH and R$^4$ is CH$_2$CFH$_2$. In some cases, R$^3$ is CH$_2$COOH and R$^4$ is CH$_2$CH$_2$CF$_3$. In various cases, R$^3$ is CH$_2$COOH and R$^4$ is CH$_2$CN. In some embodiments, R$^3$ is CH$_2$COOH and R$^4$ is CH$_2$C(O)CF$_3$.

In some embodiments, each of R$^1$ and R$^2$ independently is halo, OH, CN, C$_{1-6}$haloalkyl, C$_{1-6}$alkoxy, C$_{1-6}$haloalkoxy, or C(O)C$_{1-6}$haloalkyl; R$^3$ is C$_{0-6}$alkylene-COOH, C$_{0-6}$alkylene-C(O)C$_{1-6}$alkoxy, C$_{0-6}$alkylene-C$_{1-5}$heteroaryl having 1, 2, 3, or 4 heteroatoms selected from N, O, and S, C$_{0-6}$alkylene-N(R$^5$)SO$_2$R$^7$, C$_{0-6}$alkylene-C(O)N(R$^5$)SO$_2$R$^7$, C$_{1-6}$alkylene-C(O)NHOH, or C$_{0-6}$alkylene-C=N(OH)N(R$^5$)$_2$; R$^4$ is H, C$_{1-6}$haloalkyl, C$_{1-6}$alkylene-CN, or C$_{0-6}$alkylene-C(O)C$_{1-6}$haloalkyl; each R$^5$ independently is H or C$_{1-6}$alkyl; and R$^7$ is C$_{1-6}$alkyl or N(R$^5$)$_2$. In some cases, each of R$^1$ and R$^2$ independently is OCH$_3$, F, Cl, CN, CF$_3$, OCF$_3$, or C(O)CF$_3$; R$^3$ is CH$_2$COOH, CH(CH$_3$)COOH,

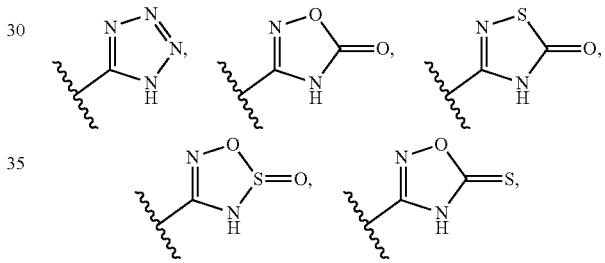

CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$; and R$^4$ is H, CF$_3$, CH$_2$CF$_3$, CF$_2$CH$_3$, CH$_2$CF$_2$H, CH$_2$CFH$_2$, CH$_2$CH$_2$CF$_3$, or CH$_2$CN. In various cases, each of R$^1$ and R$^2$ independently is OCH$_3$ or F; R$^3$ is CH$_2$COOH; and R$^4$ is H or CH$_2$CF$_3$. In various cases, each of R$^1$ and R$^2$ independently is F, Cl, CN, CF$_3$, OCF$_3$, or C(O)CF$_3$; R$^3$ is CH$_2$COOH, CH(CH$_3$)COOH,

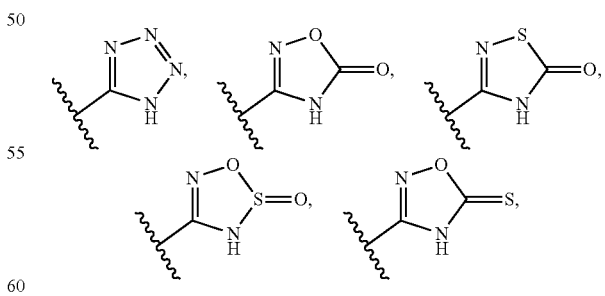

CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$; and R$^4$ is H, CF$_3$, CH$_2$CF$_3$, CF$_2$CH$_3$, CH$_2$CF$_2$H, CH$_2$CFH$_2$, CH$_2$CH$_2$CF$_3$, or CH$_2$CN. In various cases, each of R$^1$ and R$^2$ independently is OCH$_3$ or F; R$^3$ is CH$_2$COOH; and R$^4$ is H or CH$_2$CF$_3$ Specifically contemplated compounds of the disclosure include compounds listed in Table A, or pharmaceutically acceptable salts thereof:
Table A
| Compound no. | Structure |
| --- | --- |
| A1 | 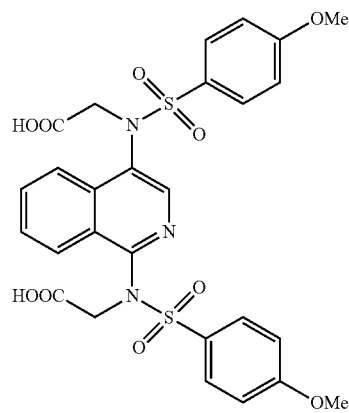 [SMILES: COc1ccc(S(=O)(=O)N(CC(=O)O)c2cnc(N(CC(=O)O)S(=O)(=O)c3ccc(OC)cc3)c3ccccc23)cc1] |
| A2 | 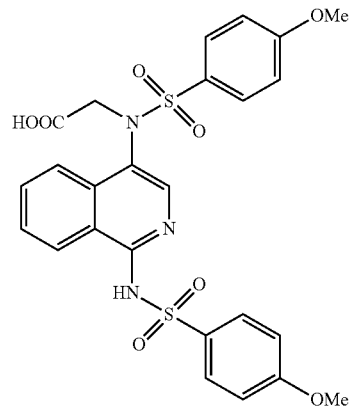 [SMILES: COc1ccc(S(=O)(=O)Nc2ncc(N(CC(=O)O)S(=O)(=O)c3ccc(OC)cc3)c3ccccc23)cc1] |
| A3 | 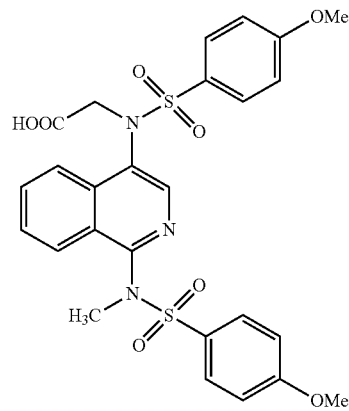 [SMILES: COc1ccc(S(=O)(=O)N(C)c2ncc(N(CC(=O)O)S(=O)(=O)c3ccc(OC)cc3)c3ccccc23)cc1] |
TABLE A-continued
| Compound no. | Structure |
| --- | --- |
| A4 | 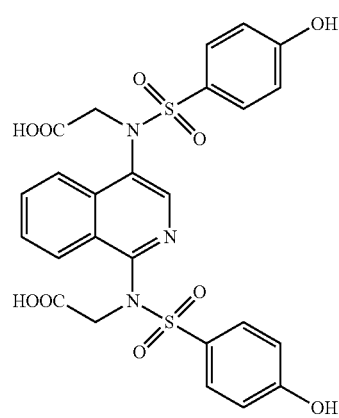 [SMILES: O=C(O)CN(c1cnc(N(CC(=O)O)S(=O)(=O)c2ccc(O)cc2)c2ccccc12)S(=O)(=O)c1ccc(O)cc1] |
| A5 | 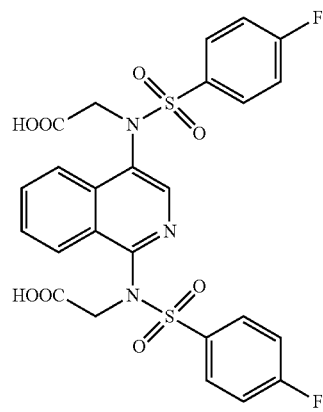 [SMILES: O=C(O)CN(c1cnc(N(CC(=O)O)S(=O)(=O)c2ccc(F)cc2)c2ccccc12)S(=O)(=O)c1ccc(F)cc1] |
| A6 | 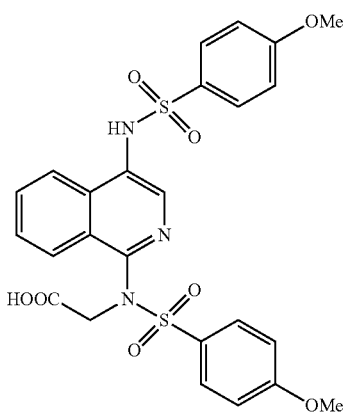 [SMILES: COc1ccc(S(=O)(=O)Nc2cnc(N(CC(=O)O)S(=O)(=O)c3ccc(OC)cc3)c3ccccc23)cc1] |

TABLE A-continued

| Compound no. | Structure |
|---|---|
| A7 | (structure: isoquinoline with 4-NH-SO2-C6H4-OMe and 1-N(CH(Me)COOH)-SO2-C6H4-OMe) |
| A8 | (structure: isoquinoline with 4-N(CH3)-SO2-C6H4-OMe and 1-N(CH2COOH)-SO2-C6H4-OMe) |
| A9 | (structure: isoquinoline with 4-N(CD3)-SO2-C6H4-OMe and 1-N(CH2COOH)-SO2-C6H4-OMe) |

Additional specifically contemplated compounds of the disclosure include compounds listed in Table B, or pharmaceutically acceptable salts thereof:

TABLE B

| Compound no. | Structure |
|---|---|
| B0 | (structure: isoquinoline with 4-N(CH2CF3)-SO2-C6H4-OMe and 1-N(CH2COOH)-SO2-C6H4-OMe) |
| B1 | (structure: isoquinoline with 4-N(CH2CF3)-SO2-C6H4-OMe and 1-N(CH2C(O)NHOH)-SO2-C6H4-OMe) |
| B2 | (structure: isoquinoline with 4-N(CH2CF3)-SO2-C6H4-OMe and 1-N(CH2C(O)NHSO2CH3)-SO2-C6H4-OMe) |

TABLE B-continued
| Compound no. | Structure |
|---|---|
| B3 | 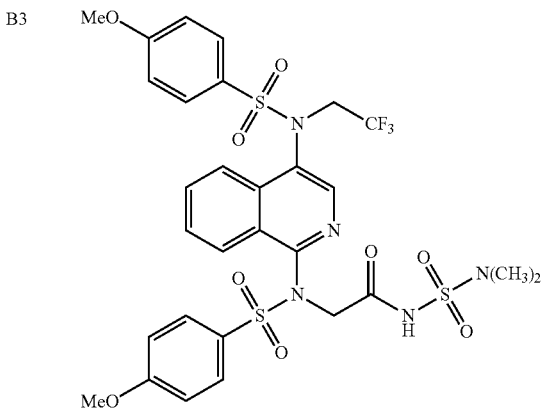 |
| B4 | 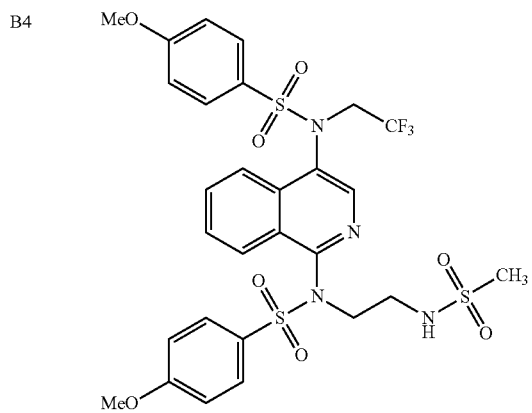 |
| B5 | 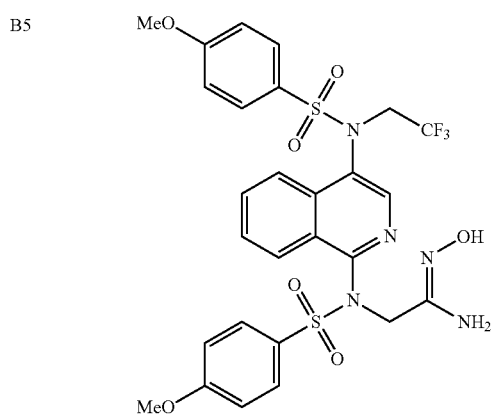 |
| B6 | 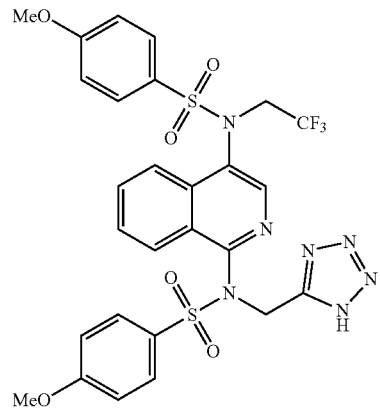 |
| B7 | 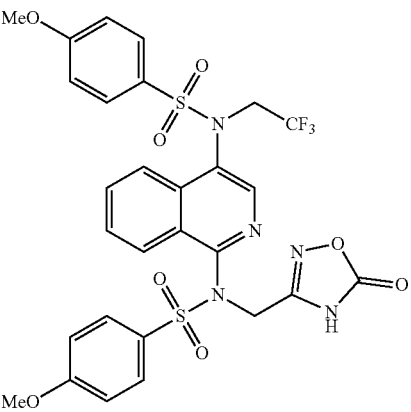 |
| B8 | 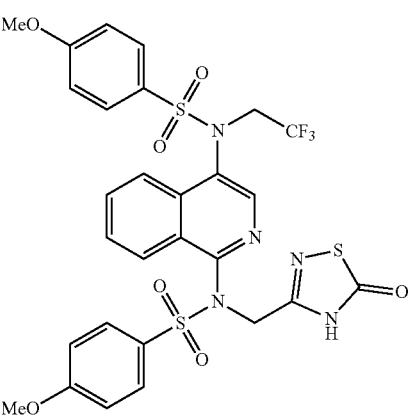 |

TABLE B-continued
| Compound no. | Structure |
|---|---|
| B9 | 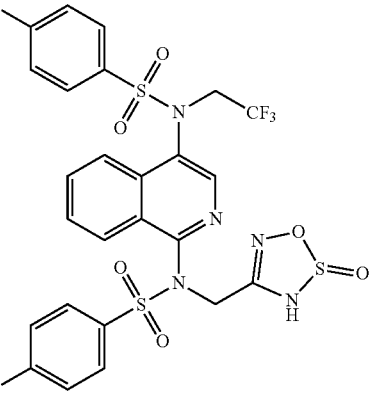 |
| B10 | 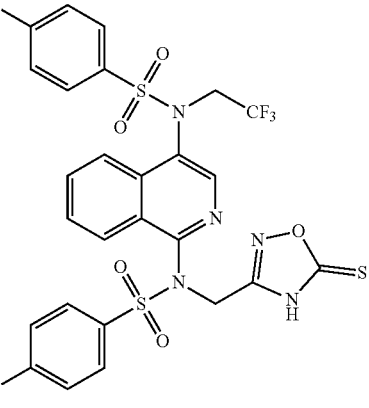 |
| B11 | 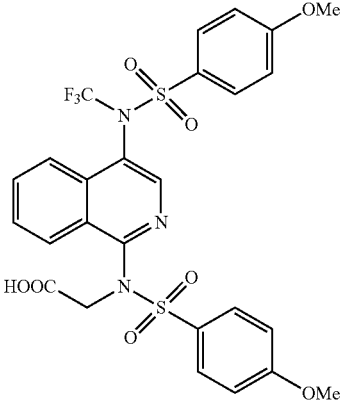 [SMILES: COc1ccc(S(=O)(=O)N(C)c2cnc(N(CC(=O)O)S(=O)(=O)c3ccc(OC)cc3)c3ccccc23)cc1] |
| B12 | 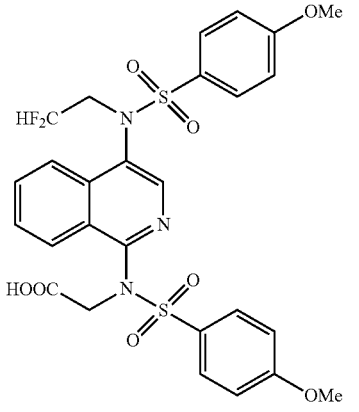 [SMILES: COc1ccc(S(=O)(=O)N(CC(F)(F)F)c2cnc(N(CC(=O)O)S(=O)(=O)c3ccc(OC)cc3)c3ccccc23)cc1] |
| B13 | 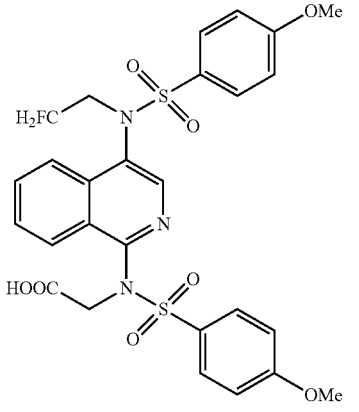 |
| B14 | 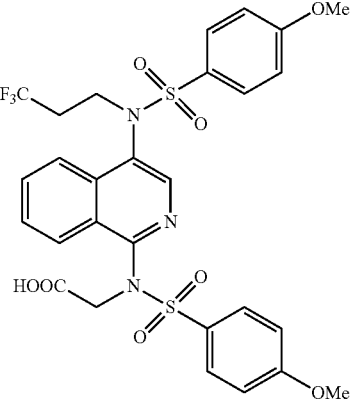 [SMILES: COc1ccc(S(=O)(=O)N(CCC(F)(F)F)c2cnc(N(CC(=O)O)S(=O)(=O)c3ccc(OC)cc3)c3ccccc23)cc1] |

TABLE B-continued

| Compound no. | Structure |
|---|---|
| B15 | (4-methoxyphenylsulfonyl-N-cyanomethyl) isoquinoline with N-(carboxymethyl)-4-methoxyphenylsulfonamide |
| B16 | (4-methoxyphenylsulfonyl-N-(trifluoroacetylmethyl)) isoquinoline with N-(carboxymethyl)-4-methoxyphenylsulfonamide |
| B17 | (4-fluorophenylsulfonyl-N-(2,2,2-trifluoroethyl)) isoquinoline with N-(carboxymethyl)-4-fluorophenylsulfonamide |
| B18 | (4-fluorophenylsulfonyl-N-(2,2,2-trifluoroethyl)) isoquinoline with N-(carboxymethyl)-4-chlorophenylsulfonamide |
| B19 | (4-fluorophenylsulfonyl-N-(2,2,2-trifluoroethyl)) isoquinoline with N-(carboxymethyl)-4-cyanophenylsulfonamide |
| B20 | (4-fluorophenylsulfonyl-N-(2,2,2-trifluoroethyl)) isoquinoline with N-(carboxymethyl)-4-trifluoromethylphenylsulfonamide |

TABLE B-continued

| Compound no. | Structure |
|---|---|
| B21 | (structure: isoquinoline core with N(CH2CF3)-SO2-C6H4-F at 4-position and N(CH2COOH)-SO2-C6H4-OCF3 at 1-position) |
| B22 | (structure: isoquinoline core with N(CH2CF3)-SO2-C6H4-F at 4-position and N(CH2COOH)-SO2-C6H4-C(O)CF3 at 1-position) |
| B23 | (structure: isoquinoline core with N(CH2CF3)-SO2-C6H4-Cl at 4-position and N(CH2COOH)-SO2-C6H4-F at 1-position) |
| B24 | (structure: isoquinoline core with N(CH2CF3)-SO2-C6H4-CN at 4-position and N(CH2COOH)-SO2-C6H4-F at 1-position) |
| B25 | (structure: isoquinoline core with N(CH2CF3)-SO2-C6H4-CF3 at 4-position and N(CH2COOH)-SO2-C6H4-F at 1-position) |
| B26 | (structure: isoquinoline core with N(CH2CF3)-SO2-C6H4-OCF3 at 4-position and N(CH2COOH)-SO2-C6H4-F at 1-position) |

TABLE B-continued

| Compound no. | Structure |
|---|---|
| B27 | (isoquinoline core with N(CH2CF3)-SO2-C6H4-C(O)CF3 at 4-position and N(CH2COOH)-SO2-C6H4-F at 1-position) |
| B28 | (isoquinoline core with N(CH2CF3)-SO2-C6H4-Cl at 4-position and N(CH2COOH)-SO2-C6H4-Cl at 1-position) |
| B29 | (isoquinoline core with N(CH2CF3)-SO2-C6H4-Cl at 4-position and N(CH2COOH)-SO2-C6H4-CN at 1-position) |
| B30 | (isoquinoline core with N(CH2CF3)-SO2-C6H4-Cl at 4-position and N(CH2COOH)-SO2-C6H4-CF3 at 1-position) |
| B31 | (isoquinoline core with N(CH2CF3)-SO2-C6H4-Cl at 4-position and N(CH2COOH)-SO2-C6H4-OCF3 at 1-position) |
| B32 | (isoquinoline core with N(CH2CF3)-SO2-C6H4-Cl at 4-position and N(CH2COOH)-SO2-C6H4-C(O)CF3 at 1-position) |

TABLE B-continued

| Compound no. | Structure |
|---|---|
| B33 | (structure) |
| B34 | (structure) |
| B35 | (structure) |
| B36 | (structure) |
| B37 | (structure) |
| B38 | (structure) |

TABLE B-continued

| Compound no. | Structure |
|---|---|
| B39 | (4-cyanophenylsulfonyl)(2,2,2-trifluoroethyl)amino-isoquinolin-1-yl-N-(carboxymethyl)-4-(trifluoromethoxy)benzenesulfonamide |
| B40 | (4-cyanophenylsulfonyl)(2,2,2-trifluoroethyl)amino-isoquinolin-1-yl-N-(carboxymethyl)-4-(2,2,2-trifluoroacetyl)benzenesulfonamide |
| B41 | (4-trifluoromethylphenylsulfonyl)(2,2,2-trifluoroethyl)amino-isoquinolin-1-yl-N-(carboxymethyl)-4-cyanobenzenesulfonamide |
| B42 | (4-trifluoromethoxyphenylsulfonyl)(2,2,2-trifluoroethyl)amino-isoquinolin-1-yl-N-(carboxymethyl)-4-cyanobenzenesulfonamide |
| B43 | (4-(2,2,2-trifluoroacetyl)phenylsulfonyl)(2,2,2-trifluoroethyl)amino-isoquinolin-1-yl-N-(carboxymethyl)-4-cyanobenzenesulfonamide |
| B44 | (4-trifluoromethylphenylsulfonyl)(2,2,2-trifluoroethyl)amino-isoquinolin-1-yl-N-(carboxymethyl)-4-(trifluoromethyl)benzenesulfonamide |

TABLE B-continued
| Compound no. | Structure |
|---|---|
| B45 | 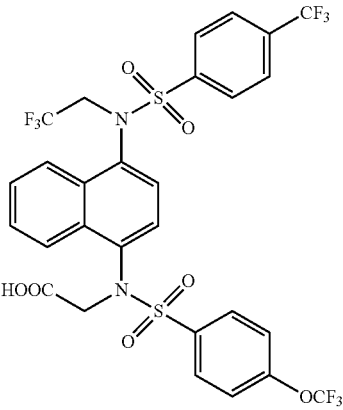 |
| B46 | 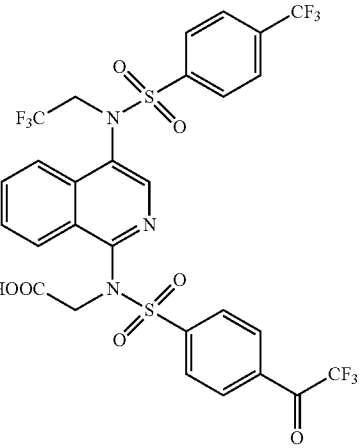 |
| B47 | 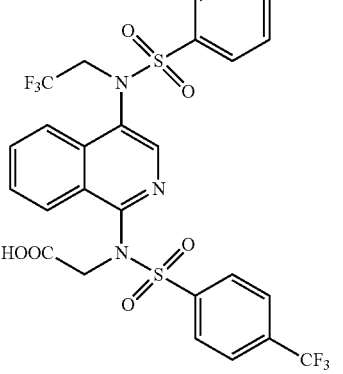 |
| B48 | 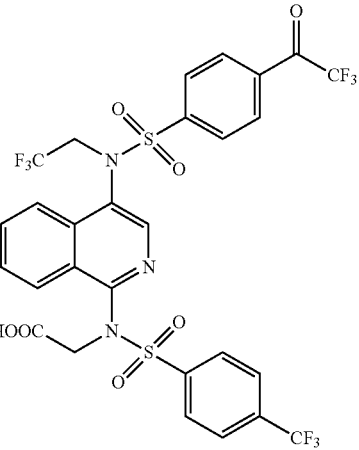 |
| B49 | 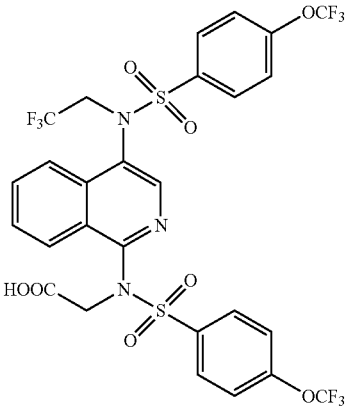 [SMILES: O=C(O)CN(c1ncc(N(CC(F)(F)F)S(=O)(=O)c2ccc(Cl)cc2)c2ccccc12)S(=O)(=O)c1ccc(OC(F)(F)F)cc1] |
| B50 | 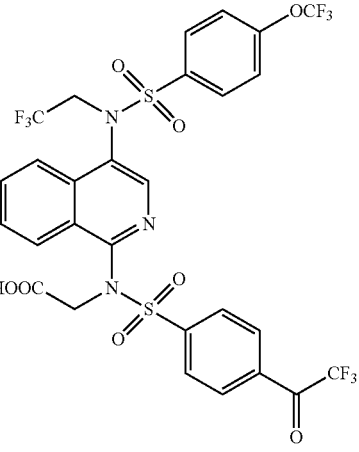 |

TABLE B-continued
| Compound no. | Structure |
|---|---|
| B51 | 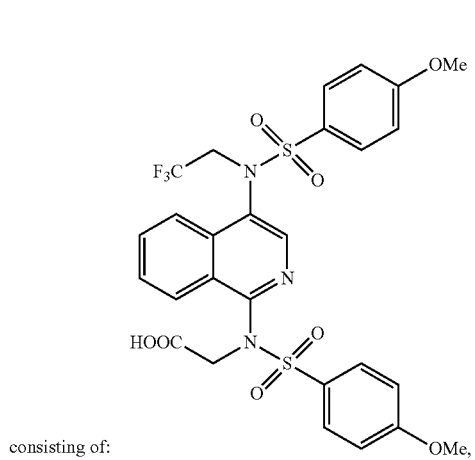 |
| B52 | 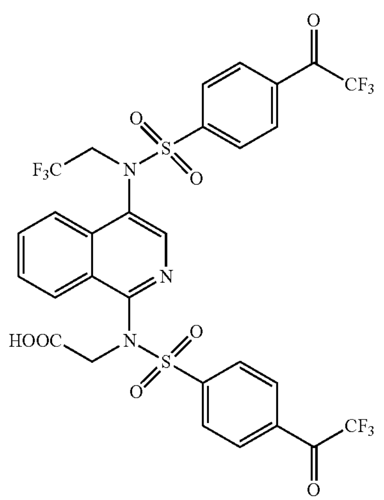 [SMILES: O=C(O)CN(c1ncc(N(CC(F)(F)F)S(=O)(=O)c2ccc(C(=O)C(F)(F)F)cc2)c2ccccc12)S(=O)(=O)c1ccc(C(=O)C(F)(F)F)cc1] |
In some cases, the compounds of the disclosure are selected from the group consisting of:
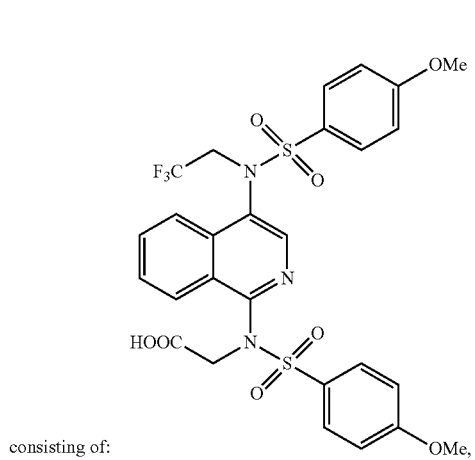
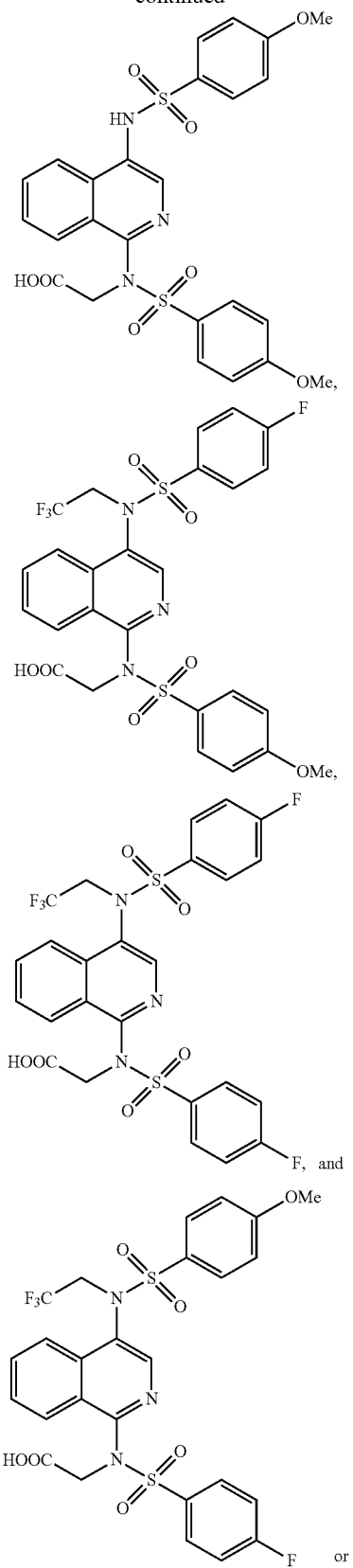
or pharmaceutically acceptable salts thereof. In some embodiments, the compound of Formula (I) has a structure:

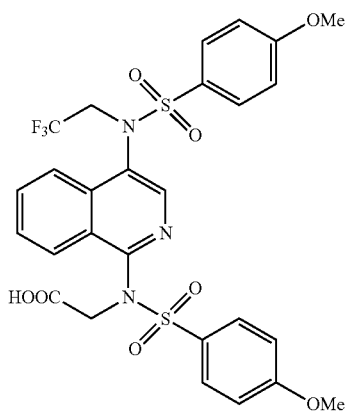 [SMILES: COc1ccc(S(=O)(=O)N(CC(F)(F)F)c2cnc(N(CC(=O)O)S(=O)(=O)c3ccc(OC)cc3)c3ccccc23)cc1]

or a pharmaceutically acceptable salt thereof.

It has been found that compounds having a 1,4-isoquinoline core structure can inhibit the KEAP-1/NRF2 interaction with nanomolar potency. It also has been found that 1,4-isoquinoline compounds having an acid functional group (e.g., $CH_2COOH$) at the 1-position of the isoquinoline ($R^3$) can exhibit increased potency. 1,4-isoquinoline compounds having an electron withdrawing group (e.g., $CH_2CF_3$) at the 4-position of the isoquinoline ($R^4$) have been found to exhibit enhanced metabolic stability and improved solubility. Although incorporating electron-donating groups (e.g., $OCH_3$) on the terminal phenyl groups (at positions $R^1$ and/or $R^2$) results in potent inhibitors, it has been found that replacing the electron-donating groups with electron-withdrawing groups (e.g., F, Cl, CN, $CF_3$, $OCF_3$, or $C(O)CF_3$)) can improve metabolic stability.

Also provided are compounds listed in Table C, or a pharmaceutically acceptable salt thereof:

TABLE C

| Compound no. | Structure |
|---|---|
| C1 | 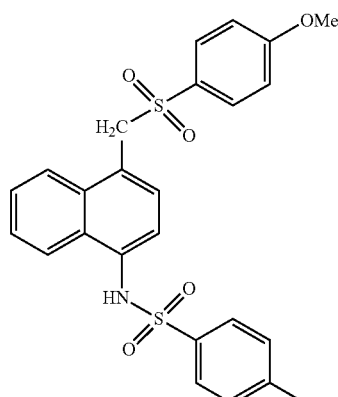 $IC_{50}$ 2900 |
| C2 | (see table continued) |

TABLE C-continued

| Compound no. | Structure |
|---|---|
| C2 | $IC_{50}$ 698 |
| C3 | $IC_{50}$ 167 |
| C4 | 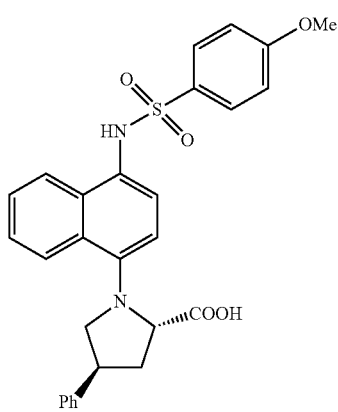 [SMILES: COc1ccc(S(=O)(=O)Nc2ccc(N3C[C@H](c4ccccc4)C[C@H]3C(=O)O)c3ccccc23)cc1] $IC_{50}$ 938 |

TABLE C-continued
| Compound no. | Structure |
|---|---|
| C5 | 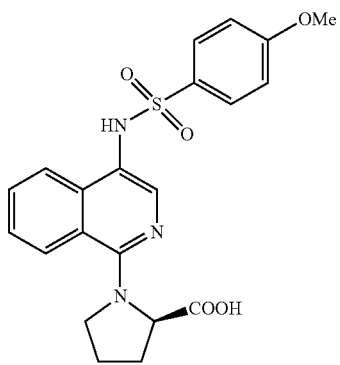 [SMILES: COc1ccc(S(=O)(=O)Nc2cnc(N3CCC[C@@H]3C(=O)O)c3ccccc23)cc1]<br>IC$_{50}$ >25,000 |
| C6 | 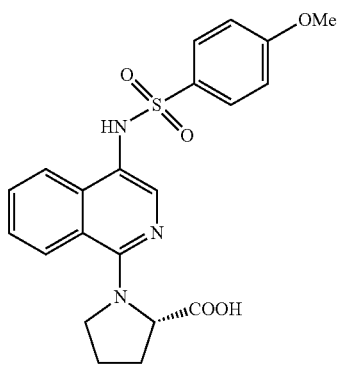 [SMILES: COc1ccc(S(=O)(=O)Nc2cnc(N3CCC[C@H]3C(=O)O)c3ccccc23)cc1]<br>IC$_{50}$ 5,000 |
| C7 | 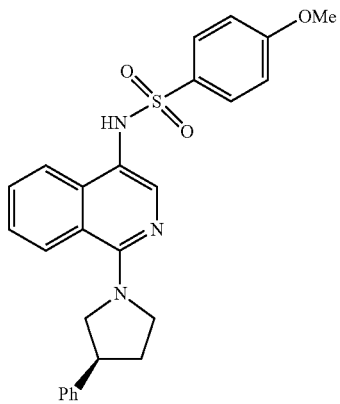 [SMILES: COc1ccc(S(=O)(=O)Nc2cnc(N3CC[C@@H](c4ccccc4)C3)c3ccccc23)cc1]<br>IC$_{50}$ >25,000 |
| C8 | 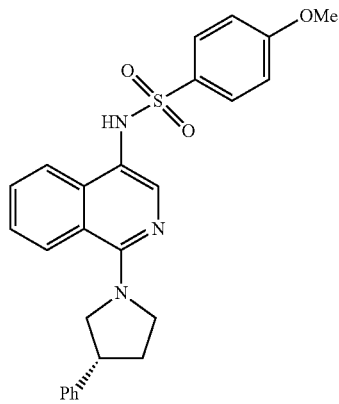 [SMILES: COc1ccc(S(=O)(=O)Nc2cnc(N3CC[C@H](c4ccccc4)C3)c3ccccc23)cc1]<br>IC$_{50}$ >25,000 |
| C9 | 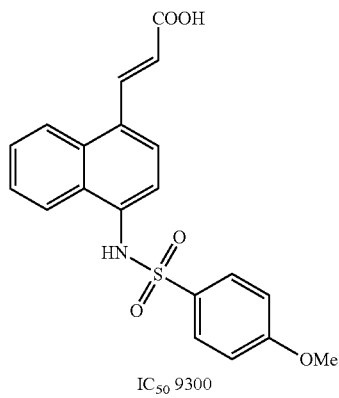<br>IC$_{50}$ 9300 |
| C10 | 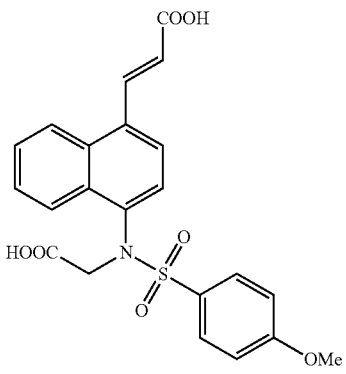 [SMILES: COc1ccc(S(=O)(=O)N(CC(=O)O)c2ccc(/C=C/C(=O)O)c3ccccc23)cc1]<br>IC$_{50}$ 11,000 |

TABLE C-continued

| Compound no. | Structure |
|---|---|
| C11 | 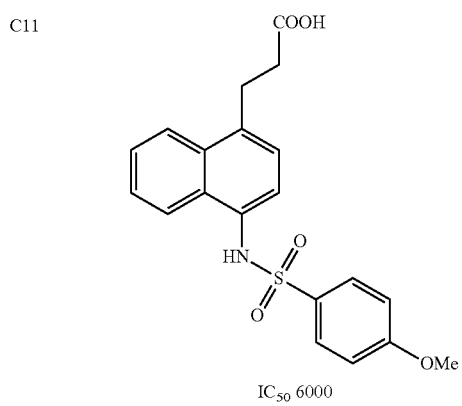<br>IC$_{50}$ 6000 |
| C12 | 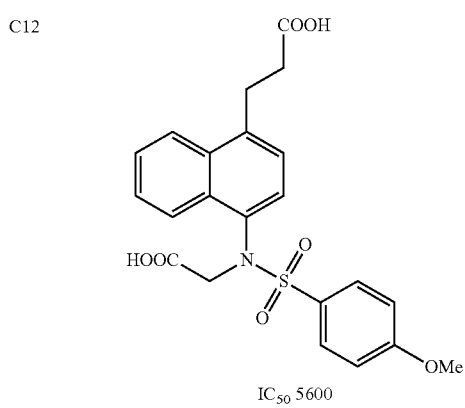<br>IC$_{50}$ 5600 |
| C13 | 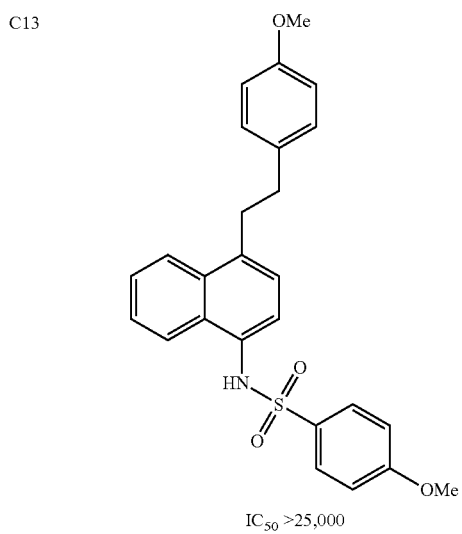<br>IC$_{50}$ >25,000 |
| C14 | 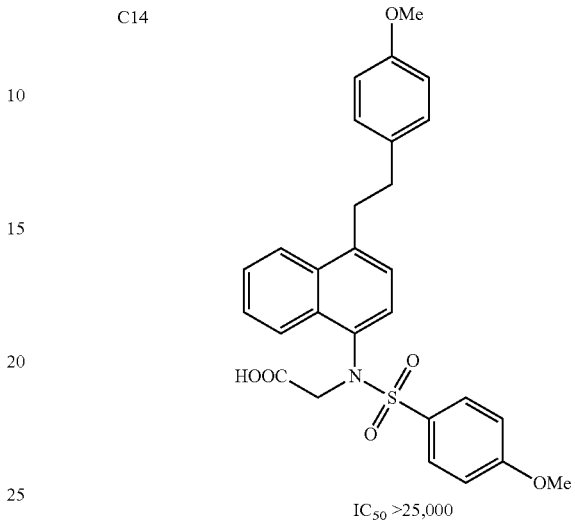<br>IC$_{50}$ >25,000 |

Synthesis of the KEAP1/NRF2 Inhibitors

The compounds of the disclosure can be synthesized by any method known to one skilled in the art. Scheme 1, below, depicts one method for synthesizing the compounds of the disclosure. Sulfonylation of 4-aminoisoquinoline a followed by protection (e.g., Boc protection) yields a sulfonamide, which can be further oxidized (by e.g., an mCPBA oxidation) to give the isoquinoline N-oxide b. Addition of a second sulfonamide (e.g., by a formal 3+3 addition with a hypervalent idodie-sulfonamide complex) produces compound c which can be further derivatized to produce compounds of the present disclosure, d.

Scheme 1

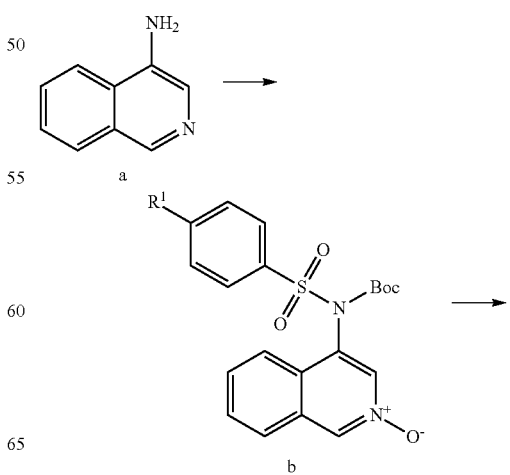

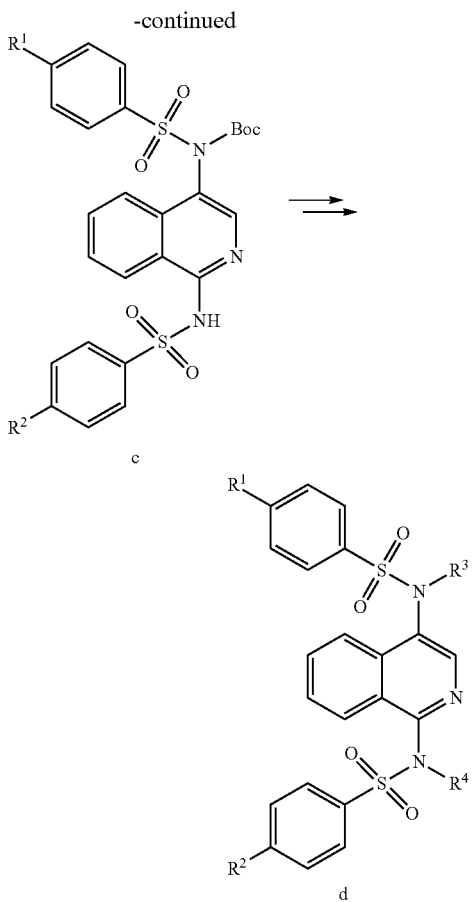

Additional synthetic procedures for preparing the compounds disclosed herein can be found in the Examples section.

Methods of Using the KEAP1/NRF2 Inhibitors

The compounds of the disclosure can inhibit the KEAP1-NRF2 interaction in a cell with nanomolar potency, and have been found to treat disorders and diseases, such as COPD, multiple sclerosis, diabetes, and skin diseases.

Figure 2:
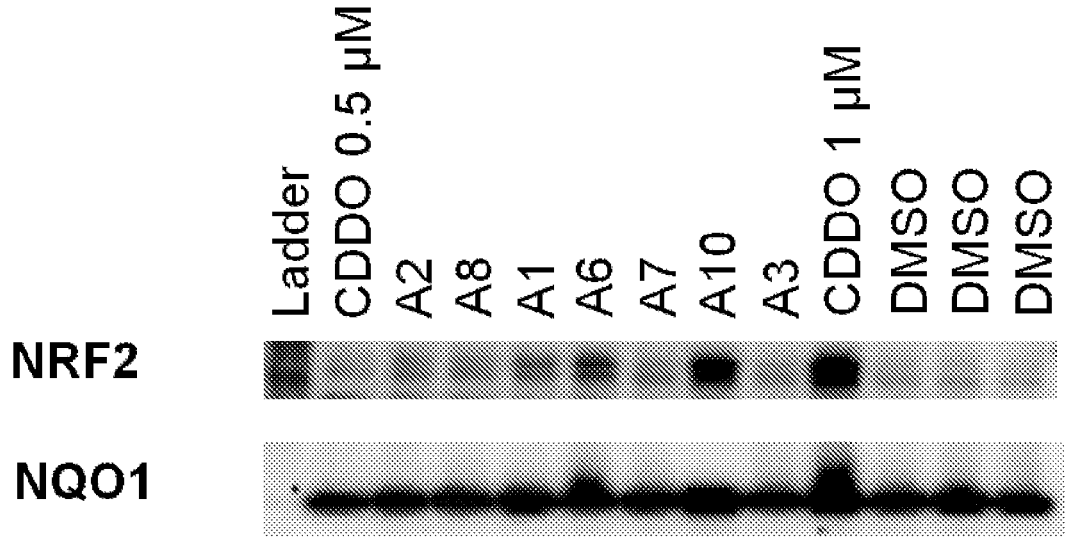
FIG. 2 shows protein levels of NRF2 and its target gene NADPH quinone oxidoreductase (NQO1), as determined by Western Blot in HaCat keratinocyte cells. Molecules that block the degradatior of NRF2 serve as NRF2 activators. This has the effect of stabilizing NRF2 protein levels and upregulating target gene levels, such as NQO1. Compounds A6 and B0 stabilize NRF2 expression, relative to vehicle (DMSO) control. CDDO is a positive control compound that activates NRF2 through an electrophilic mechanism. Compounds A6 and B0 also increase the levels of NQO1, an NRF2 target gene. HaCat Cells were treated with 10 μM compound unless otherwise indicated.
Figure 3:
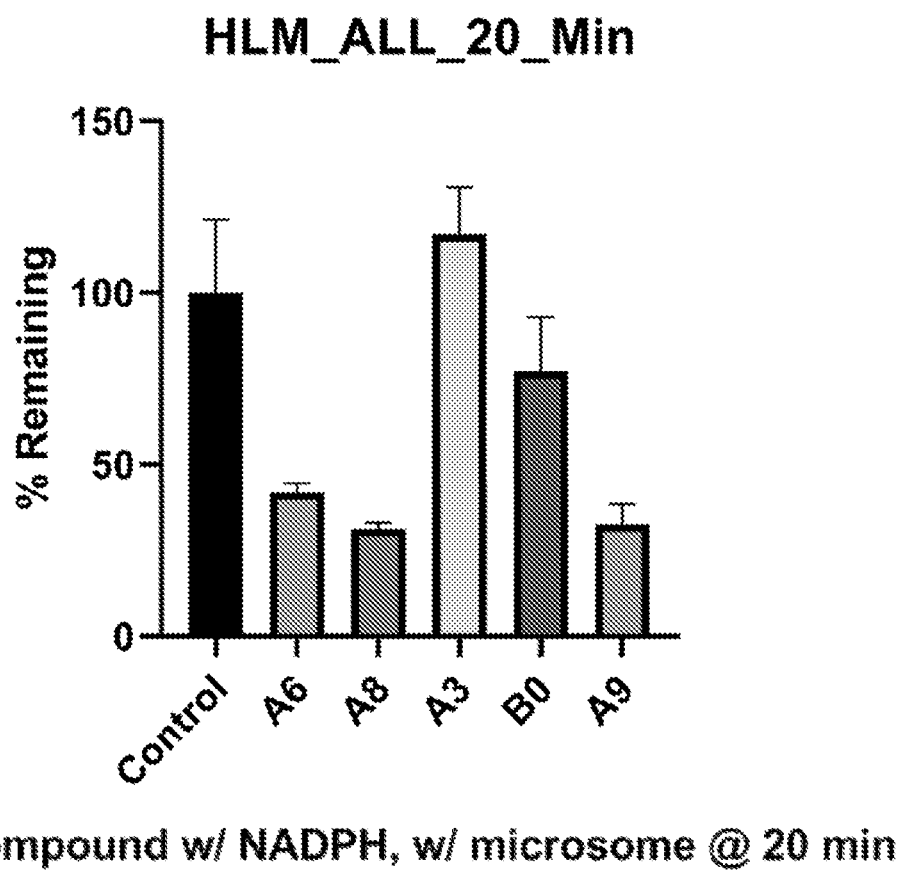
FIG. 3 shows the percent of the indicated compounds remaining after incubation with human liver microsomes for 20 minutes.

For example, in in vitro studies the compounds provided herein exhibit $IC_{50}$ values in the range of 60 to 2100 nM. The compounds also have been found to stabilize NRF2 expression relative to vehicle (DMSO) and increase the levels of NQO1, a well-known target gene of NRF2. When a carboxylic acid or bioisostere thereof is present at $R^3$, then the compounds disclosed herein show higher potency, relative to when a carboxylic acid or bioisostere is present at $R^4$. When an electron withdrawing group is present at $R^4$, then the compounds disclosed herein can exhibit improved pharmacokinetics, and in particular, improved metabolic stability and an improved ability to cross cell membranes. See, e.g., the Examples section, below, Table 1, Table 5, and FIGS. 2 and 3.

Therefore, one aspect of the disclosure relates to a method of inhibiting the KEAP-1/NRF2 interaction in a cell comprising contacting the cell with a compound disclosed herein (e.g., a compound of Formula (I), a compound listed in Table A, a compound listed in Table B, pharmaceutically acceptable salts of the foregoing, or combinations thereof), in an amount effective to inhibit the KEAP-1/NRF2 interaction. As used herein, the term "pharmaceutically acceptable" means that the referenced substance, such as a compound of the present disclosure or a composition containing the compound, or a particular excipient, is safe and suitable for administration to a subject or patient.

The compounds disclosed herein can inhibit the KEAP-1/NRF2 interaction in a cell by contacting the cell in vitro or in vivo. In some embodiments, the contacting occurs in vitro. In other embodiments, the contacting occurs in vivo. The compounds can contact the cell in vivo by administering the compound to a subject or patient in need of regulation of the KEAP-1/NRF2 interaction. As used herein, the terms "patient" and "subject" may be used interchangeably and mean animals, such as dogs, cats, cows, horses, and sheep (i.e., non-human animals) and humans. Particular patients are mammals (e.g., humans). Put another way, in various embodiments, the invention includes administering one or more compounds of the disclosure to a subject or patient, such as a human, in need thereof. In some of these embodiments, the patient suffers from a disease associated with deregulation of the KEAP-1/NRF2 interaction or from a disease or disorder wherein inhibition of the KEAP-1/NRF2 interaction would provide a benefit (e.g., COPD, multiple sclerosis, and diabetes) and/or to accelerate wound healing (e.g., chronic wound healing or diabetic wound healing).

Another aspect of the disclosure relates to a method of treating a clinical or preclinical disease or disorder associated with dysregulation of the KEAP1-NRF2 interaction comprising administering to a subject in need thereof a therapeutically effective amount of a compound disclosed herein (e.g., a compound of Formula (I), a compound listed in Table A, a compound listed in Table B, pharmaceutically acceptable salts of the foregoing, or combinations thereof). As used herein, the phrase "dysregulation of the KEAP1-NRF2 interaction" refers to an abnormality in the interaction of the KEAP1 and NRF2 protein, resulting excess NRF2 activity or NRF2 activation. As used herein, the term "therapeutically effective amount" refers to an amount of a compound or combination of therapeutically active compounds (e.g., a compound described herein, or a combination of compounds) that ameliorates, attenuates or eliminates one or more symptoms of a particular disease or condition (e.g., COPD, multiple sclerosis, or diabetes, or accelerates wound healing), or prevents or delays the onset of one of more symptoms of a particular disease or condition. As used herein the terms "treating", "treat" or "treatment" and the like include preventative (e.g., prophylactic) and palliative treatment. As used herein, the term "clinical disease or disorder" refers to a disease or disorder having recognizable clinical signs and symptoms. As used herein, the term "preclinical disease or disorder" refers to a period of a disease or disorder before the appearance of symptoms.

Examples of clinical diseases or disorders that can be treated by the compounds disclosed herein (e.g., a compound of Formula (I), a compound listed in Table A, a compound listed in Table B, pharmaceutically acceptable salts of the foregoing, or combinations thereof), can include, for example, Alport syndrome, amyotrophic lateral sclerosis, autosomal dominant polycystic kidney disease, bone disease, blood disease, chronic kidney disease, chronic obstructive pulmonary disease, connective tissue disease, dry eye macular degeneration, estrogen receptor-positive breast cancer, eye disease, focal segmental glomerulosclerosis, Friedreich ataxia, immunoglobulin A nephropathy, lung diseases (e.g., interstitial lung disease), multiple sclerosis, kidney disease, neurodegenerative disease, primary focal segmental glomerulosclerosis, psoriasis, pulmonary arterial hypertension, retinovascular disease, subarachnoid hemorrhage, type 1 diabetes, and type 2 diabetes mellitus. See Cuadrado, et al.;

Nature Rev. Drug Discov. 2019, https://www.ncbi.nlm.nih.gov/pubmed/30610225 (last accessed on Apr. 1, 2019).

Examples of preclinical disease or disorders that can be treated by the compounds disclosed herein (e.g., a compound of Formula (I), a compound listed in Table A, a compound listed in Table B, pharmaceutically acceptable salts of the foregoing, or combinations thereof), can include, for example, autoimmune diseases (e.g., rheumatoid arthritis, Sjogren syndrome, STING-dependent interferonopathies, systemic lupus erythematous, vitiligo); respiratory diseases (e.g., chronic obstructive pulmonary disease, chronic sarcoidosis, emphysema, hypersensitivity pneumonitis, idiopathic pulmonary fibrosis, pulmonary fibrosis); gastrointestinal diseases (e.g., hemochromatosis, hepatic fibrosis, primary biliary cholangitis and cirrhosis); metabolic diseases (e.g., insulin resistance, glomerulonephritis, nonalcoholic steatohepatitis, type 2 diabetes mellitus, vascular dysfunction); cardiovascular diseases (e.g., atherosclerosis, diabetic vascular disease, hypertension, myocardial ischemia-reperfusion injury, heart failure); neurodegenerative diseases (e.g., Alzheimer disease, Huntington disease, Friedrich ataxia, Parkinson disease); skin diseases (e.g., chronic/diabetic wound healing); and cancer chemoprevention. See Cuadrado, et al.; Nature Rev. Drug Discov. 2019, https://www.ncbi.nlm.nih.gov/pubmed/30610225 (last accessed on Apr. 1, 2019).

NRF2 activators are known to accelerate chronic or diabetic wound healing. Chronic skin wounds are those that have failed to progress through a timely and orderly process to produce anatomic and functional integrity at the wound site. See Lazarus et al., Wound Repair Regen. 1994 July; 2(3):165-70. Examples of chronic wounds include diabetic foot ulcers, venous ulcers, and pressure sores. See Sen et al., Wound Repair Regen. 2009 November-December; 17(6): 763-71. Older adults and diabetic patients are especially prone to developing these types of wounds. It is estimated that 25% of diabetic patients will develop a foot ulcer during their lifetime. Id. The costs associated with treating chronic wounds are estimated at $25 billion per year. Id. Given the aging of the American population and increases in age-related diabetes and obesity, treatment of chronic wounds will place an even larger burden on the US healthcare system. See Gosain et al., World Journal of Surgery. 2004; 28(3):321-6.

An important part of physiological wound healing is the inflammatory stage. After bleeding is under control ("hemostasis"), neutrophils, macrophages and lymphocytes sequentially migrate into the wound. Id. Neutrophils release reactive oxygen species and proteases to fight microbial infections. See Guo et al., J Dent Res. 2010; 89(3):219-29. Macrophages induce and clear apoptotic cells, and they stimulate keratinocytes, fibroblasts and angiogenesis, thus clearing the way for the proliferative phase of healing. See Mosser et al., Nature Reviews Immunology. 2008; 8(12): 958-69. However, an aberrant and prolonged inflammatory response is one of the most common contributors to the progression of chronic, non-healing wounds. See Guo et al., J Dent Res. 2010; 89(3):219-29; Khanna et al., PLoS One. 2010; 5(3):e9539. This is especially true in diabetic and/or obese patients, who, because of heightened inflammation (see González-Chávez et al., Cir Cir. 2011; 79(2):209-16; Wellen et al., Journal of Clinical Investigation. 2005; 115 (5):1111; Dandona et al., Trends in immunology. 2004; 25(1):4-7), are susceptible to experiencing non-healing wounds. See Rosner et al., APMIS: Acta Ppathologica, Microbiologica, et Immunologica Scandinavica. 1995; 103 (4):293-9; Apelqvist et al., Diabetes/Metabolism Research and Reviews. 2000; 16 Suppl 1:S75-83). The current arsenal of treatments for chronic wounds includes debridement (removal of dead tissues) (see Tallis A et al., Clinical therapeutics. 2013; 35(11):1805-20; Edwards et al., The Cochrane Database of Systematic Reviews. 2010(1): Cd003556; Lebrun et al., official publication of the Wound Healing Society [and] the European Tissue Repair Society. 2010; 18(5):433-8), numerous dressings (see Moura et al., Acta Biomaterialia. 2013; 9(7):7093-114; Raffetto et al., Phlebology/Venous Forum of the Royal Society of Medicine. 2014; 29(1 suppl):157-64), ultrasound (see Wollina et al., Indian Journal of Dermatology. 2011; 56(2):174-9; Ennis et al., Ostomy/Wound Management. 2005; 51(8):24-39), expensive cellular and recombinant growth factor receptor therapies that may increase the risk of cancer (see Lantis et a., Advances in Skin & Wound Care 2009; 22(4):167-71; Bennett et al., The British Journal of Surgery. 2003; 90(2): 133-46; Barrientos et al., official publication of the Wound Healing Society [and] the European Tissue Repair Society. 2008; 16(5):585-601), and antibiotics to prevent infection. See Dissemond et al., JDDG: Journal der Deutschen Dermatologischen Gesellschaft. 2014; 12(7):541-54; Daeschlein et al., International Wound Journal 2013; 10 Suppl 1:9-14.

Strikingly, pharmacologic therapies to accelerate healing of chronic wounds are sorely and conspicuously absent. Given the importance of inflammation to the progression of chronic wounds, targeting pathologic inflammation has been proposed as a means of combating chronic, non-healing wounds (see Menke et al., Clinics in Dermatology. 2007; 25(1):19-25), but there are currently no good ways of pharmacologically reducing inflammation in chronic wounds. See Guo et al., J Dent Res. 2010; 89(3):219-29. For example, both non-steroidal anti-inflammatory drugs (NSAIDs) (see Futagami et a., Laboratory Investigation; a Journal of Technical Methods and Pathology 2002; 82(11): 1503-13; Dvivedi et al., Indian Journal of Experimental Biology 1997; 35(11):1243-5; Jones et al., Nature medicine. 1999; 5(12):1418-23; Dong et al., The Journal of Trauma. 1993; 35(3):340-3) and systemic glucocorticoids (Franz et al., Current Problems in Surgery 2007; 44(11):691-763) have a deleterious effect on wound healing, although topically applied glucocorticoids may be beneficial, if monitored carefully. See Hofman et al., Journal of Wound Care. 2007; 16(5):227-30.

Thus, accelerating wound healing with pharmaceutical therapies is a major unmet medical need.

The anti-inflammatory transcription factor NRF2 plays an essential role in diabetic wound healing. Zhang and coworkers showed that the skin of diabetic patients showed higher oxidative stress, higher oxidative DNA damage, and higher compensatory NRF2 activation than the skin of normoglycemic patients. See Long et al., Diabetes. 2016; 65(3):780-93). A genetic knockout mouse study (NRF2−/−) showed that NRF2 is essential in diabetic wound healing. This is in contrast to wild-type mice, where NRF2 has been shown to be non-essential for normal wound healing (see Braun et al., Mol Cell Biol. 2002; 22(15):5492-505) Long et al. showed that systemic pre-treatment with electrophilic NRF2 activators decreased time to wound closure in a mouse model of Type 1 diabetes. See Long et al., Diabetes. 2016; 65(3):780-93. NRF2 is a plentiful target in the skin. It is highly expressed in wound keratinocytes (see Braun et al., Mol Cell Biol. 2002; 22(15):5492-505; Beyer et al., Cell Death Differ. 2007; 14(7):1250-4), which are epithelial skin cells that hyperproliferate and migrate to cover the wound with a new epidermis. It has recently been shown that lower concentrations of NRF2 and its target genes are found in wounds associated with type 2 diabetes and in skin tissue of diabetic patients (see Lee et al., Clin Exp Dermatol. 2015 March; 40(2):192-20), and that pro-inflammatory cytokines are increased. See Bitar et al. Adipocyte. 2012; 1(3):161-3; and Bitar et al., American Journal of Physiology Endocrinology and Metabolism 2011; 301(6):E1119-29. In supportive yet orthogonal work, Schmidt et al. have recently shown that non-thermal plasma, which is used to treat chronic wounds (see Kramer et al., Clinical Plasma Medicine. 2013; 1(1): 11-8), activates keratinocytes by inducing NRF2 and its target genes. See Schmidt et al., The Journal of Biological Chemistry 2015; 290(11):6731-50. Accordingly, pharmacologic activation of NRF2 by topically administering non-covalent small molecules can accelerate wound healing.

Thus, provided herein is a method of accelerating wound healing comprising administering to a subject in need thereof a therapeutically effective amount of a compound disclosed herein (e.g., a compound of Formula (I), a compound listed in Table A, a compound listed in Table B, pharmaceutically acceptable salts of the foregoing, or combinations thereof). In some cases, the wound is a chronic wound. As described herein, a "chronic wound" is a wound that has failed to progress through a timely and orderly process to produce anatomic and functional integrity at the wound site. Examples of chronic wounds include diabetic foot ulcers, venous ulcers, and pressure sores. In various cases, the wound is a diabetic wound (e.g., a diabetic foot ulcer). As described herein, "diabetic wound" refers to a wound on the lower limb of a patient having diabetes that is associated with neuropathy and/or peripheral arterial disease.

Use of a compound disclosed herein, such as a compound of Formula (I), a compound listed in Table A (e.g., A1-A5), a compound listed in Table B (e.g., B0-B52), a compound listed in Table C (e.g., C1-C10), or a pharmaceutically acceptable salt of the foregoing, to treat a condition resulting from dysregulation of the KEAP1-NRF2 interaction in a subject, as well as use of the compound in the preparation of a medicament for treating the condition, also are contemplated.

Further guidance for using compounds disclosed herein for inhibiting the KEAP1-NRF2 interaction, such as a compound Formula (I), a compound listed in Table A (e.g., A1-A5), a compound listed in Table B (e.g., B0-B52), a compound listed in Table C (e.g., C1-C10), or a pharmaceutically acceptable salt of the foregoing, can be found in the Examples section, below.

Pharmaceutical Formulations

Also provided herein are pharmaceutical formulations that include the compounds of the disclosure, and one or more pharmaceutically acceptable excipients. As used herein, the term "excipient" means any pharmaceutically acceptable additive, carrier, diluent, adjuvant, or other ingredient, other than the active pharmaceutical ingredient (API).

The compounds of the disclosure can be administered to a subject or patient in a therapeutically effective amount. The compounds can be administered alone or as part of a pharmaceutically acceptable composition or formulation. In addition, the compounds can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents.

Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

Assays

In Vitro Assays

The $IC_{50}$ of the compounds for inhibiting the interaction of a fluorescent NRF2 peptide and the Kelch domain of KEAP1 was determined using fluorescence anisotropy. See Inoyama et al., J. Biomol. Screening 2012, 17, 435-447. The results are shown in Tables 1-4, below.

Compounds A1, A4, and A5, containing acidic groups at both the $R^3$ and $R^4$ positions, have high binding affinities. Without intending to be bound by any particular theory, these compounds have high affinities due to their similarities to the native ETGE binding motif of NRF2. When only one acid is present, in either the $R^3$ or $R^4$ position, there is a drastic difference in binding affinity that is not structurally obvious. When the acidic group is in the $R^3$ position, potent binding observed. Replacing $R^4$ with an alkyl group, as in compounds A8 and A9, improved the pharmacokinetic properties of these molecules by increasing their lipophilicity. However, these modifications significantly diminished the binding affinity of these inhibitors. Replacing $R^4$ with a haloalkyl group, as in compound B0, resulted unexpectedly in a compound with nearly identical binding affinity as A1, yet with improved pharmacokinetic properties.

TABLE 1

| Compound | $R^4$ | $R^3$ | $R^2$ | $R^1$ | IC$_{50}$ (nM) |
|---|---|---|---|---|---|
| A1 | CH$_2$COOH | CH$_2$COOH | OMe | OMe | 63 |
| A2 | CH$_2$COOH | H | OMe | OMe | 1200 |
| A3 | CH$_2$COOH | CH$_3$ | OMe | OMe | 2000 |
| A4 | CH$_2$COOH | CH$_2$COOH | OH | OH | 530 |
| A5 | CH$_2$COOH | CH$_2$COOH | F | F | 350 |
| A6 | H | CH$_2$COOH | OMe | OMe | 212 |
| A7 | H | CH(CH$_3$)COOH | OMe | OMe | 2300 |
| A8 | CH$_3$ | CH$_2$COOH | OMe | OMe | 1100 |
| A9 | CD$_3$ | CH$_2$COOH | OMe | OMe | 1230 |
| B0 | CH$_2$CF$_3$ | CH$_2$COOH | OMe | OMe | 74 |

TABLE 2

| Compound | $R^4$ | $R^3$ | $R^2$ | $R^1$ | Y | Z | IC$_{50}$ (nM) |
|---|---|---|---|---|---|---|---|
| C1 | — | H | OMe | OMe | CH | CH$_2$ | 2900 |
| C2 | — | CH$_2$COOH | OMe | OMe | CH | CH$_2$ | 698 |
| C3 | — | CH(CH$_3$)COOH | OMe | OMe | CH | CH$_2$ | 167 |

TABLE 3

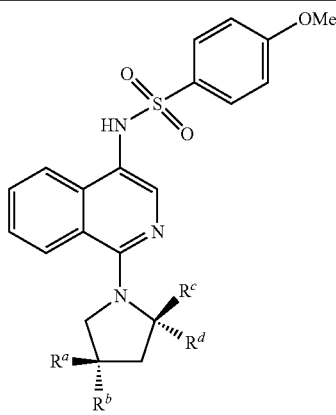

| Compound | $R^a$ | $R^b$ | $R^c$ | $R^d$ | IC$_{50}$ (nM) |
|---|---|---|---|---|---|
| C4 | Ph | H | H | COOH | 938 |
| C5 | H | H | COOH | H | >25000 |
| C6 | H | H | H | COOH | 5000 |
| C7 | Ph | H | H | H | >25000 |
| C8 | H | Ph | H | H | >25000 |

TABLE 4

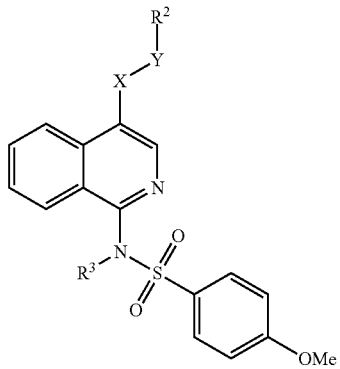

| Compound | $R^3$ | $R^2$ | X | Y | IC$_{50}$ (nM) |
|---|---|---|---|---|---|
| C9 | H | COOH | CH= | =CH | 9300 |
| C10 | CH$_2$COOH | COOH | CH= | =CH | 11000 |
| C11 | H | COOH | CH$_2$ | CH$_2$ | 6000 |
| C12 | CH$_2$COOH | COOH | CH$_2$ | CH$_2$ | 5600 |
| C13 | H | 4-MeOC$_6$H$_4$ | CH$_2$ | CH$_2$ | >25000 |
| C14 | CH$_2$COOH | 4-MeOC$_6$H$_4$ | CH$_2$ | CH$_2$ | >25000 |

NRF2 Target Gene Activation

Spontaneously immortalized human keratinocytes (HaCaT cell line) were grown in Dubecco's modified Eagle's medium (DMEM) with 10% fetal bovine serum and 1% antibiotics. Cells at 70-80% confluence were treated with compounds A1, A2, A3, A6, A7, A8, B0 for 6 h in the presence of complete medium to determine the stabilization of NRF2, and the protein expression levels of NADPH quinone oxidoreductase (NQO1), a well-known target gene of NRF2. Cells were lysed in a 20 mM Tris (pH 7.5) buffer containing 150 mM NaCl, 1 mM EDTA, 1 mM EGTA, 1% Triton X-100, 2.5 mM sodium pyrophosphate, 1 mM Na3VO4, 5 mM β-glycerophosphate, and 1 µg/mL leupeptin. Equal amount of protein (~40 µg) was separated on a 10% SDS-PAGE, blotted on the membrane, and probed with antiNRF2, or anti-NQO1 antibody. As shown in the Western Blot provided in FIG. 2, compounds A6 and B0 were found to stabilize NRF2 expression, relative to vehicle (DMSO) control. CDDO is a positive control compound that activates NRF2 through an electrophilic mechanism. Compounds A6 and B0 also increase the levels of NQO1.

Microsomal Stability Study

LC-MS grade acetonitrile (MeCN), methanol (MeOH), formic acid, and biology grade DMSO were purchased from Fisher Scientific (Pittsburgh, Pa.). LC-MS grade water was generated using a Barnstead Nanopure Diamond water system (Thermo Scientific, Pittsburgh, Pa.). All other reagents, if not specified, were purchased from Sigma-Aldrich (Saint Louis, Mo.). Pooled human liver microsomes and mouse liver microsomes were purchased from Sekisui XenoTech (Kansas City, Kans.). Preparation of Standard. The initial stock solutions of test compounds were prepared in DMSO at 10 mM, and then diluted with MeOH to 200 µM before use. All stock solutions were stored at −20° C. Liver microsomes were aliquoted upon arrival and stored at −80° C. Samples were analyzed on a Shimadzu 8040 triple-quadrupole mass spectrometer (Shimadzu, Addison, Ill.) equipped with electrospray ion source and Shimadzu Nexera XR UHPLC system. Mobile phase A contained water with 0.025% (v/v) FA, and mobile phase B consisted of MeCN with 0.1% (v/v) FA. Five microliters of sample was injected. Study compounds were eluted on a Kinetex C18 column (3.0×50 mm, 2.6 µm; Phenomenex, Torrance, Calif.) at 500 µL/min using a gradient program: mobile phase B started and maintained at 15% for 1 min, then increased to 95% in 4 min. Nebulizing gas flow and drying gas flow were set to 2 and 15 L/min. DL temperature, heat block temperature, and ion spray voltage were maintained at 300° C., 450° C. and 4500 V, respectively.

Compounds of the disclosure (A3, A6, A8, A9, B0) were subjected to human liver microsomes in buffer for a period of 20 min to ascertain their metabolic stability. It was observed that compounds A6, A8, and A9 were degraded substantially, while compound A3 was significantly more metabolically stable. Incorporation of an electron withdrawing group at $R^4$, such as the 2,2,2-trifluoroethyl group of compound B0, yielded both metabolic stability and high affinity. See FIG. 3.

Log $D_{7.4}$ The log $D_{7.4}$ of compounds of the disclosure (A1, A2, A3, A6, A8, B0) was determined in HEPES buffer at pH 7.4 by preparing a 10 mM stock solution by completely dissolving test compound in DMSO. This solution was diluted to nine known concentration solutions (1200, 800, 400, 120, 80, 40, 12, 8, and 4 µM) in MeCN. Each solution was analyzed by HPLC, and a calibration curve was plotted using the peak areas from the standard concentrations. 20 µL of the 10 mM DMSO stock solution of each compound was partitioned between 390 mL of buffer (200 mM HEPES, 150 mM NaCl, pH 7.4) and 390 mL of 1-octanol. The mixture was mixed for 1 h. Each layer was injected separately onto a Shimadzu LC-20AB HPLC system (Solvent system: gradient from 15% MeCN/85% H$_2$O to 95% MeCN/5% H$_2$O (+0.1% formic acid) over 13 min; Column, Shimadzu C18, 50 µm, 50×4.6 mm; UV, 254 nm). The equilibrium solubility in the buffer layer and the 1-octanol layer of test compounds was determined by quantifying the concentration of test solutions against the calibration curve. Experiments were run in triplicate, and results were tabulated and reported as mean. As shown in Table 5, below, it was found that all of the compounds analyzed possessed a log D between −2 and 0 except for compound B0 bearing the 2,2,2-trifluoroethyl group. Thus, including an electron withdrawing group at position $R^4$ results in improved pharmacokinetics, such as an improved ability to cross cell membranes.

TABLE 5

| Compound | logD |
|---|---|
| A1 | −1.5 |
| A6 | −1.6 |
| A2 | −0.5 |
| A8 | 0.0 |
| A3 | 0.0 |
| B0 | 0.5 |

Assay

Test compounds' ability to inhibit the KEAP1-NRF2 interaction were assayed using the Kelch domain of KEAP1 and a fluorescein-labeled 9-mer peptide containing the ETGE motif of the Neh2 domain of NRF2. The experiments were performed in triplicate, and sigmoidal concentration-response curves were fitted to the data using Graphpad Prism 6.1 software.

Synthetic Examples

General

All starting materials and solvents were purchased from Sigma-Aldrich, Acros Organics, Fischer Scientific, ArkPharm, TCI America, or Matrix Scientific and used without further purification. Compound identities were confirmed by $^1$H and $^{13}$C NMR and HRMS. $^1$H and $^{13}$C NMR spectra were recorded on a Bruker 400 MHz spectrometer using the corresponding residual solvent peak (CDCl$_3$, 1 H δ=7.26 and 13C δ=77.2; CD$_3$COCD$_3$, 1 H δ=2.05 and 13C=29.2; CD$_3$OD, 1H δ=3.31 and 13C=49.2; CD$_3$CN, 1H δ=1.96 and 13C δ=118.3; DMSO-d$_6$, 1 H δ=2.50 and 13C δ=39.5)) as an internal standard. HRMS spectra were recorded on a Shimadzu LCMS-IT-TOF, and the molecular weight of the compounds was within 0.05% of calculated values. Purity of each of the final, tested compounds was determined by HPLC on a Shimadzu LC-20AB ((Solvent system: gradient from 15% MeCN/85% H2O to 95% MeCN/5% H2O (+0.1% formic acid) over 13 min; Column: Shimadzu C18, 50 µm, 50×4.6 mm) and was ≥95% (UV, 254 nm). Flash chromatography was performed using silica gel (230-400 mesh). All reactions were monitored by thin-layer chromatography (TLC) on silica gel GHLF plates (250 µm, Macherey-Nagel, Inc., Bethlehem, Pa.).

Example 1. Synthesis of 2,2'-(isoquinoline-1,4-diyl-bis(((4-methoxyphenyl)sulfonyl) azanediyl))diacetate Preparation of Boc-4-pyridin-4-yl-piperidine (2)

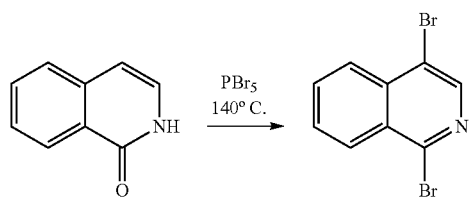 [SMILES: O=c1[nH]ccc2ccccc12 ; Brc1cnc(Br)c2ccccc12]

1,4-dibromoisoquinoline (1)

In a 50 mL round-bottom flask, isocarbostyril (0.50 g, 3.4 mmol) and phosphorus pentabromide (2.7 g, 9.8 mmol) were heated at 140-145° C. for 10 min. The solid melted and lightened in color. The liquid solidified, and the reaction was stirred for an additional 10 min. On completion, the reaction mixture was cooled to room temperature, and ice/H₂O (10 mL) was poured into the flask. The solid precipitate was collected by filtration, washed with H2O (2×50 mL), and dried under vacuum to obtain 860 mg (89% yield) of (1) as a buff-colored solid.

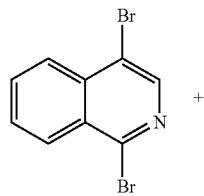

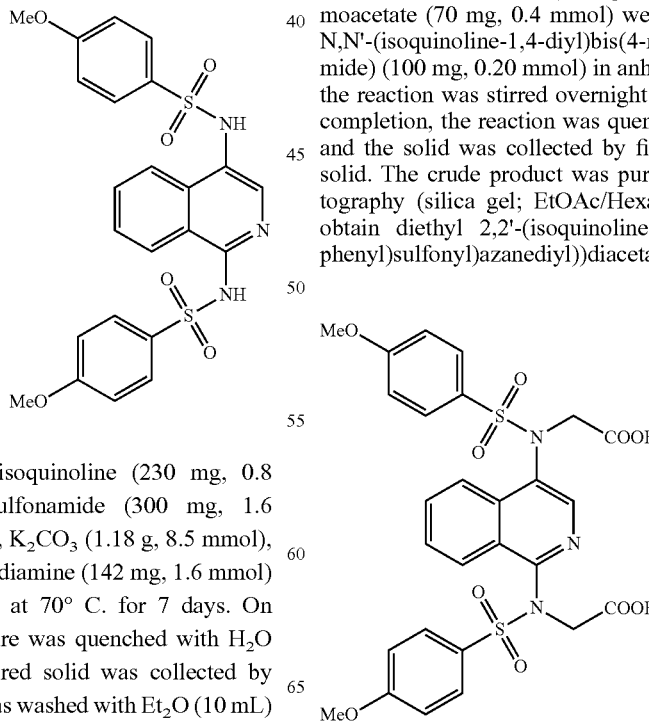

A solution of 1,4-dibromoisoquinoline (230 mg, 0.8 mmol), 4-methoxybenzene sulfonamide (300 mg, 1.6 mmol), CuI (60 mg, 0.3 mmol), K₂CO₃ (1.18 g, 8.5 mmol), and N¹,N²-dimethylethane-1,2-diamine (142 mg, 1.6 mmol) in MeCN (6 mL) was heated at 70° C. for 7 days. On completion, the reaction mixture was quenched with H₂O (20 mL), and the yellow-colored solid was collected by filtration. The collected solid was washed with Et₂O (10 mL) and dried to yield the title compound.

Example 2. Synthesis of 2,2'-(isoquinoline-1,4-diyl-bis(((4-methoxyphenyl)sulfonyl) azanediyl))diacetate

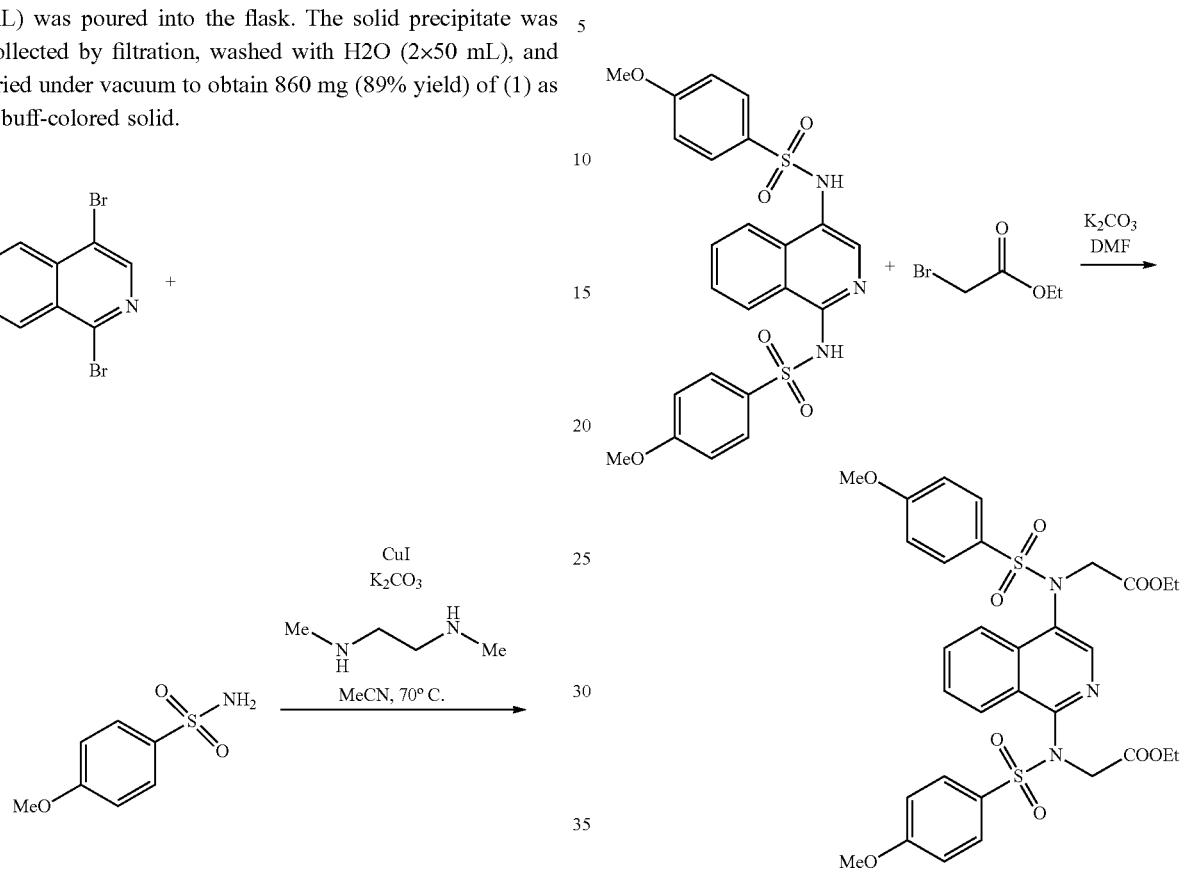

Potassium carbonate (83 mg, 0.17 mmol) and ethyl bromoacetate (70 mg, 0.4 mmol) were added to a solution of N,N'-(isoquinoline-1,4-diyl)bis(4-methoxybenzenesulfonamide) (100 mg, 0.20 mmol) in anhydrous DMF (2 mL), and the reaction was stirred overnight at room temperature. On completion, the reaction was quenched with H₂O (10 mL), and the solid was collected by filtration to yield a brown solid. The crude product was purified by column chromatography (silica gel; EtOAc/Hexanes, 0:100 to 50:50) to obtain diethyl 2,2'-(isoquinoline-1,4-diylbis(((4-methoxyphenyl)sulfonyl)azanediyl))diacetate.

-continued

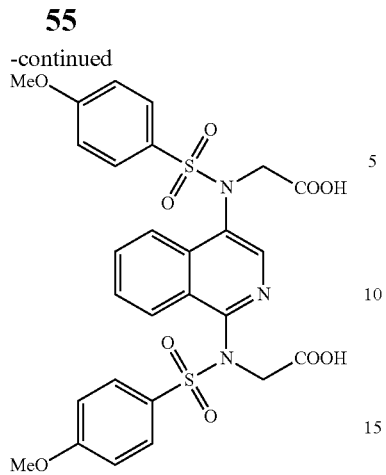

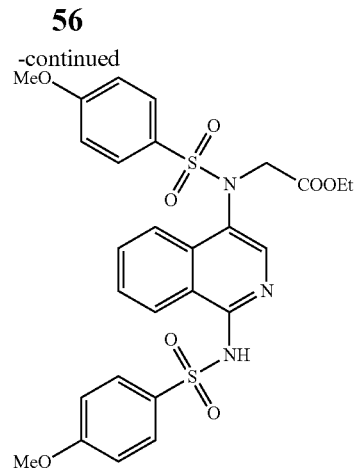

2,2'-(isoquinoline-1,4-diylbis(((4-methoxyphenyl)sulfonyl)azanediyl))diacetic acid In a 20 mL screw cap vial diethyl 2,2'-(isoquinoline-1,4-diylbis(((4-methoxyphenyl)sulfonyl)azanediyl))diacetate (42 mg, 0.06 mmol) was dissolved in MeOH (2 mL) and 15% NaOH (0.5 mL) was added. The resulting solution was allowed to reflux for 1.5 h. On completion, the reaction mixture was cooled, and the organic portion was evaporated and diluted with H$_2$O (10 mL). The solid was removed by filtration, and the filtrate was acidified with HCl (2 N, to pH 4) and extracted with EtOAc (2×5 mL). The combined organic portions were washed with H$_2$O (2×10 mL), dried (Na$_2$SO$_4$), and evaporated to yield a yellow solid as crude product. The crude product was further purified by preparative HPLC (C18, 20-95% MeCN/H$_2$O+0.1% formic acid) to yield the title compound.

Example 3. Synthesis of N-(1-((4-methoxyphenyl)sulfonamido)isoquinolin-4-yl)-N-((4-methoxyphenyl)sulfonyl)glycine ethyl N-(1-((4-methoxyphenyl)sulfonamido)isoquinolin-4-yl)-N-((4-methoxyphenyl)sulfonyl) glycinate (5)

In a 4 mL screw cap vial N,N'-(isoquinoline-1,4-diyl)bis(4-methoxybenzenesulfonamide) (200 mg, 0.40 mmol), and K$_2$CO$_3$ (66 mg, 0.48 mmol), were dissolved in DMF and cooled to 0° C. and ethylbromoacetate (48 μL, 0.44 mmol) was added to the cold solution. The reaction was stirred for 6 hours maintaining 0° C. the entire time. After 6 hours, the reaction was diluted with water and extracted with ethyl acetate (3×10 mL) the combined organics were washed with water (2×20 mL), brine (2×20 mL), dried over Na$_2$SO$_4$, and concentrated under reduced pressure to yield an orange oil. The crude product was purified by column chromatography (silica gel; EtOAc/Hexanes, 0:100 to 40:60) afford 59.6 mg (25% yield) of (5) as an off yellow solid.

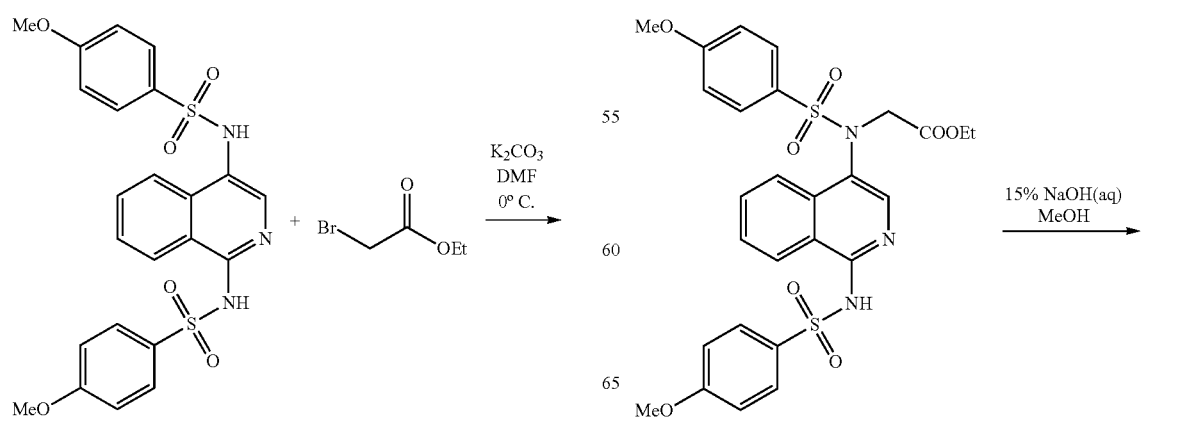

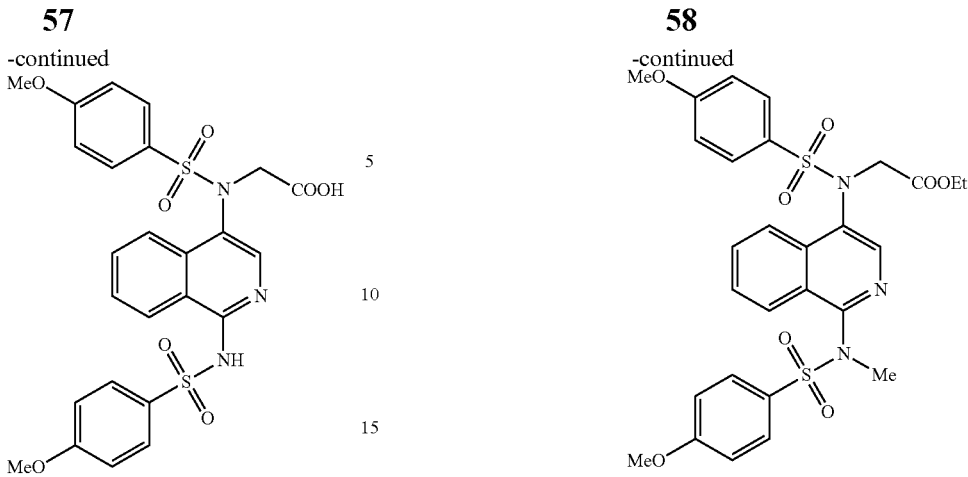

N-(1-((4-methoxyphenyl)sulfonamido)isoquinolin-4-yl)-N-((4-methoxyphenyl)sulfonyl)glycine (6)

In a 20 mL screw cap vial ethyl N-(1-((4-methoxyphenyl)sulfonamido)isoquinolin-4-yl)-N-((4-methoxyphenyl)sulfonyl)glycinate (5) (59.6 mg, 0.1 mmol) was dissolved in methanol (2 mL) and 15% NaOH$_{(aq)}$ (0.25 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na$_2$SO$_4$, and concentrated to yield an off white solid. Crude product was purified by HPLC (C18; MeCN/H$_2$O 60%:40%, isocratic) to yield the title compound.

Example 4. Synthesis of N-(1-((4-methoxy-N-methylphenyl)sulfonamido)isoquinolin-4-yl)-N-((4-methoxyphenyl)sulfonyl)glycine ethyl N-(1-((4-methoxy-N-methylphenyl)sulfonamido)isoquinolin-4-yl)-N-((4-methoxyphenyl)sulfonyl)glycinate (7)

In a screw cap vial ethyl N-(1-((4-methoxyphenyl)sulfonamido)isoquinolin-4-yl)-N-((4-methoxyphenyl)sulfonyl)glycinate (36 mg, 0.06 mmol) and potassium carbonate (12 mg, 0.09 mmol) were dissolved in DMF and iodomethane (4 μL, 0.7 mmol) was added. The reaction was diluted with water and extracted with ethyl acetate (3×10 mL) the combined organics were washed with water (2×20 mL), brine (2×20 mL), dried over Na$_2$SO$_4$, and concentrated under reduced pressure to yield an orange oil. The crude product was purified by column chromatography (silica gel; EtOAc/Hexanes, 0:100 to 30:70) afford 23 mg (62% yield) of (7) as an off white solid.

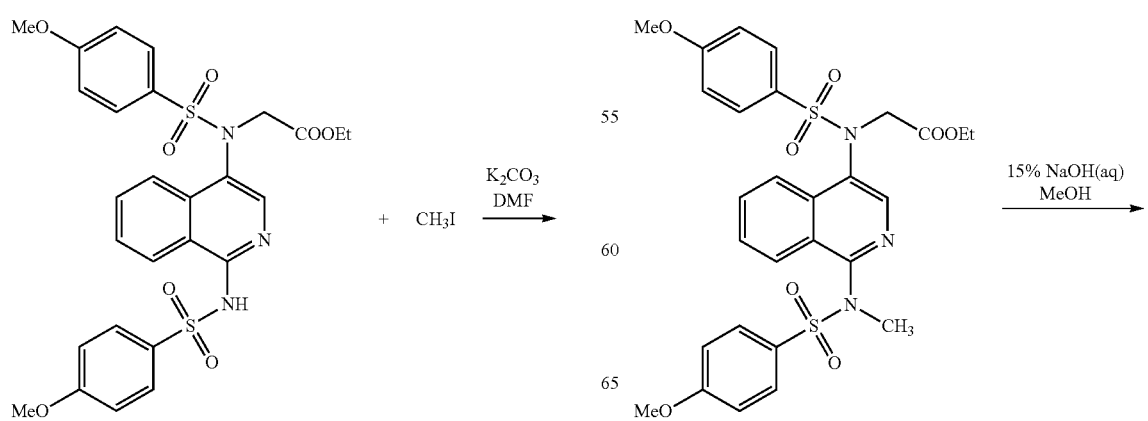

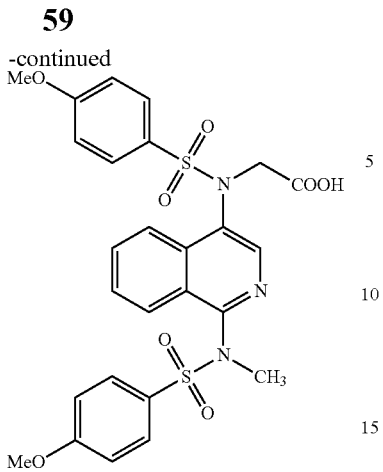

N-(1-((4-methoxy-N-methylphenyl)sulfonamido) isoquinolin-4-yl)-N-((4-methoxyphenyl) sulfonyl) glycine (8)

In a 20 mL screw cap vial ethyl N-(1-((4-methoxy-N-methylphenyl)sulfonamido)isoquinolin-4-yl)-N-((4-methoxyphenyl)sulfonyl)glycinate (7) (23 mg, 0.04 mmol) was dissolved in methanol (2 mL) and 15% $NaOH_{(aq)}$ (0.25 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over $Na_2SO_4$, and concentrated to yield an off white solid. Crude product was purified by HPLC (C18; MeCN/$H_2O$ 60%:40%, isocratic) to yield the title compound.

Example 5. Synthesis of 2,2'-(isoquinoline-1,4-diyl-bis(((4-hydroxyphenyl)sulfonyl) azanediyl))diacetic acid

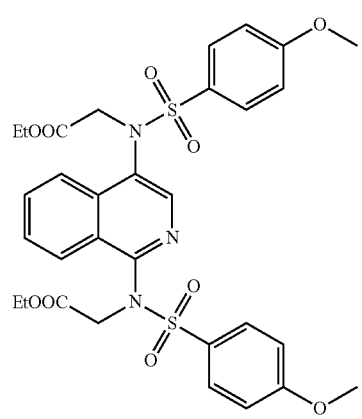

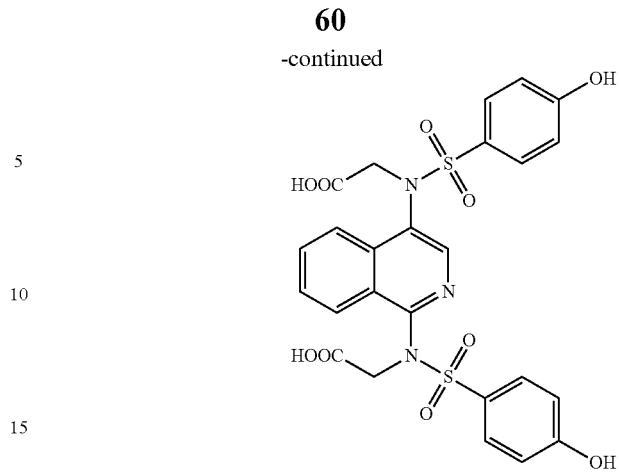

2,2'-(isoquinoline-1,4-diylbis(((4-hydroxyphenyl) sulfonyl)azanediyl))diacetic acid (9)

A solution of diethyl 2,2'-(isoquinoline-1,4-diylbis(((4-methoxyphenyl)sulfonyl)azanediyl))diacetate (3) (0.100 g, 0.148 mmol, 1 eq) in $CH_2Cl_2$ (0.5 mL) was stirred at −78° C. for ½ h. Once cooled, 1 M $BBr_3$ in $CH_2Cl_2$ (0.1 mL) was added dropwise to the flask and reaction mixture allowed to warm to room temperature and stir for 24 h. Upon completion, EtOH (5 mL) was added to quench reaction and diluted with EtOAc (10 mL); washed with $H_2O$ (20 mL) and brine (20 mL). Crude mixture was purified by semi-prep HPLC column (Solvent System MeCN:H2O with 0.1% formic acid; 0-35 min, 30% MeCN; 35-36 min, 30-95% MeCN; 36-43 min, 95% MeCN; 43-45 min, 95-30% MeCN; 45-50 min, 30% MeCN) to yield the title compound.

Example 6. Synthesis of N,N'-(isoquinoline-1,4-diyl)bis(4-fluorobenzenesulfonamide)

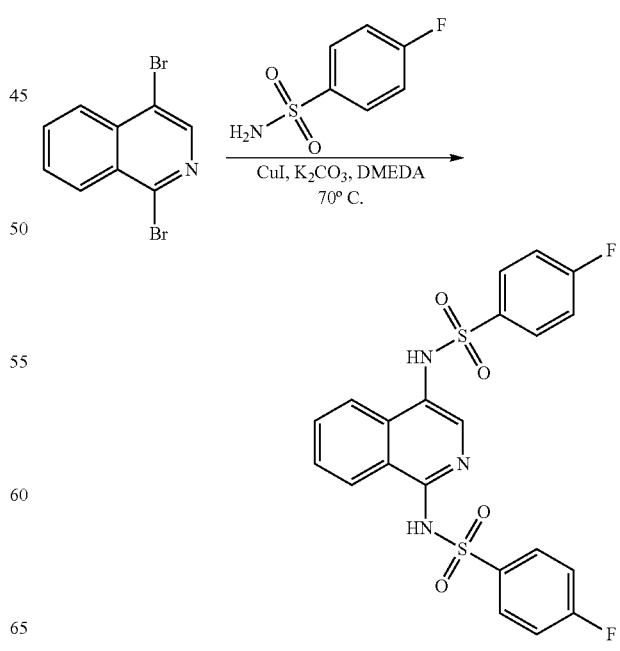

N,N'-(isoquinoline-1,4-diyl)bis(4-fluorobenzenesulfonamide) (10)

A round bottom flask was flame dried and back-filled with Ar. Solids were weighed out (1,4 dibromo isoquinoline (1) (0.500 g, 1.74 mmol), 4-fluorobenzenesulfonamide (0.609 g, 3.48 mmol), CuI (0.132 g, 0.696 mmol), K₂CO₃ (2.52 g, 18.27 mmol)) and added to flask. The flask was purged with Ar. MeCN (5 mL) and DMEDA (0.038 mL, 3.48 mmol) were then added to start reaction. Reaction was run at 70° C. for 7 days. Upon completion, reaction was quenched by pouring mixture into ice/water (100 mL). EtOAc (3×50 mL) was used to extract the aqueous mixture. Combined organic layers were washed with water (50 mL) and brine (50 mL); dried (Na₂SO₄); and evaporated to yield a crude product which, upon recrystallization using toluene (20 mL), yielded the title compound.

Example 7. Synthesis of 2,2'-(isoquinoline-1,4-diyl-bis(((4-fluorophenyl)sulfonyl) azanediyl))diacetic acid

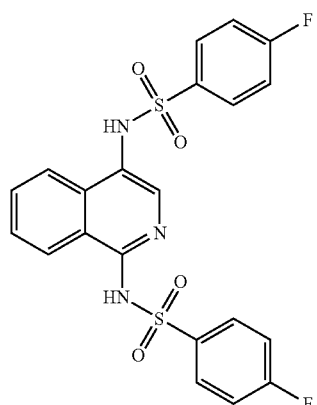

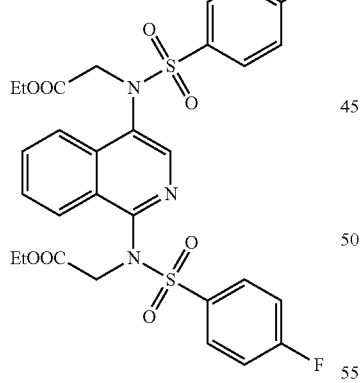

diethyl 2,2'-(isoquinoline-1,4-diylbis(((4-fluorophenyl)sulfonyl)azanediyl))diacetate (11)

N,N'-(isoquinoline-1,4-diyl)bis(4-fluorobenzenesulfonamide) (10) was added to a flask, along with K₂CO₃ (0.117 g, 0.846 mmol) and 18-crown-6 ether (0.019 g, 0.074 mmol). DMF (1.5 mL) was added; mixture was allowed to stir at room temperature for ½ hr. Ethyl bromoacetate (0.135 mL, 1.18 mmol) was added to mixture and allowed to stir for 24 h at room temperature. Upon completion, mixture was diluted with EtOAc (40 mL) and washed with H₂O (30 mL) and brine (30 mL); dried (Na₂SO₄); and evaporated to yield a crude product. Crude product was dissolved in CH₂Cl₂ (1 mL) and purified by column chromatography (silica gel; EtOAc/Hexanes, 10:90 to 100:0). Fractions were combined and concentrated in vacuo to yield 0.077 g (32%) of (11) as a buff-colored solid.

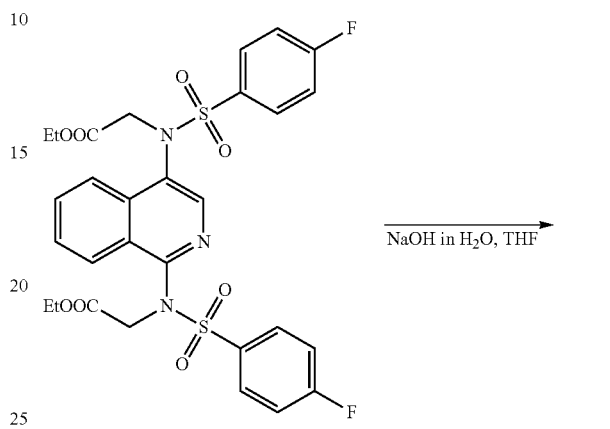

2,2'-(isoquinoline-1,4-diylbis(((4-fluorophenyl)sulfonyl)azanediyl))diacetic acid (12)

Diethyl 2,2'-(isoquinoline-1,4-diylbis(((4-fluorophenyl)sulfonyl)azanediyl))diacetate (11) (0.072 g, 0.111 mmol, 1 eq) was added to a flask; dissolved in THF (0.5 mL). 20% NaOH solution (0.05 mL) was added and reaction mixture was stirred at room temperature for 18 h. Upon completion, mixture was diluted with H₂O (10 mL) and pH adjusted using HCl (2N). Aqueous mixture was extracted with EtOAc (3×10 mL) and washed with brine (10 mL); dried (Na₂SO₄); and evaporated to yield a crude product. Crude product was purified using a semi-prep HPLC column (Solvent System MeCN:H₂O with 0.1% formic acid; 0-17.5 min, 50% MeCN; 17.5-19.5 min, 50-95% MeCN; 19.5-26.5 min, 95% MeCN; 26.5-29 min, 95-50% MeCN; 29-36 min, 50% MeCN). Combined fractions were concentrated by evaporating MeCN and frozen. Product was then subjected to lyophilization to yield the title compound.

Example 8. Synthesis of N-(4-((4-methoxyphenyl)sulfonamido)isoquinolin-1-yl)-N-((4-methoxyphenyl)sulfonyl)glycine

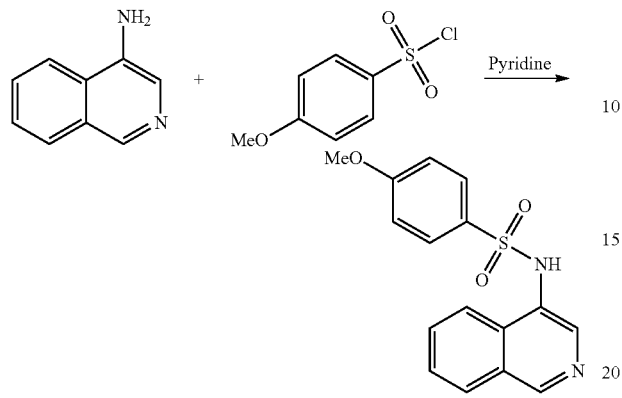

N-(isoquinolin-4-yl)-4-methoxybenzenesulfonamide (13)

In a single-necked round-bottomed flask isoquinoline-4-amine (1.50 g, 10.4 mmol) and 4-methoxybenzenesulfonyl chloride (2.47 g, 11.96 mmol) were dissolved in anhydrous pyridine (18 mL) and stirred at room temperature overnight. Upon completion of the reaction determined by TLC, the reaction was diluted with water (50 mL) and extracted with EtOAc (25 mL). The layers were separated, and the aqueous layer was extracted with EtOAc (2×25 mL). The combined organics were washed with water (50 mL), brine (2×50 mL), dried over Na₂SO₄, and concentrated under reduced pressure to a brown oil. Toluene (50 mL) was added to the oil and removed under reduced pressure to yield an orange solid. The crude product was purified by recrystallization from toluene to yield 2.50 grams (77% yield) of (13) as an orange solid.

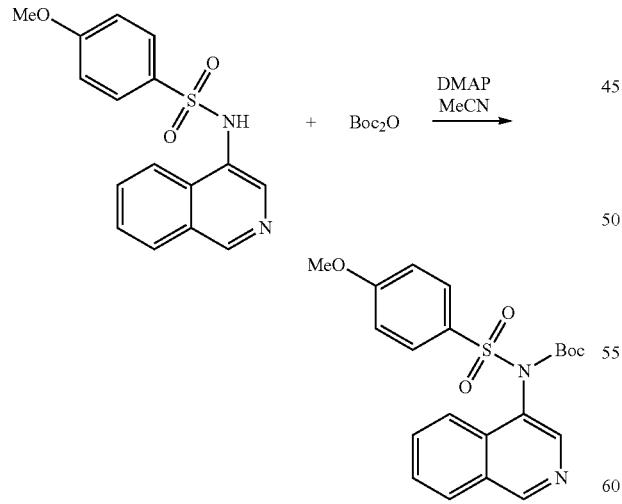

tert-butyl isoquinolin-4-yl((4-methoxyphenyl)sulfonyl)carbamate (14)

In a single necked flask N-(isoquinolin-4-yl)-4-methoxybenzenesulfonamide (13) (2.45 g, 7.79 mmol) and DMAP (0.12 g, 0.98 mmol) were dissolved in acetonitrile (105 mL) and a solution of Boc₂O (2.6 g, 11.9 mmol) in acetonitrile (20 mL) was added in one portion and the resulting mixture was stirred at room temperature for 2 hours. The reaction mixture was concentrated under reduced pressure to an orange oil. The crude product mixture was purified by column chromatography (silica gel; EtOAc/Hexanes 0:100 to 50:50) pure fractions were combined to yield 2.1437 grams (66% yield) of (14) as a yellow solid.

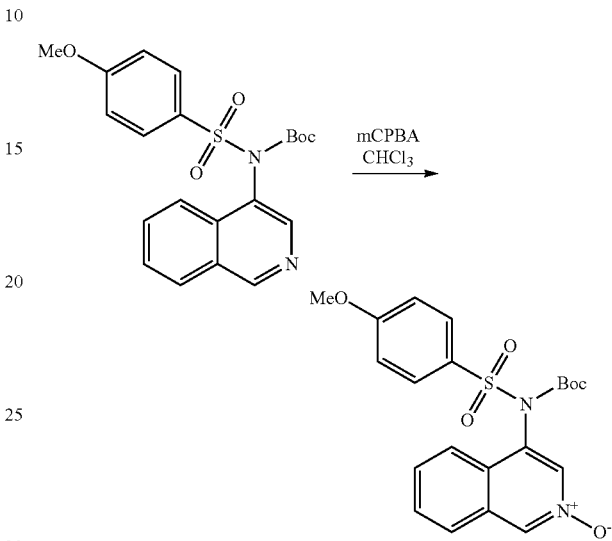

4-((N-(tert-butoxycarbonyl)-4-methoxyphenyl)sulfonamido)isoquinoline 2-oxide (15)

In a single neck flask tert-butyl isoquinolin-4-yl((4-methoxyphenyl)sulfonyl) carbamate (14) (2.0 g, 4.8 mmol) was dissolved in chloroform (15 mL) and a solution of mCPBA (3.33 g, 19.3 mmol) in chloroform (45 mL) was added dropwise. After the addition was complete the reaction was stirred at room temperature for 18 hours. After the reaction was complete 1 N NaOH (25 mL) was added to the reaction and stirred for 10 minutes. The layers were separated and the organic layer was washed again with 1 N NaOH (25 mL), dried over MgSO₄ and concentrated under reduced pressure to yield an off-white solid. The crude product was purified by column chromatography (silica gel; MeOH/EtOAc 0:100 to 10:90) pure fractions were combined to yield 1.63 g (78% yield) of (15) as an off-white solid.

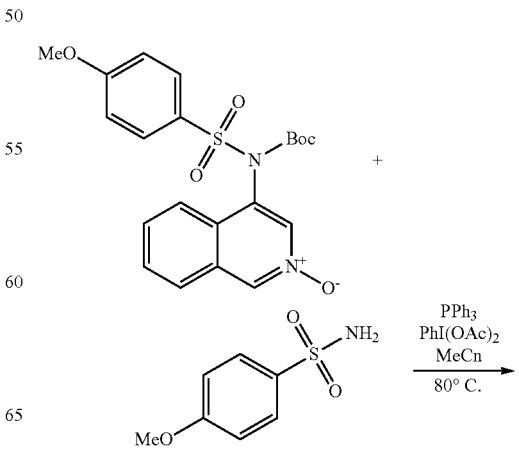

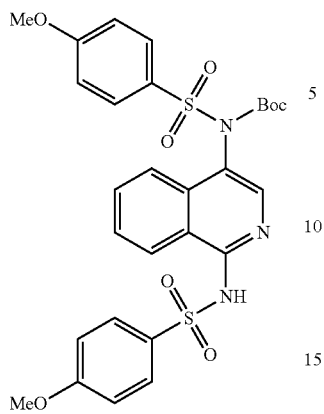

tert-butyl (1-((4-methoxyphenyl)sulfonamido)isoquinolin-4-yl)((4-methoxyphenyl)sulfonyl) carbamate (16)

In a flame-dried single necked round-bottomed flask 4-((N-(tert-butoxycarbonyl)-4-methoxyphenyl)sulfonamido)isoquinoline 2-oxide (15) (0.50 g, 1.16 mmol), 4-methoxybenzenesulfonamide (0.44 g, 2.3 mmol), diacetoxy iodobenzene (0.75 g, 2.3 mmol), and triphenylphosphine (0.61 g, 2.3 mmol) were placed. The flask was purged with argon and acetonitrile (2.3 mL) was added. The resulting suspension was headed to 80° C. After 18 hours the flask was removed from heat and allowed to cool to room temperature. H$_2$O (20 mL) was added to the flask and the mixture was extracted with EtOAc (2×25 mL). The combined organic layers were washed with brine (25 mL) and dried over Na$_2$SO$_4$. Solvent was removed under reduced pressure to yield an orange oil. The crude material was purified by column chromatography silica gel; EtOAc/Hexanes 0:100 to 50:50) which yielded a mixture of the product and residual 4-methoxybenzenesulfonamide. Pure product was obtained by a second column (silica el; EtOAc/DCM 0:100 to 10:90) to yield 0.26 g (37% yield) of (16) as an off white solid.

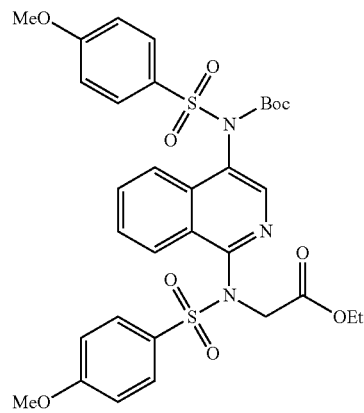

ethyl N-(4-((N-(tert-butoxycarbonyl)-4-methoxyphenyl)sulfonamido)isoquinolin-1-yl)-N-((4-methoxyphenyl)sulfonyl)glycinate (17)

In a 4 mL screw cap vial tert-butyl (1-((4-methoxyphenyl)sulfonamido)isoquinolin-4-yl)((4-methoxyphenyl)sulfonyl) carbamate (16) (100 mg, 0.17 mmol) and potassium carbonate (58 mg, 0.42 mmol) were placed and acetonitrile (1.3 mL) was added. Ethyl bromoacetate (37 μL, 0.33 mmol) was added to the stirred suspension and the resulting mixture was allowed to stir for 36 hours. Upon complete consumption of starting material as determined by LC-MS the reaction was diluted with EtOAc) (2 mL) and filtered through a small pad of celite, washing with EtOAc. The filtrate was concentrated under reduced pressure to yield an orange oil. The crude product was purified by column chromatography (silica gel; EtOAc/Hexanes 0:100 to 30:70). Pure fractions were combined and concentrated under reduced pressure to yield 75 mg (66% yield) of (17) as a light yellow solid.

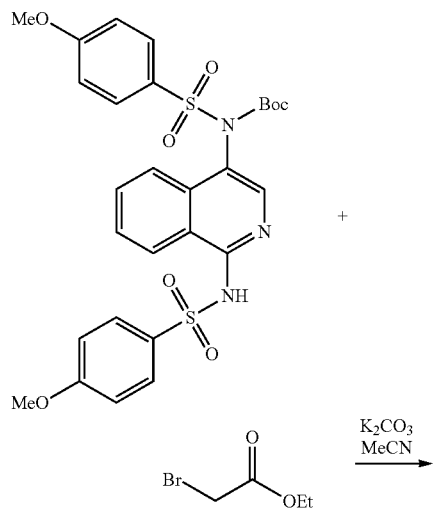

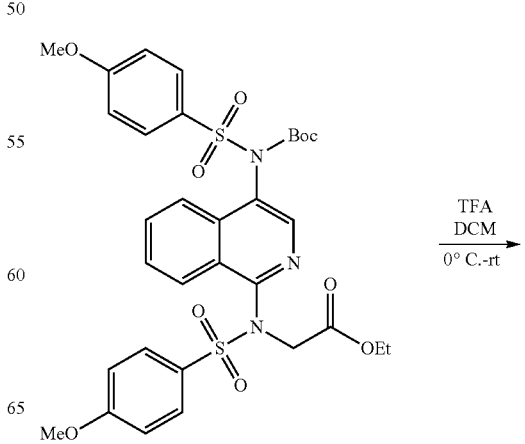

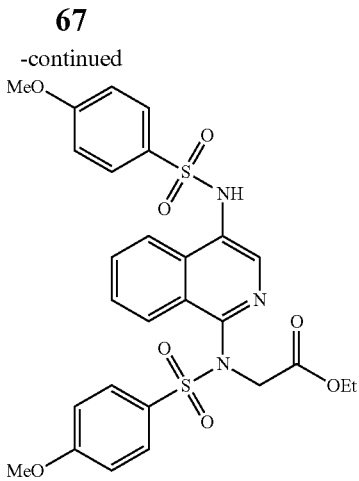

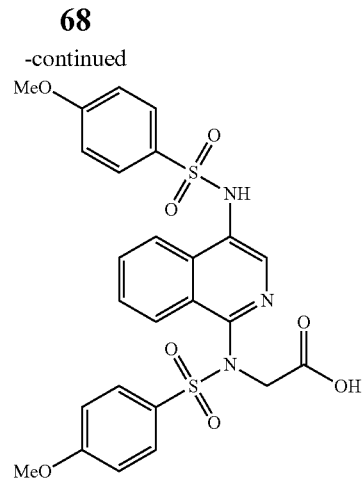

Ethyl N-(4-((4-methoxyphenyl)sulfonamido)isoquinolin-1-yl)-N-((4-methoxyphenyl)sulfonyl)glycinate (18)

In a 20 mL screw cap vial, ethyl N-(4-((N-(tert-butoxycarbonyl)-4-methoxyphenyl)sulfonamido)isoquinolin-1-yl)-N-((4-methoxyphenyl)sulfonyl)glycinate (17) (75 mg, 0.11 mmol) was dissolved in dichloromethane (3 mL) and the resulting solution was cooled to 0° C. in an ice/water bath. Once cooled, trifluoroacetic acid (0.50 mL, 6.5 mmol) was added to the isoquinoline solution and the reaction was allowed to slowly warm to room temperature. After 4 hours the reaction was quenched with sat. aq. NaHCO$_3$ (3 mL) and the resulting mixture was allowed to stir for 30 minutes. The layers were separated and the aqeuous later was extracted with DCM (5 mL) the combined organics were washed with brine (5 mL) and dried over MgSO$_4$ to yield 62 mg (97% yield) of (18) as a light yellow solid. Product did not require purification.

N-(4-((4-methoxyphenyl)sulfonamido)isoquinolin-1-yl)-N-((4-methoxyphenyl)sulfonyl)glycine (19)

In a 20 mL screw cap vial, ethyl N-(4-((4-methoxyphenyl)sulfonamido)isoquinolin-1-yl)-N-((4-methoxyphenyl)sulfonyl)glycinate (18) (50 mg, 0.085 mmol) was dissolved in MeOH (3 mL) and 15% NaOH in H$_2$O (wt/wt) was added to the solution. The reaction was stirred for 4 hours. After 4 hours, no starting material was present by TLC. The organic solvent was removed under reduced pressure, and the resulting suspension was diluted with 10 mL H$_2$O and adjusted to pH 5-6 with 1 N HCl. The resulting suspension was extracted with EtOAc (3×10 mL), dried over Na$_2$SO$_4$ and concentrated to yield a light yellow solid. Crude product was purified by HPLC (C18; MeCN/H$_2$O 60%:40%, isocratic) to yield the title compound.

Example 9. Synthesis of N-(4-((4-methoxyphenyl)sulfonamido)isoquinolin-1-yl)-N-((4-methoxyphenyl)sulfonyl)alanine

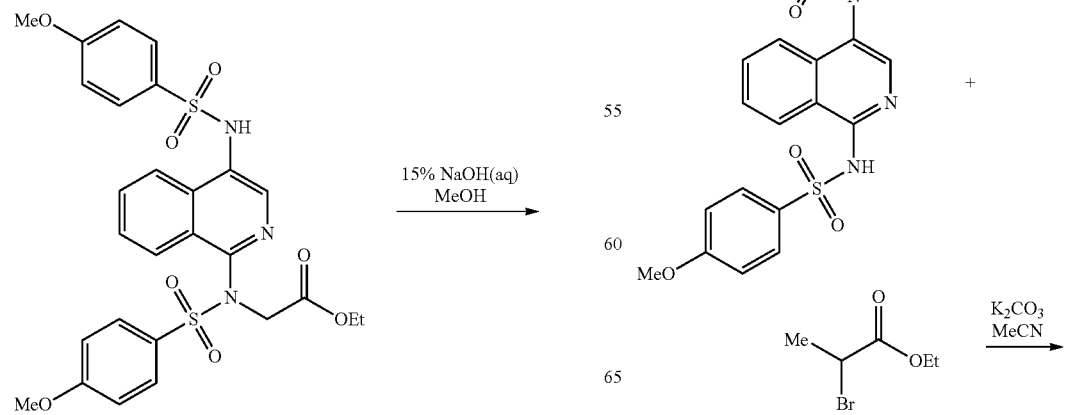

-continued

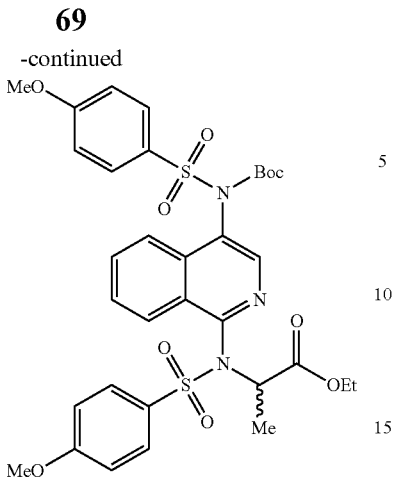

-continued

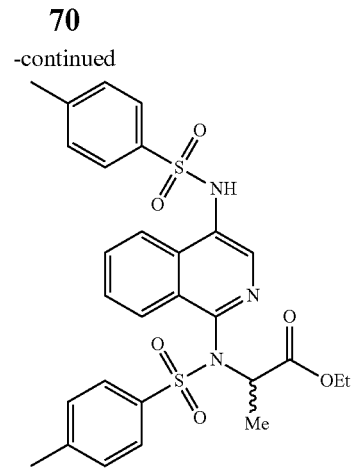

Ethyl N-(4-((N-(tert-butoxycarbonyl)-4-methoxy-phenyl)sulfonamido)isoquinolin-1-yl)-N-((4-methoxyphenyl)sulfonyl)alaninate (20)

In a 4 mL screw cap vial tert-butyl (1-((4-methoxyphenyl)sulfonamido)isoquinolin-4-yl)((4-methoxyphenyl)sulfonyl)carbamate (16) (190 mg, 0.32 mmol) and potassium carbonate (66 mg, 0.47 mmol) were placed and acetonitrile (1 mL) was added. Ethyl 2-bromopropionate (123 μL, 1.11 mmol) was added to the stirred suspension and the resulting mixture was allowed to stir for 36 hours. Upon complete consumption of starting material as determined by LC-MS the reaction was diluted with EtOAc (2 mL) and filtered through a small pad of celite, washing with EtOAc. The filtrate was concentrated under reduced pressure to yield a yellow oil. The crude product was purified by column chromatography (silica gel; EtOAc/Hexanes 0:100 to 30:70). Pure fractions were combined and concentrated under reduced pressure to yield 12 mg (5% yield) of (20) as a light yellow residue.

ethyl N-(4-((4-methoxyphenyl)sulfonamido)isoqui-nolin-1-yl)-N-((4-methoxyphenyl)sulfonyl) alaninate (21)

In a 20 mL screw cap vial, ethyl N-(4-((N-(tert-butoxycarbonyl)-4-methoxyphenyl)sulfonamido)isoquinolin-1-yl)-N-((4-methoxyphenyl)sulfonyl)alaninate (20) (13 mg, 0.019 mmol) was dissolved in dichloromethane (0.5 mL) and the resulting solution was cooled to 0° C. in an ice/water bath. Once cooled, trifluoroacetic acid (0.25 mL, 3.3 mmol) was added to the isoquinoline solution and the reaction was allowed to slowly warm to room temperature. After 2 hours the reaction was quenched with sat. aq. NaHCO₃ (3 mL) and the resulting mixture was allowed to stir for 30 minutes. The layers were separated and the aqeuous later was extracted with DCM (5 mL) the combined organics were washed with brine (5 mL) and dried over MgSO₄ to yield a brown residue. The crude product was purified by column chromatography (silica gel; EtOAc/hexanes, 0/100 to 30/70) 3.6 mg (32% yield) of (21) as a light brown residue.

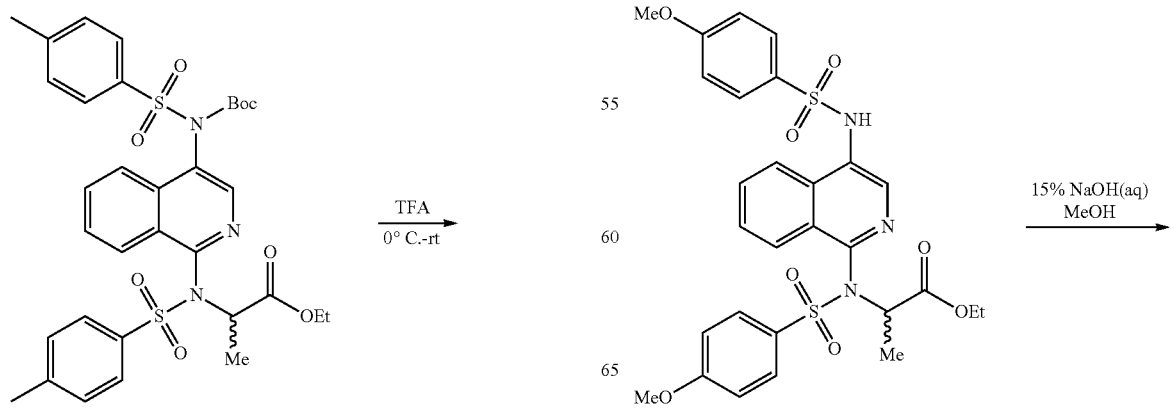

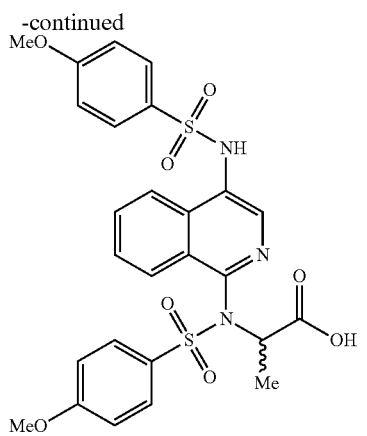

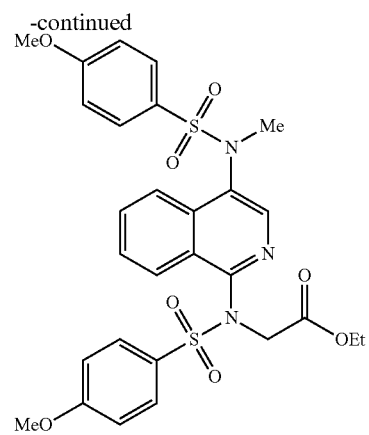

N-(4-((4-methoxyphenyl)sulfonamido)isoquinolin-1-yl)-N-((4-methoxyphenyl)sulfonyl)alanine (22)

In a 20 mL screw cap vial, ethyl N-(4-((4-methoxyphenyl)sulfonamido)isoquinolin-1-yl)-N-((4-methoxyphenyl)sulfonyl)alaninate (21) (3.6 mg, 0.006 mmol) was dissolved in MeOH (3 mL) and 15% NaOH in H₂O (wt/wt) was added to the solution. The reaction was stirred for 4 hours. After 4 hours, no starting material was present by TLC. The organic solvent was removed under reduced pressure, and the resulting suspension was diluted with 10 mL H₂O and adjusted to pH 5-6 with 1 N HCl. The resulting suspension was extracted with EtOAc (3×10 mL), dried over Na₂SO₄ and concentrated to yield a light yellow solid. Crude product was purified by HPLC (C18; MeCN/H₂O 60%:40%, isocratic) to yield the title compound.

Example 10. Synthesis of N-(4-((4-methoxy-N-methylphenyl)sulfonamido)isoquinolin-1-yl)-N-((4-methoxyphenyl)sulfonyl)glycine ethyl N-(4-((4-methoxy-N-methylphenyl)sulfonamido)isoquinolin-1-yl)-N-((4-methoxyphenyl)sulfonyl)glycinate (23)

In a screw cap vial ethyl Ethyl N-(4-((4-methoxyphenyl)sulfonamido)isoquinolin-1-yl)-N-((4-methoxyphenyl)sulfonyl)glycinate (18) (18.5 mg, 0.03 mmol) and potassium carbonate (6.5 mg, 0.05 mmol) were dissolved in MeCN (0.2 mL) and iodomethane (2.94 µL, 0.05 mmol) was added. The reaction was stirred overnight. The reaction was diluted with ethyl acetate and filtered through a short pad of celite. The filtrate was concentrated under reduced pressure to yield a yellow oil. The crude product was purified by column chromatography (silica gel; EtOAc/Hexanes, 0:100 to 30:70) afford 14 mg (74% yield) of (23) an off white solid.

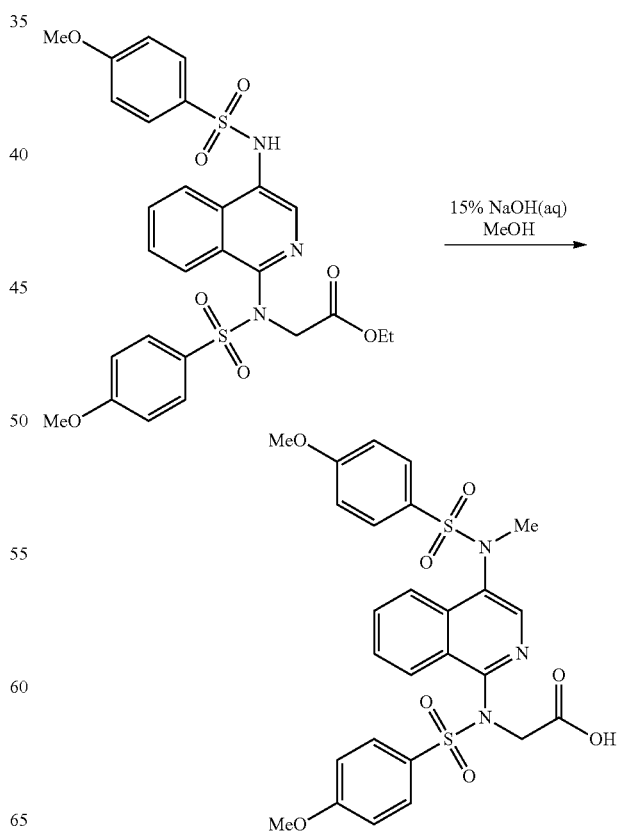

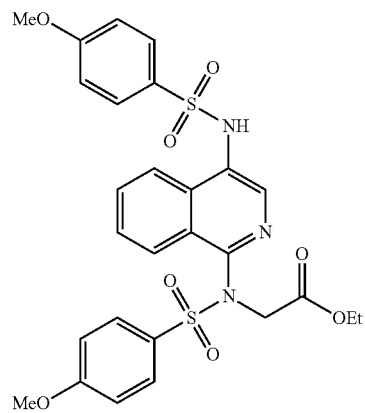

N-(4-((4-methoxy-N-methylphenyl)sulfonamido) isoquinolin-1-yl)-N-((4-methoxyphenyl) sulfonyl) glycine (24)

In a 4 mL screw cap vial ethyl N-(4-((4-methoxy-N-methylphenyl)sulfonamido)isoquinolin-1-yl)-N-((4-methoxyphenyl)sulfonyl)glycinate (23) (14 mg, 0.023 mmol) was dissolved in methanol (2 mL) and 15% NaOH$_{(aq)}$ (0.25 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na$_2$SO$_4$, and concentrated to yield an off white solid. Crude product was purified by HPLC (C18; MeCN/H$_2$O 60%:40%, isocratic) to yield the title compound.

Example 11. Synthesis of N-(4-((4-methoxy-N-(methyl-d3)phenyl)sulfonamido) isoquinolin-1-yl)-N-((4-methoxyphenyl)sulfonyl)glycine

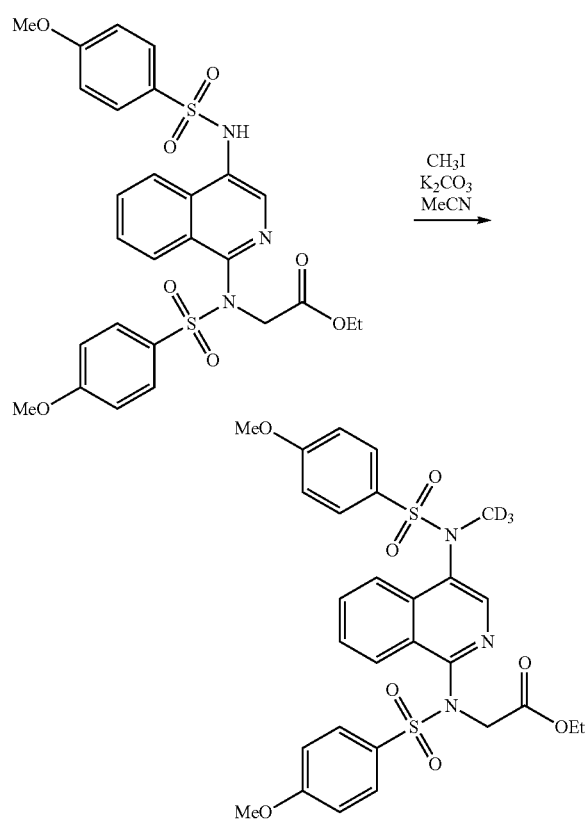

ethyl N-(4-((4-methoxy-N-(methyl-d$_3$)phenyl)sulfonamido)isoquinolin-1-yl)-N-((4-methoxyphenyl) sulfonyl)glycinate (25)

In a screw cap vial ethyl Ethyl N-(4-((4-methoxyphenyl) sulfonamido)isoquinolin-1-yl)-N-((4-methoxyphenyl)sulfonyl)glycinate (18) (20 mg, 0.34 mmol) and potassium carbonate (7.1 mg, 0.05 mmol) were dissolved in MeCN (0.2 mL) and iodomethane-d$_3$ (2.6 µL, 0.041 mmol) was added. The reaction was stirred overnight. The reaction was diluted with ethyl acetate and filtered through a short pad of celite. The filtrate was concentrated under reduced pressure to yield a yellow oil. The crude product was purified by column chromatography (silica gel; EtOAc/Hexanes, 0:100 to 30:70) afford 16 mg (78% yield) of (25) as an off white solid.

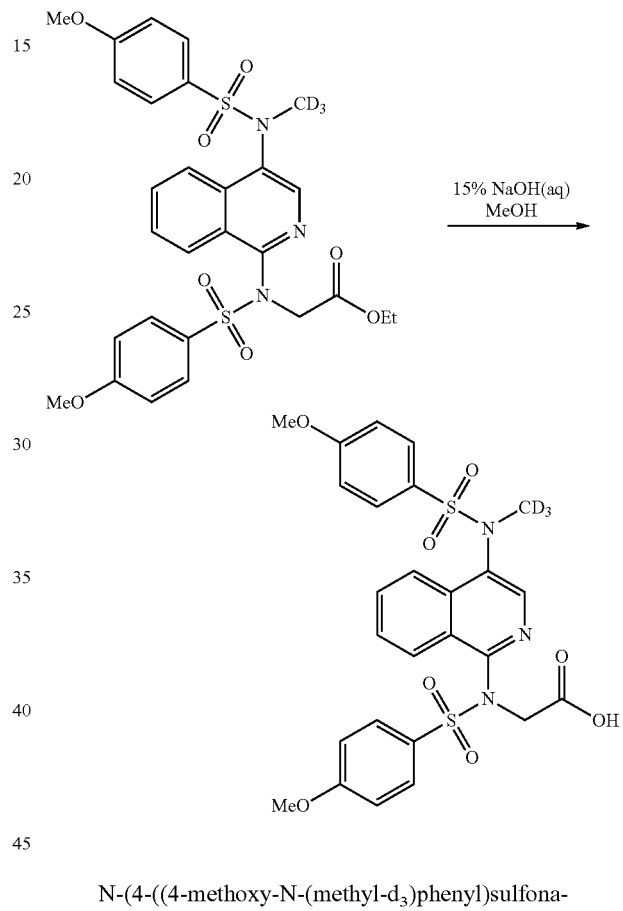

N-(4-((4-methoxy-N-(methyl-d$_3$)phenyl)sulfonamido)isoquinolin-1-yl)-N-((4-methoxyphenyl) sulfonyl)glycine (26)

In a 20 mL screw cap vial ethyl N-(4-((4-methoxy-N-(methyl-d$_3$)phenyl)sulfonamido)isoquinolin-1-yl)-N-((4-methoxyphenyl)sulfonyl)glycinate (25) (16 mg, 0.027 mmol) was dissolved in methanol (2 mL) and 15% NaOH$_{(aq)}$ (0.25 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na$_2$SO$_4$, and concentrated to yield an off white solid. Crude product was purified by HPLC (C18; MeCN/H$_2$O 60%:40%, isocratic) to yield the title compound.

Example 12. Synthesis of N-(4-((4-methoxy-N-(2,2,2-trifluoroethyl)phenyl) sulfonamido)isoquinolin-1-yl)-N-((4-methoxyphenyl)sulfonyl)glycine

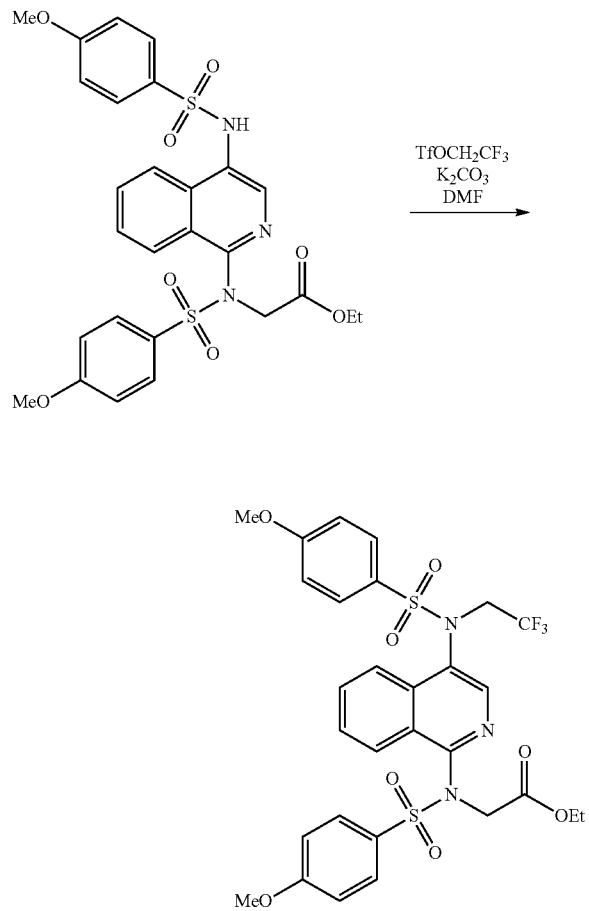 [SMILES: CCOC(=O)CN(c1ncc(N(C(=O)OC(C)(C)C)S(=O)(=O)c2ccc(OC)cc2)c2ccccc12)S(=O)(=O)c1ccc(OC)cc1 ; CCOC(=O)CN(c1ncc(NS(=O)(=O)c2ccc(OC)cc2)c2ccccc12)S(=O)(=O)c1ccc(OC)cc1]

ethyl N-(4-((4-methoxy-N-(2,2,2-trifluoroethyl)phenyl)sulfonamido)isoquinolin-1-yl)-N-((4-methoxyphenyl)sulfonyl)glycinate (27)

In a screw cap vial ethyl N-(4-((4-methoxyphenyl)sulfonamido)isoquinolin-1-yl)-N-((4-methoxyphenyl)sulfonyl)glycinate (18) (30 mg, 0.05 mmol) and potassium carbonate (28.4 mg, 0.21 mmol) were dissolved in DMF and 2,2,2-trifluoroethyl trifluromethanesulfonate (27 µL, 0.18 mmol) was added. The reaction was stirred overnight. The reaction was diluted with water and extracted with ethyl acetate (3×10 mL) the combined organics were washed with water (2×20 mL), brine (2×20 mL), dried over Na₂SO₄, and concentrated under reduced pressure to yield an orange oil. The crude product was purified by column chromatography (silica gel; EtOAc/Hexanes, 0:100 to 30:70) afford 27.3 mg (80% yield) of (27) as an off white solid.

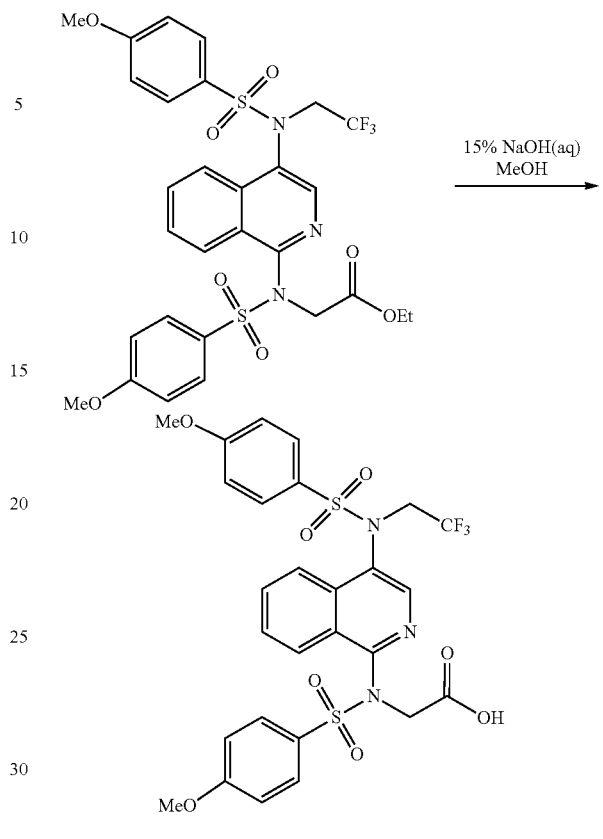

N-(4-((4-methoxy-N-(2,2,2-trifluoroethyl)phenyl) sulfonamido)isoquinolin-1-yl)-N-((4-methoxyphenyl)sulfonyl)glycine (28)

In a 4 mL screw cap vial ethyl N-(4-((4-methoxy-N-(2,2,2-trifluoroethyl)phenyl)sulfonamido)isoquinolin-1-yl)-N-((4-methoxyphenyl)sulfonyl)glycinate (27) (27.3 mg, 0.04 mmol) was dissolved in methanol (3 mL) and 15% NaOH$_{(aq)}$ (0.5 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na₂SO₄, and concentrated to yield an off white solid. Crude product was purified by HPLC (C18; MeCN/H₂O 60%:40%, isocratic) to yield the title compound.

Example 13. Synthesis of 4-methoxy-N-(4-(((4-methoxyphenyl)sulfonyl) methyl)naphthalen-1-yl) benzenesulfonamide

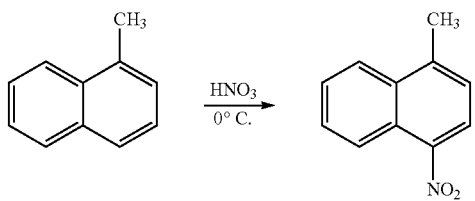

1-methyl-4-nitronaphthalene (29)

In a 3-neck round bottomed flask 1-methylnaphthalene (8 g, 56.3 mmol) was stirred at 0° C. as nitric acid (26 mL) was slowly added over 4 hours. The reaction mixture was stirred for an additional 15 minutes after the addition was complete. The reaction was quenched by pouring into water, slowly neutralized with NaHCO$_3$, and extracted with toluene, (3×75 mL) and the combined organic layers were washed with 10% NaOH (2×75 mL), dried over Na$_2$SO$_4$, and concentrated under a reduced pressure to yield an orange oil. The crude product was purified by column chromatography (silica gel; EtOAc/Hexanes, 0:100 to 20:80) to yield a yellow solid which still contained small amounts of region isomers. Pure product was obtained by recrystallization from EtOAc/Hexanes to afford 2.63 grams (25% yield) of (29) as yellow crystals.

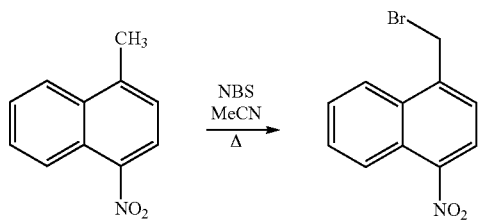

1-(bromomethyl)-4-nitronaphthalene (30)

In a single neck round bottomed flask 1-methyl-4-nitronaphthalene (29) (200 mg, 1.05 mmol) and N-bromosuccinamide (228 mg, 1.06 mmol) and AIBN (17.5 mg, 0.11 mmol) were dissolved in acetonitrile (5 mL) and the resulting solution was heated to reflux for 5 hours. After the reaction was complete the acetonitrile was removed under reduced pressure and the residue was dissolved in EtOAc. The Organic layer was washed with water (2×20 mL), brine (2×20 mL), dried over sodium sulfate and concentrated to yield an orange solid. The crude product was purified by column chromatography (silica gel; EtOAc/Hexanes, 0:100 to 10:90) to afford 213 mg (75% yield) of (30) as a light yellow solid.

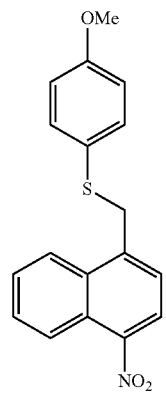

(4-methoxyphenyl)((4-nitronaphthalen-1-yl)methyl)sulfane (31)

In a 3 neck round bottomed flask 1M NaOH$_{(aq)}$ (2.5 mL) was cooled to 0° C. with an ice/water bath and 4-methoxybenzenethiol (116 mg, 0.83 mmol) was added in one portion and stirred for 30 minutes. 1-(bromomethyl)-4-nitronaphthalene (30) (213 mg, 0.80 mmol) was dissolved in dioxane and added dropwise to the stirred solution. After 5 hours the reaction was diluted with water and extracted with EtOAc (3×10 mL). the combined organic layers were washed with water (20 mL), brine, (20 mL), dried over Na$_2$SO$_4$ and concentrated to yield a yellow solid. The crude product was purified by column chromatography (silica gel; EtOAc/Hexanes, 0:100 to 20:80) afford 183.3 mg (70% yield) of (31) as a light yellow solid

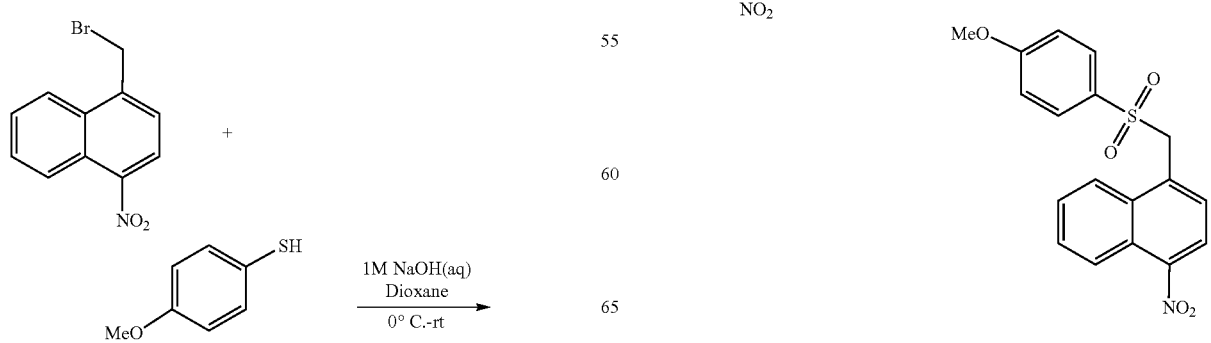

1-(((4-methoxyphenyl)sulfonyl)methyl)-4-nitronaphthalene (32)

In a 3 neck round bottomed flask a mixture of acetic anhydride (1 mL), acetic acid (1 mL) and 30% hydrogen peroxide in water (0.66 mL) was prepared to which (4-methoxyphenyl)((4-nitronaphthalen-1-yl)methyl)sulfane (31) (150 mg, 0.46 mmol) was added. The mixture was stirred for 5 hours. Upon completion the reaction was diluted with water (10 mL) and extracted with dichloromethane (3×10 mL). The combined organic layers were washed with sat. NaHCO$_3$ $_{(aq)}$ (2×15 mL), brine (15 mL), dried over Na$_2$SO$_4$ and concentrated to yield a yellow solid. The crude product was purified by column chromatography (silica gel; EtOAc/Hexanes, 0:100 to 10:90) afford 143 mg (87% yield) of (32) as a light yellow solid

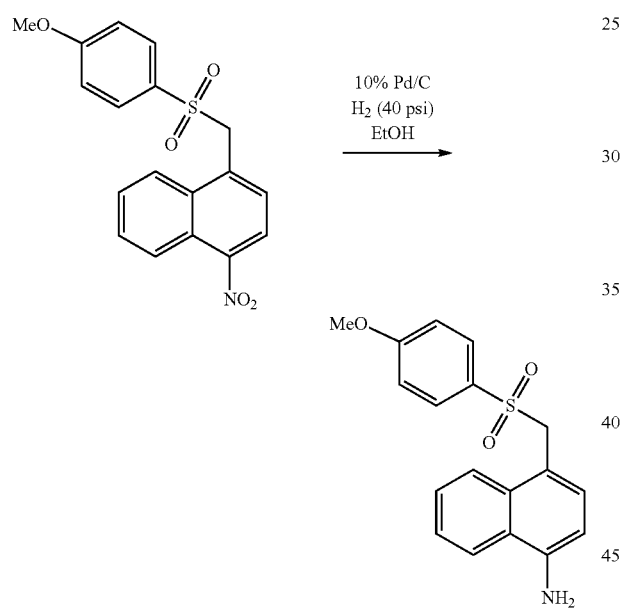

4-(((4-methoxyphenyl)sulfonyl)methyl)naphthalen-1-amine (33)

1-(((4-methoxyphenyl)sulfonyl)methyl)-4-nitronaphthalene (32) (104 mg, 0.28 mmol) and 10% Pd/C (14 mg) was added so a parr flask, which was sealed with a rubber septa and purged with argon. EtOAc (5 mL) was added under argon and the flask was attached to a parr shaker and purged with H$_2$ (40 psi) and shaken overnight. Upon completion, the flask was purged with argon and the mixture was filtered through celite. The pad of celite was washed with EtOAc (10 mL) and the filtrate was concentrated to yield 92 mg (99% yield) of (33) as an orange brown solid.

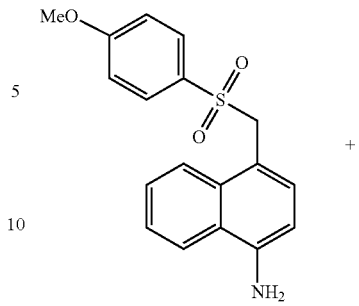

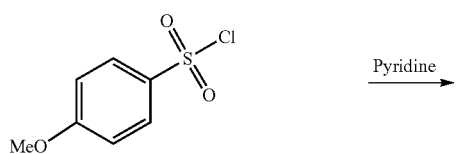

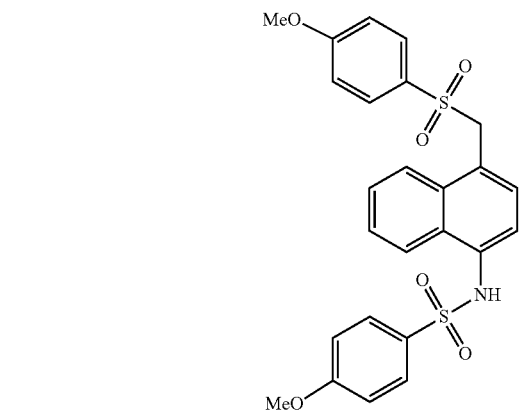

4-methoxy-N-(4-(((4-methoxyphenyl)sulfonyl)methyl)naphthalen-1-yl)benzenesulfonamide (34)

In a single neck round bottomed flask 4-(((4-methoxyphenyl)sulfonyl)methyl)naphthalen-1-amine (33) (92 mg, 0.28 mmol) was dissolved in pyridine (1.6 mL) and THF (5 mL) and 4-methoxybenezenesulfonyl chloride (70.4 mg, 0.34 mmol) was added. The reaction was stirred overnight. Upon completion the reaction was quenched with 2M HCl (10 mL) and extracted with EtOAc (3×10 mL). The combined organic layers were washed with 2M HCl (2×15 mL), water, (2×15 mL), brine (2×15 mL), dried over Na$_2$SO$_4$ and concentrated to yield a brown oil. The crude product was purified by column chromatography (silica gel; ETOAc: Hexanes, 0:100 to 40:60) to afford the title compound.

Example 14. Synthesis of N-((4-methoxyphenyl)sulfonyl)-N-(4-(((4-methoxyphenyl) sulfonyl)methyl)naphthalen-1-yl)glycine

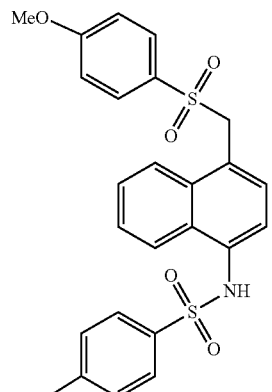

+

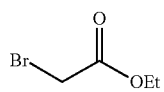

K₂CO₃
MeCN →

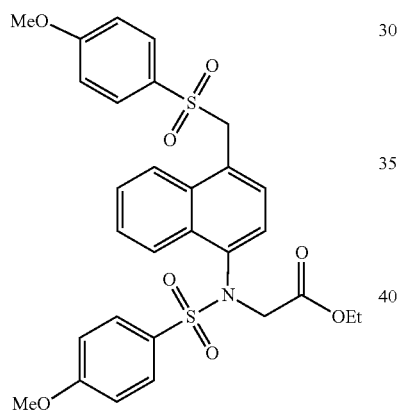

ethyl N-((4-methoxyphenyl)sulfonyl)-N-(4-(((4-methoxyphenyl)sulfonyl)methyl)naphthalen-1-yl)glycinate (35)

In a 4 mL screw cap vial 4-methoxy-N-(4-(((4-methoxyphenyl)sulfonyl)methyl) naphthalen-1-yl)benzenesulfonamide (34) (40 mg, 0.08 mmol), and K₂CO₃ (13.4 mg, 0.10 mmol), were suspended in acetonitrile and ethylbromoacetate (13.4 µL, 0.12 mmol) was added. The reaction was stirred overnight. Upon completion, the reaction was filtered through a short pad of celite washed with EtOAc and concentrated to yield a red-brown oil. The crude product was purified by column chromatography (silica gel; EtOAc/Hexanes, 0:100 to 30:70) afford 39.6 mg (84% yield) of (35) as an off white solid.

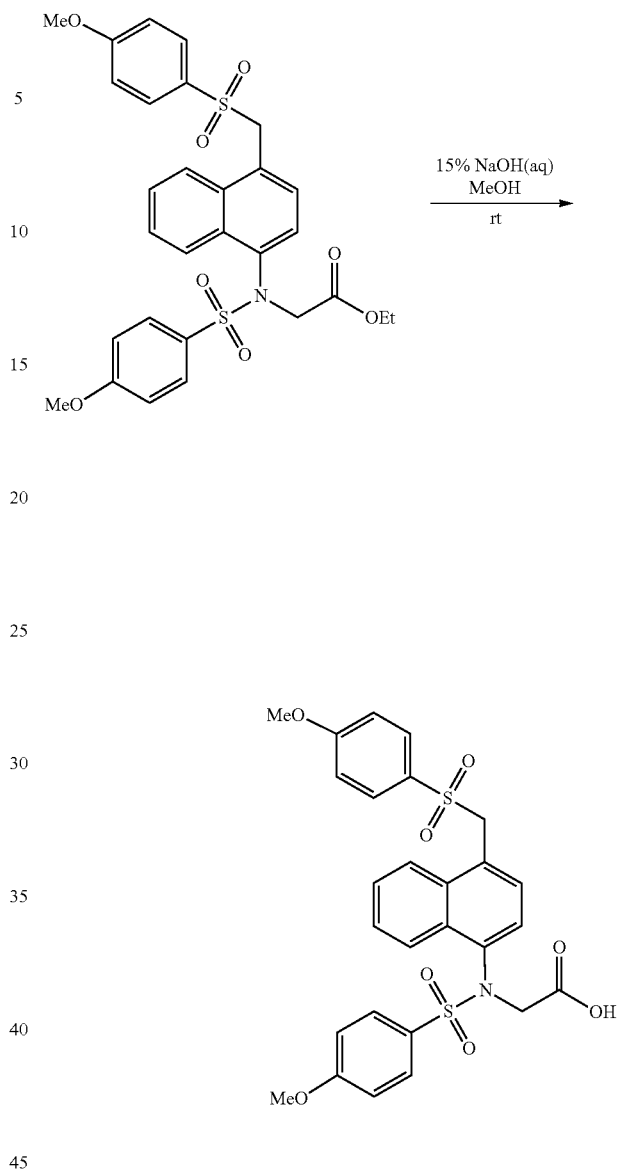

N-((4-methoxyphenyl)sulfonyl)-N-(4-(((4-methoxyphenyl)sulfonyl)methyl)naphthalen-1-yl)glycine (36)

In a 20 mL screw cap vial ethyl N-((4-methoxyphenyl)sulfonyl)-N-(4-(((4-methoxyphenyl)sulfonyl)methyl)naphthalen-1-yl)glycinate (35) (30 mg, 0.051 mmol) was dissolved in methanol (4 mL) and 15% NaOH$_{(aq)}$ (0.5 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na₂SO₄, and concentrated to yield the title compound.

Example 15. Synthesis of N-((4-methoxyphenyl)sulfonyl)-N-(4-(((4-methoxyphenyl) sulfonyl)methyl)naphthalen-1-yl)alanine

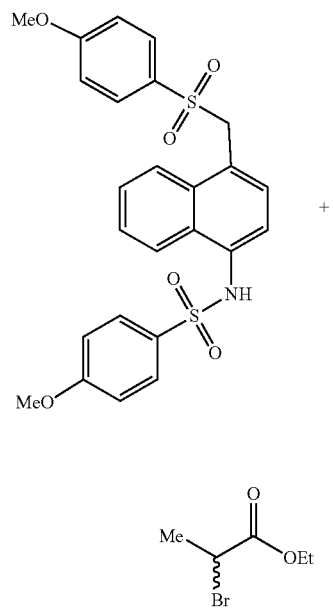

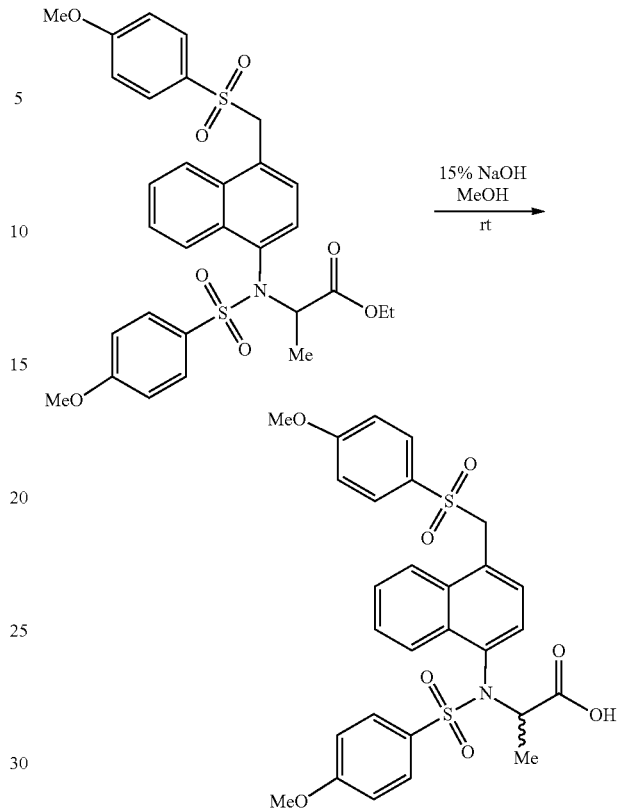

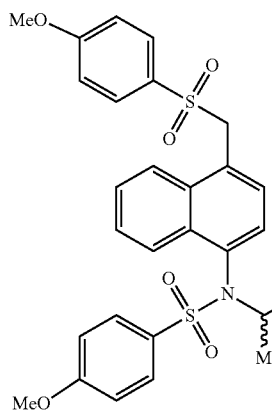

ethyl N-((4-methoxyphenyl)sulfonyl)-N-(4-(((4-methoxyphenyl)sulfonyl)methyl)naphthalen-1-yl)alaninate (37)

In a 4 mL screw cap vial 4-methoxy-N-(4-(((4-methoxyphenyl)sulfonyl) methyl)naphthalen-1-yl)benzenesulfonamide (34) (40 mg, 0.08 mmol), and K₂CO₃ (16.7 mg, 0.12 mmol), were suspended in acetonitrile (0.5 mL) and ethyl-2-bromopropionate (31.3 µL, 0.28 mmol) was added. The reaction was stirred for 48 h. Upon completion, the reaction was filtered through a short pad of celite washed with EtOAc and concentrated to yield a red-brown oil. The crude product was purified by column chromatography (silica gel; EtOAc/Hexanes, 0:100 to 30:70) afford 28 mg (58% yield) of (37) as an off white solid N-((4-methoxyphenyl)sulfonyl)-N-(4-(((4-methoxyphenyl)sulfonyl)methyl)naphthalen-1-yl)alanine (38)

In a 20 mL screw cap vial ethyl N-((4-methoxyphenyl)sulfonyl)-N-(4-(((4-methoxyphenyl)sulfonyl)methyl)naphthalen-1-yl)alaninate (37) (20 mg, 0.033 mmol) was dissolved in methanol (3 mL) and 15% NaOH$_{(aq)}$ (1 mL) was added. The reaction was stirred at room temperature for 4 hours. Upon completion the methanol was removed under reduced pressure, and the residual liquid was diluted with water (10 mL). The solution was adjusted to pH 4 and a white precipitate formed. The suspension was extracted with EtOAc (3×10 mL), washed with water (2×15 mL), brine (2×15 mL), dried over Na₂SO₄, and concentrated to yield an off white solid. Crude product was purified by HPLC (C18; MeCN/H₂O 60%:40%, isocratic) to yield the title compound.

Example 16. Synthesis of (2S,4S)-1-(4-((4-methoxyphenyl)sulfonamido)isoquinolin-1-yl)-4-phenylpyrrolidine-2-carboxylic acid

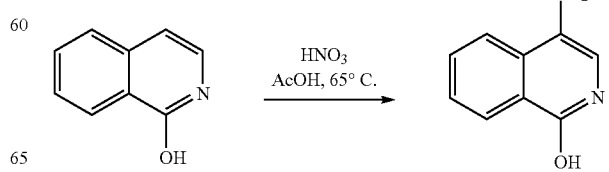

4-nitroisoquinolin-1-ol (39)

In a 3-neck round bottom flask 1-hydroxyisoquinoline (2.0 g, 13.8 mmol) was suspended in acetic acid (8 mL) and heated to 65° C. Nitric acid (2.6 mL) was added to the heated solution over 1 hour and stirred for 3 hours at 65° C. after the addition was complete. The reaction was then allowed to cool to room temperature, diluted with water and the yellow precipitate was collected by vacuum filtration. The solid was dried under vacuum to afford 1.44 g (55% yield) of (39) as a yellow solid.

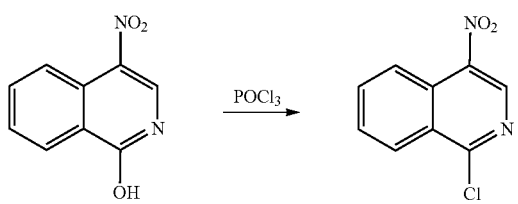

1-chloro-4-nitroisoquinoline (40)

In a single neck round bottom flask, 4-nitroisoquinolin-1-ol (39) (200 mg, 1.05 mmol), was suspended in phosphorus oxychloride (1.16 mL, 12.45 mmol) and heated to 105° C. for 1 hour. The reaction was allowed to cool to room temperature and excess phosphorous oxychloride was removed under reduced pressure. The residue was suspended in 1,2-dichloroethane (0.480 mL) and heated to 70° C. until a homogeneous solution was obtained. The solution was then cooled to 0° C. and isopropanol (1.5 mL) was added. The slurry was stirred for 2 hours at 0° C. The tan precipitate was collected by suction filtration and washed with cold isopropanol. The resulting solid was dried under vacuum to afford 101 mg (46% yield) of (40) as a tan powder.

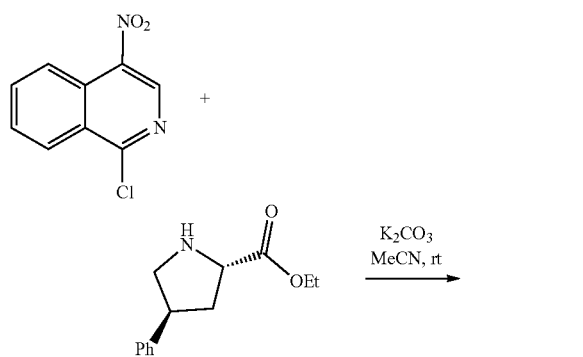

ethyl (2S,4S)-1-(4-nitroisoquinolin-1-yl)-4-phenylpyrrolidine-2-carboxylate (41)

In a 4 mL screw cap vial, 1-chloro-4-nitroisoquinoline (10 mg, 0.048 mmol), ethyl (2S,4S)-4-phenylpyrrolidine-2-carboxylate (40) (11.6 mg, 0.053 mmol), and $K_2CO_3$ (10 mg, 0.072 mmol) was suspended in acetonitrile (0.4 mL) and stirred overnight. The reaction was diluted with ethyl acetate (2 mL) and filtered through a short pad of celite. The filtrate was concentrated under reduced pressure to afford a yellow oil. The crude product was purified by column chromatography (silica gel; EtOAc/Hexanes, 0:100 to 30:70) afford 18 mg (96% yield) of (41) as a yellow solid.

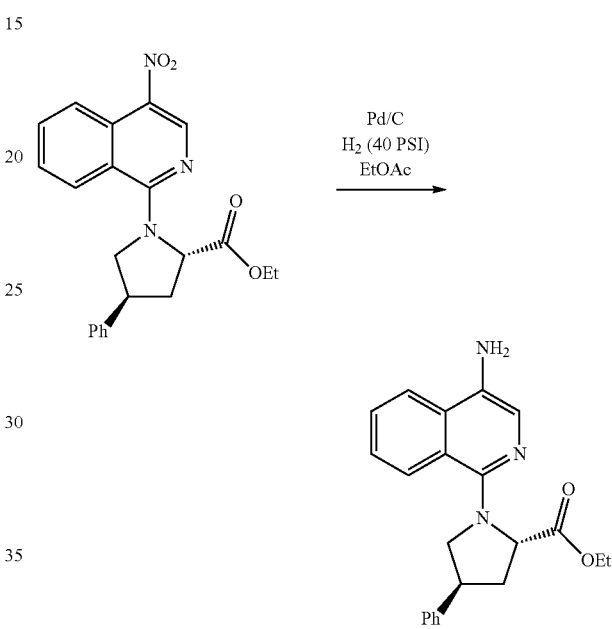

ethyl (2S,4S)-1-(4-aminoisoquinolin-1-yl)-4-phenylpyrrolidine-2-carboxylate (42)

Ethyl (2S,4S)-1-(4-nitroisoquinolin-1-yl)-4-phenylpyrrolidine-2-carboxylate (41) (19 mg, 0.049 mmol) and 10% Pd/C (1.9 mg, 10% wt) was placed in a Parr reaction bottle and the bottle was purged with argon. Ethyl acetate was added to the flask and the flask was affixed to a Parr shaker hydrogenation apparatus. The bottle was purged with hydrogen (40 PSI) and the reaction was shaken overnight. The bottle was purged with argon and the suspension was filtered through celite. The filtrate was concentrated afford 17.5 mg (99.7% yield) of (42) as a red-brown foam.

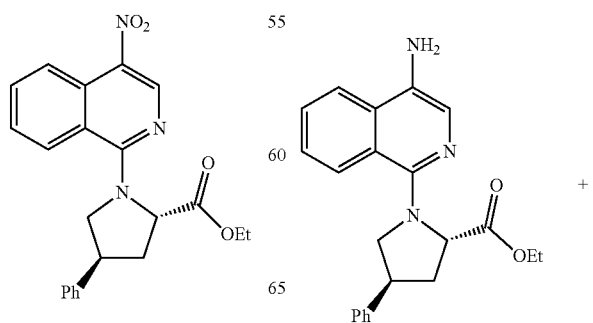

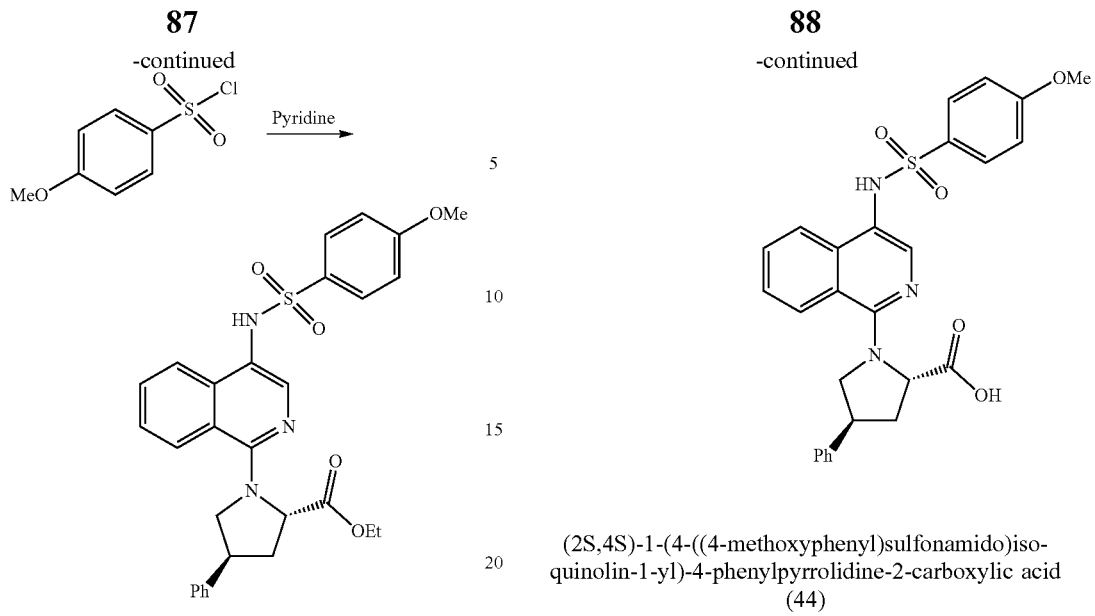

ethyl (2S,4S)-1-(4-((4-methoxyphenyl)sulfonamido)isoquinolin-1-yl)-4-phenylpyrrolidine-2-carboxylate (43)

In a 4 mL screw cap vial, ethyl (2S,4S)-1-(4-aminoisoquinolin-1-yl)-4-phenylpyrrolidine-2-carboxylate (42) (17.5 mg, 0.048 mmol) and 4-methoxybenznesulfonyl chloride (11.5 mg, 0.056 mmol) were dissolved in pyridine (1 mL) and the reaction was stirred for 1 hour. After 1 hour the reaction was slowly diluted with saturated aqueous NaHCO$_3$ (1 mL) and stirred for 10 minutes. The reaction was diluted with ethyl acetate (10 mL), and water (10 mL). The layers were separated and the aqueous layer was extracted with ethyl acetate (10 mL). The combined organics were washed with brine (20 mL), dried over Na$_2$SO$_4$, and concentrated under reduced pressure. Toluene (10 mL) was added to the resulting oil and removed under reduced pressure to yield a yellow-orange solid. The crude product was purified by column chromatography (silica gel; EtOAc/Hexanes, 0:100 to 35:65) afford 18.5 mg (72% yield) of (43) as an orange-yellow solid.

(2S,4S)-1-(4-((4-methoxyphenyl)sulfonamido)isoquinolin-1-yl)-4-phenylpyrrolidine-2-carboxylic acid (44)

In a 20 mL screw cap vial ethyl (2S,4S)-1-(4-((4-methoxyphenyl)sulfonamido)isoquinolin-1-yl)-4-phenylpyrrolidine-2-carboxylate (43) (18.5 mg, 0.035 mmol) was dissolved in methanol (3 mL) and 15% NaOH$_{(aq)}$ (0.5 mL) was added. The reaction was stirred at room temperature for 4 hours. Upon completion the methanol was removed under reduced pressure, and the residual liquid was diluted with water (10 mL). The solution was adjusted to pH 3 and a white precipitate formed. The suspension was extracted with EtOAc (3×10 mL), washed with brine (15 mL), dried over Na$_2$SO$_4$, and concentrated to yield an yellow-orange solid. Crude product was purified by HPLC (C18; MeCN/H$_2$O 60%:40% to 80%:20%) to yield the title compound.

Example 17. Synthesis of (4-((4-methoxyphenyl)sulfonamido)isoquinolin-1-yl)-D-proline

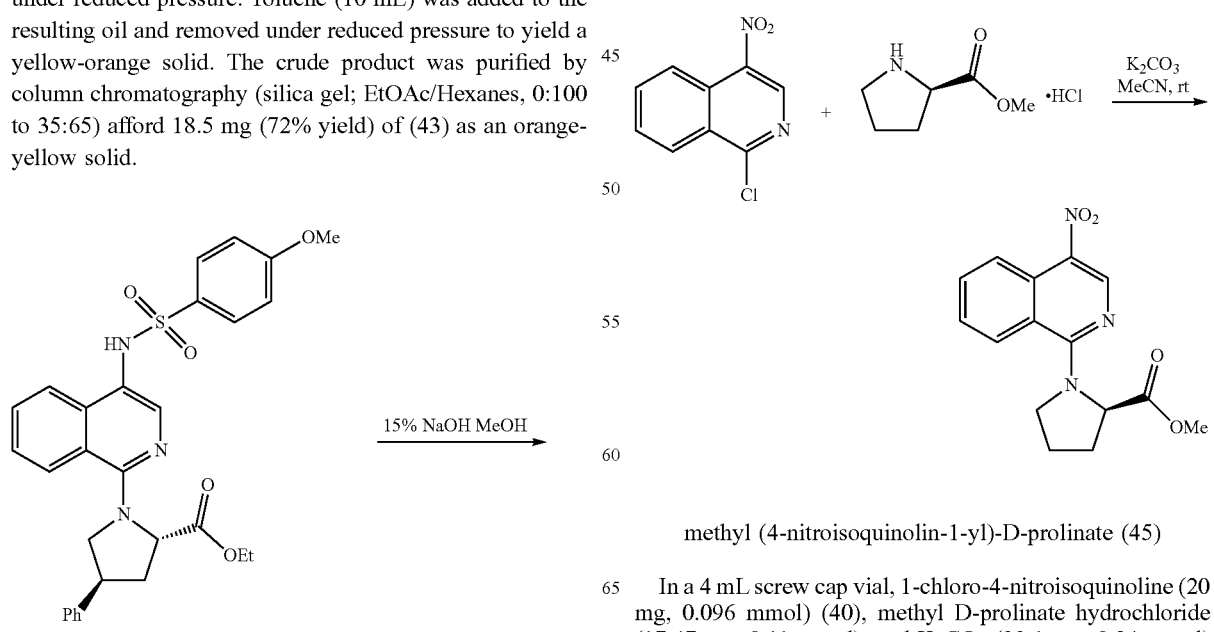

methyl (4-nitroisoquinolin-1-yl)-D-prolinate (45)

In a 4 mL screw cap vial, 1-chloro-4-nitroisoquinoline (20 mg, 0.096 mmol) (40), methyl D-prolinate hydrochloride (17.47 mg, 0.11 mmol), and K$_2$CO$_3$ (33.1 mg, 0.24 mmol)

was suspended in acetonitrile (0.3 mL) and stirred overnight. The reaction was diluted with ethyl acetate (2 mL) and filtered through a short pad of celite. The filtrate was concentrated under reduced pressure to afford a yellow oil. The crude product was purified by column chromatography (silica gel; EtOAc/Hexanes, 0:100 to 40:60) afford 27.5 mg (95% yield) of (45) as a yellow solid.

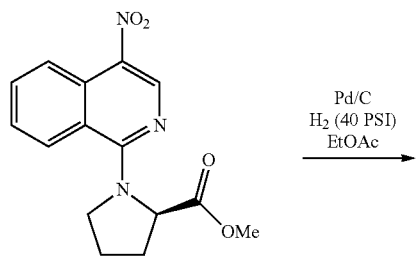

methyl (4-aminoisoquinolin-1-yl)-D-prolinate (46)

Methyl (4-nitroisoquinolin-1-yl)-D-prolinate (45) (27.5 mg, 0.091 mmol) and 10% Pd/C (2.8 mg, 10% wt) was placed in a Parr reaction bottle and the bottle was purged with argon. Ethyl acetate was added to the flask and the flask was affixed to a Parr shaker hydrogenation apparatus. The bottle was purged with hydrogen (40 PSI) and the reaction was shaken overnight. The bottle was purged with argon and the suspension was filtered through celite. The filtrate was concentrated afford 24 mg (97% yield) of (46) as a red foam.

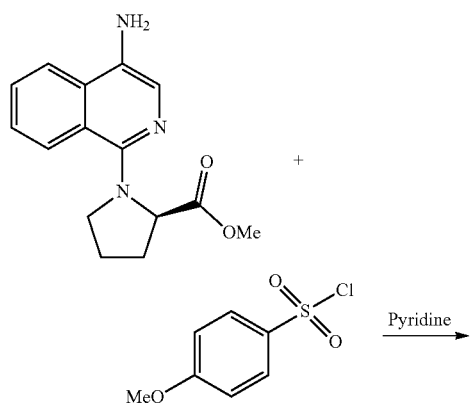

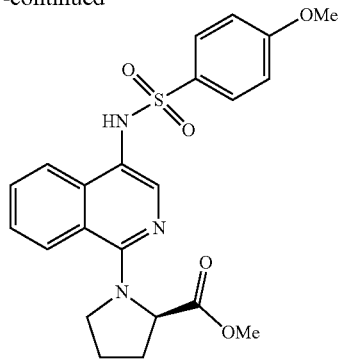

methyl (4-((4-methoxyphenyl)sulfonamido)isoquinolin-1-yl)-D-prolinate (47)

In a 4 mL screw cap vial, methyl (4-aminoisoquinolin-1-yl)-D-prolinate (46) (24 mg, 0.088 mmol) and 4-methoxybenznesulfonyl chloride (21.0 mg, 0.10 mmol) was dissolved in pyridine (1 mL) and the reaction was stirred for 1 hour. After 1 hour the reaction was slowly diluted with saturated aqueous NaHCO$_3$ (1 mL) and stirred for 10 minutes. The reaction was diluted with ethyl acetate (10 mL), and water (10 mL). The layers were separated and the aqueous layer was extracted with ethyl acetate (10 mL). The combined organics were washed with brine (20 mL), dried over Na$_2$SO$_4$, and concentrated under reduced pressure. Toluene (10 mL) was added to the resulting oil and removed under reduced pressure to yield a dark grey solid. The crude product was purified by column chromatography (silica gel; EtOAc/Hexanes, 0:100 to 45:55) afford 28.2 mg (72% yield) of (47) as an off white solid.

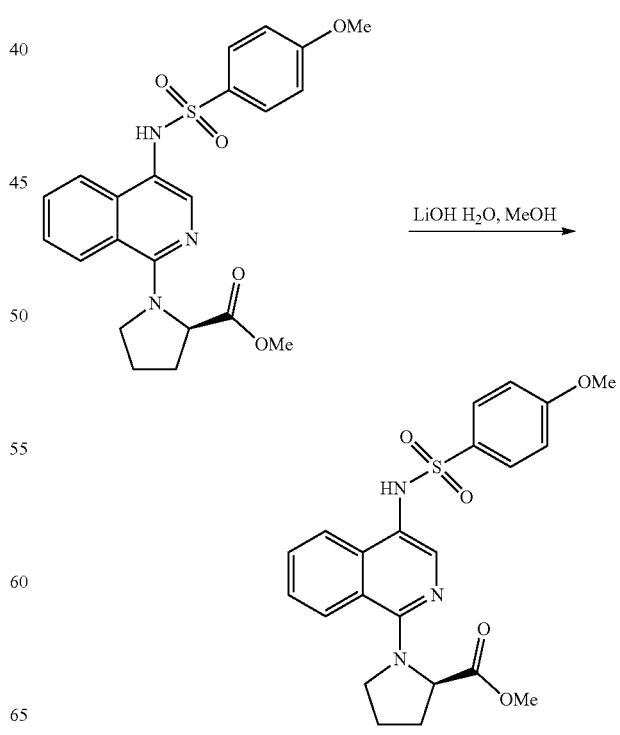

(4-((4-methoxyphenyl)sulfonamido)isoquinolin-1-yl)-D-proline (48)

In a 20 mL screw cap vial methyl (4-((4-methoxyphenyl) sulfonamido)isoquinolin-1-yl)-D-prolinate (47) (28.2 mg, 0.063 mmol) was dissolved in methanol (0.65 mL) and water (0.65 mL) to which LiOH (27 mg, 1.13 mmol) was added. The reaction was stirred at room temperature overnight. Upon completion, the methanol was removed under reduced pressure and the residual liquid was diluted with water (10 mL). The solution was adjusted to pH 3 with 1 N HCl and a white precipitate formed. The suspension was extracted with EtOAc (3×10 mL), washed with brine (15 mL), dried over Na$_2$SO$_4$, and concentrated to yield an yellow-orange solid. Crude product was purified by HPLC (C18; MeCN/H$_2$O 30%:70% to 50%:50%) to yield the title compound.

Example 18. Synthesis of (4-((4-methoxyphenyl) sulfonamido)isoquinolin-1-yl)-L-proline

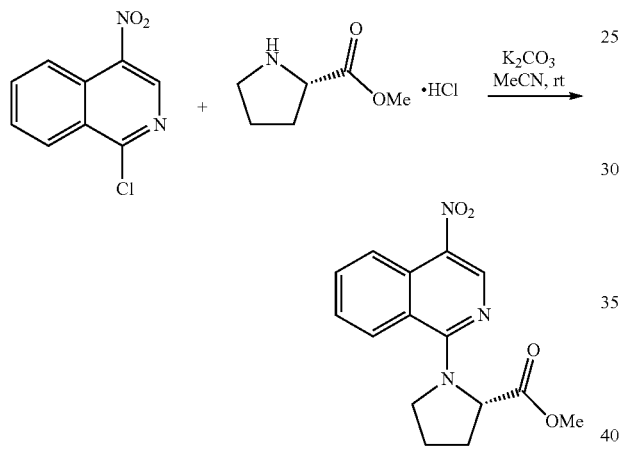

methyl (4-nitroisoquinolin-1-yl)-L-prolinate (49)

In a 4 mL screw cap vial, 1-chloro-4-nitroisoquinoline (40) (20 mg, 0.096 mmol), methyl L-prolinate hydrochloride (17.47 mg, 0.11 mmol), and K$_2$CO$_3$ (33.1 mg, 0.24 mmol) was suspended in acetonitrile (0.3 mL) and stirred overnight. The reaction was diluted with ethyl acetate (2 mL) and filtered through a short pad of celite. The filtrate was concentrated under reduced pressure to afford a yellow oil. The crude product was purified by column chromatography (silica gel; EtOAc/Hexanes, 0:100 to 40:60) afford 28.3 mg (98% yield) of (49) as a yellow solid.

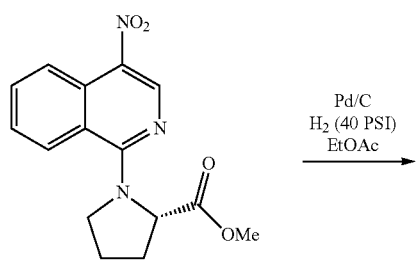

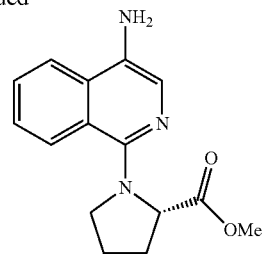

methyl (4-aminoisoquinolin-1-yl)-L-prolinate (50)

Methyl (4-nitroisoquinolin-1-yl)-L-prolinate (49) (28.3 mg, 0.094 mmol) and 10% Pd/C (2.8 mg, 10% wt) was placed in a Parr reaction bottle and the bottle was purged with argon. Ethyl acetate was added to the flask and the flask was affixed to a Parr shaker hydrogenation apparatus. The bottle was purged with hydrogen (40 PSI) and the reaction was shaken overnight. The bottle was purged with argon and the suspension was filtered through celite. The filtrate was concentrated afford 25 mg (98% yield) of (50) as a red foam.

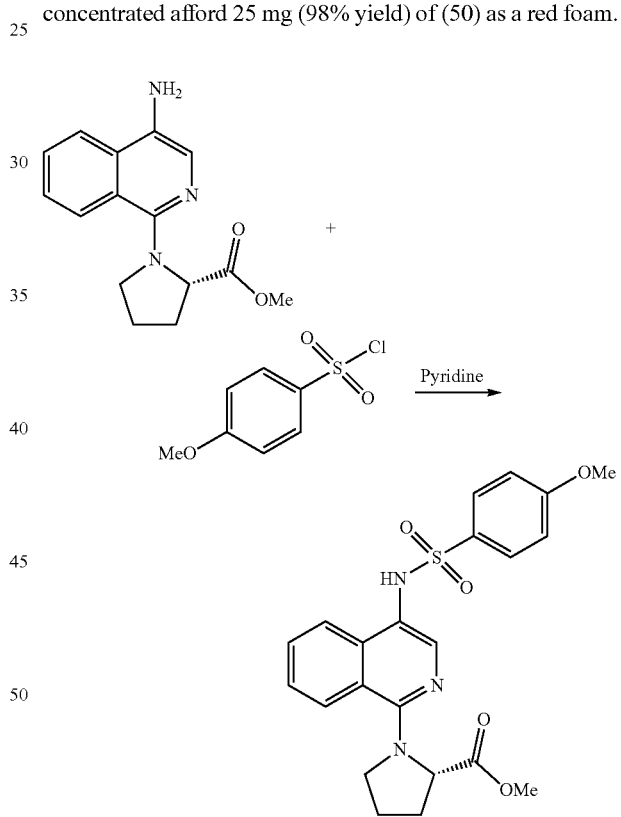

methyl (4-((4-methoxyphenyl)sulfonamido)isoquinolin-1-yl)-L-prolinate (51)

In a 4 mL screw cap vial, methyl (4-aminoisoquinolin-1-yl)-L-prolinate (50) (25 mg, 0.092 mmol) and 4-methoxy-benznesulfonyl chloride (23.2 mg, 0.056 mmol) were dissolved in pyridine (1 mL) and the reaction was stirred for 1 hour. After 1 hour the reaction was slowly diluted with saturated aqueous NaHCO$_3$ (1 mL) and stirred for 10 minutes. The reaction was diluted with ethyl acetate (10 mL), and water (10 mL). The layers were separated and the aqueous layer was extracted with ethyl acetate (10 mL). The combined organics were washed with brine (20 mL), dried over $Na_2SO_4$, and concentrated under reduced pressure. Toluene (10 mL) was added to the resulting oil and removed under reduced pressure to yield a dark grey solid. The crude product was purified by column chromatography (silica gel; EtOAc/Hexanes, 0:100 to 45:55) afford 21.4 mg (53% yield) of (51) as an off white solid.

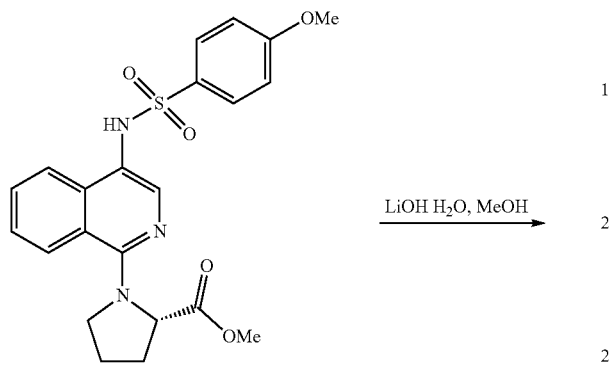

(4-((4-methoxyphenyl)sulfonamido)isoquinolin-1-yl)-L-proline (52)

In a 20 mL screw cap vial methyl (4-((4-methoxyphenyl) sulfonamido)isoquinolin-1-yl)-L-prolinate (51) (21.4 mg, 0.048 mmol) was dissolved in methanol (0.5 mL) and water (0.5 mL) to which LiOH (20.5 mg, 0.86 mmol) was added. The reaction was stirred at room temperature overnight. Upon completion, the methanol was removed under reduced pressure and the residual liquid was diluted with water (10 mL). The solution was adjusted to pH 3 with 1 N HCl and a white precipitate formed. The suspension was extracted with EtOAc (3×10 mL), washed with brine (15 mL), dried over $Na_2SO_4$, and concentrated to yield an yellow-orange solid. Crude product was purified by HPLC (C18; MeCN/ $H_2O$ 30%:70% to 50%:50%) to yield the title compound.

Example 19. Synthesis of (S)-4-methoxy-N-(1-(3-phenylpyrrolidin-1-yl)isoquinolin-4-yl)benzenesulfonamide

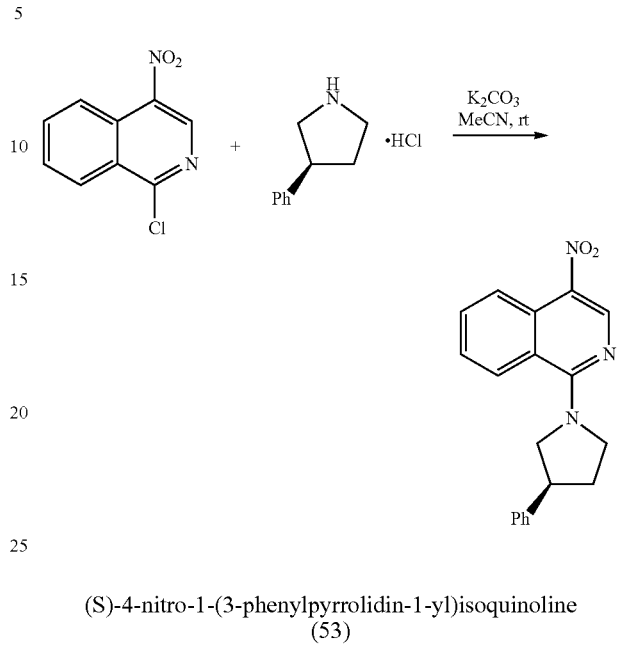

(S)-4-nitro-1-(3-phenylpyrrolidin-1-yl)isoquinoline (53)

In a 4 mL screw cap vial, 1-chloro-4-nitroisoquinoline (40) (21.8 mg, 0.01 mmol), (S)-3-phenylpyrrolidine hydrochloride (21.7 mg, 0.12 mmol), and $K_2CO_3$ (33.1 mg, 0.24 mmol) was suspended in acetonitrile (0.3 mL) and stirred overnight. The reaction was diluted with ethyl acetate (2 mL) and filtered through a short pad of celite. The filtrate was concentrated under reduced pressure to afford a yellow oil. The crude product was purified by column chromatography (silica gel; EtOAc/Hexanes, 0:100 to 20:80) afford 33 mg (99% yield) of (53) as a yellow solid.

(S)-1-(3-phenylpyrrolidin-1-yl)isoquinolin-4-amine (54)

(S)-4-nitro-1-(3-phenylpyrrolidin-1-yl)isoquinoline (53) (33 mg, 0.10 mmol) and 10% Pd/C (3.3 mg, 10% wt) was placed in a Parr reaction bottle and the bottle was purged with argon. Ethyl acetate was added to the flask and the flask was affixed to a Parr shaker hydrogenation apparatus. The bottle was purged with hydrogen (40 PSI) and the reaction was shaken overnight. The bottle was purged with argon and the suspension was filtered through celite. The filtrate was concentrated afford 27 mg (90% yield) of (54) as a dark purple foam.

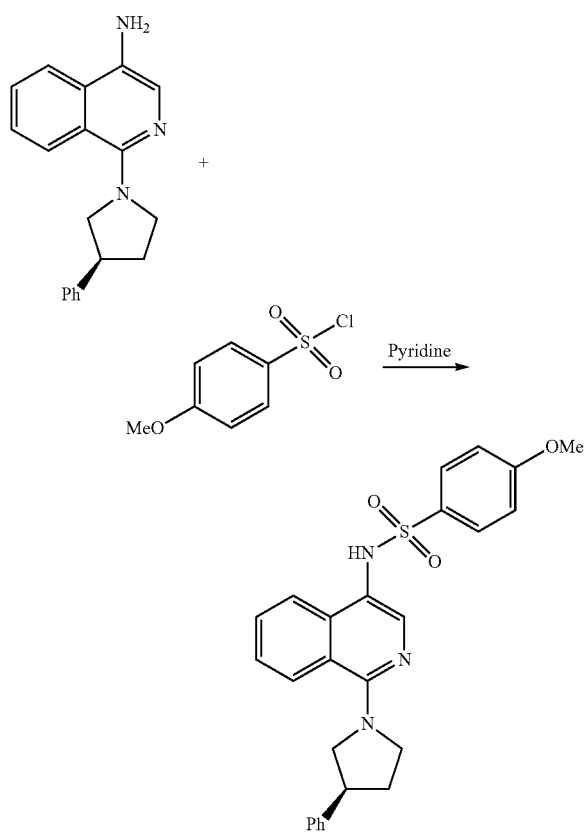

(S)-4-methoxy-N-(1-(3-phenylpyrrolidin-1-yl)iso-quinolin-4-yl)benzenesulfonamide (55)

In a 4 mL screw cap vial, (S)-1-(3-phenylpyrrolidin-1-yl)isoquinolin-4-amine (54) (27 mg, 0.093 mmol) and 4-methoxybenznesulfonyl chloride (22.3 mg, 0.11 mmol) was dissolved in pyridine (1 mL) and the reaction was stirred for 1 hour. After 1 hour the reaction was slowly diluted with saturated aqueous NaHCO$_3$ (1 mL) and stirred for 10 minutes. The reaction was diluted with ethyl acetate (10 mL), and water (10 mL). The layers were separated and the aqueous layer was extracted with ethyl acetate (10 mL). The combined organics were washed with brine (20 mL), dried over Na$_2$SO$_4$, and concentrated under reduced pressure. Toluene (10 mL) was added to the resulting oil and removed under reduced pressure to yield a dark grey solid. The crude product was purified by column chromatography (silica gel; EtOAc/Hexanes, 0:100 to 50:50) afford the title compound.

Example 20. Synthesis of (R)-4-methoxy-N-(1-(3-phenylpyrrolidin-1-yl)isoquinolin-4-yl)benzene-sulfonamide

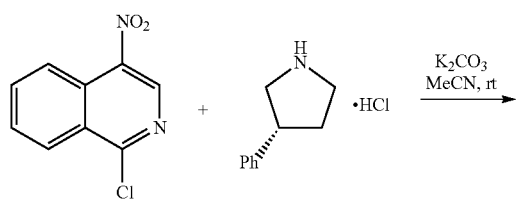

(R)-4-nitro-1-(3-phenylpyrrolidin-1-yl)isoquinoline (56)

In a 4 mL screw cap vial, 1-chloro-4-nitroisoquinoline (40) (20 mg, 0.096 mmol), (R)-3-phenylpyrrolidine hydrochloride (19.4 mg, 0.11 mmol), and K$_2$CO$_3$ (33.1 mg, 0.24 mmol) was suspended in acetonitrile (0.3 mL) and stirred overnight. The reaction was diluted with ethyl acetate (2 mL) and filtered through a short pad of celite. The filtrate was concentrated under reduced pressure to afford a yellow oil. The crude product was purified by column chromatography (silica gel; EtOAc/Hexanes, 0:100 to 30:70) afford 29 mg (95% yield) of (56) as a yellow solid.

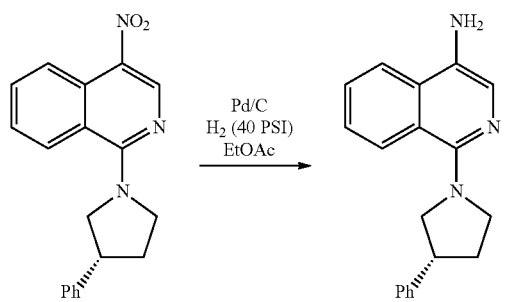 [SMILES: O=[N+]([O-])c1cnc(N2CC[C@H](c3ccccc3)C2)c2ccccc12 ; Nc1cnc(N2CC[C@H](c3ccccc3)C2)c2ccccc12]

(R)-1-(3-phenylpyrrolidin-1-yl)isoquinolin-4-amine (57)

(R)-4-nitro-1-(3-phenylpyrrolidin-1-yl)isoquinoline (56) (29 mg, 0.091 mmol) and 10% Pd/C (2.9 mg, 10% wt) was placed in a Parr reaction bottle and the bottle was purged with argon. Ethyl acetate was added to the flask and the flask was affixed to a Parr shaker hydrogenation apparatus. The bottle was purged with hydrogen (40 PSI) and the reaction was shaken overnight. The bottle was purged with argon and the suspension was filtered through celite. The filtrate was concentrated afford 26 mg (99% yield) of (57) as a dark purple foam.

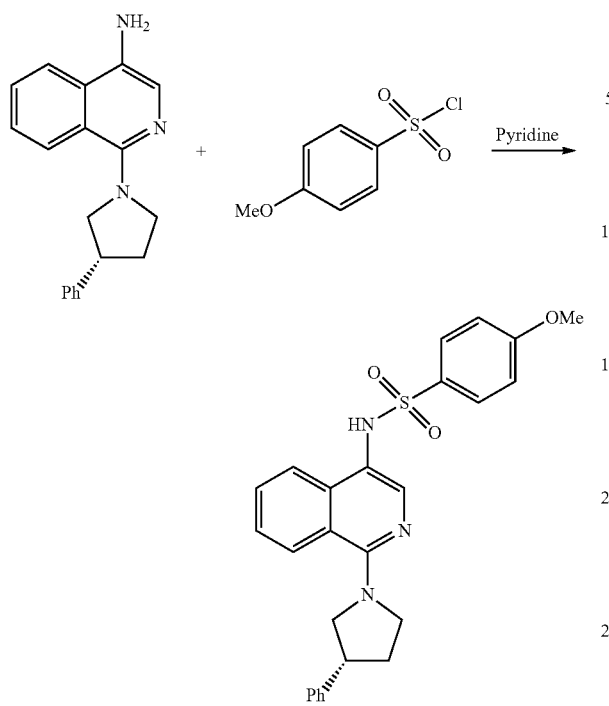

(R)-4-methoxy-N-(1-(3-phenylpyrrolidin-1-yl)iso-quinolin-4-yl)benzenesulfonamide (58)

In a 4 mL screw cap vial, (R)-1-(3-phenylpyrrolidin-1-yl)isoquinolin-4-amine (57) (26 mg, 0.090 mmol) and 4-methoxybenznesulfonyl chloride (22.0 mg, 0.11 mmol) was dissolved in pyridine (1 mL) and the reaction was stirred for 1 hour. After 1 hour the reaction was slowly diluted with saturated aqueous NaHCO$_3$ (1 mL) and stirred for 10 minutes. The reaction was diluted with ethyl acetate (10 mL), and water (10 mL). The layers were separated and the aqueous layer was extracted with ethyl acetate (10 mL). The combined organics were washed with brine (20 mL), dried over Na$_2$SO$_4$, and concentrated under reduced pressure. Toluene (10 mL) was added to the resulting oil and removed under reduced pressure to yield a dark grey solid. The crude product was purified by column chromatography (silica gel; EtOAc/Hexanes, 0:100 to 50:50) afford the title compound.

Example 21. Synthesis of Ethyl (E)-3-(4-((4-methoxyphenyl)sulfonamido)naphthalen-1-yl)acrylate

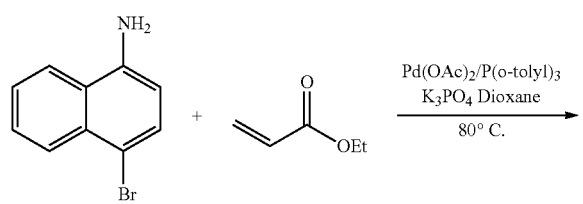

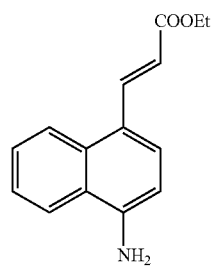

Ethyl (E)-3-(4-aminonaphthalen-1-yl)acrylate (59)

1-amino-4-bromonaphthalene (250 mg, 1.13 mmol), Pd(OAc)$_2$ (25.25 mg, 0.11 mmol), P(o-tolyl)$_3$ (34.25 mg, 0.11 mmol) and K$_3$PO$_4$ (525 mg, 2.47 mmol) were added to a flame dried shlenk tube. The tube was purged with argon and ethyl acrylate (450 µL, 4.13 mmol) and dioxane (2.5 mL) were added under a positive pressure of argon. The tube was sealed and heated to 80° C. for 24 hours. Upon completion the reaction was diluted with water (25 mL) and extracted with EtOAc (3×25 mL). the combined organic layers were washed with water (3×50 mL), brine (2×50 mL), dried over Na$_2$SO$_4$ and concentrated under a reduced pressure to yield a brown oil. The crude product was purified by column chromatography (silica gel; EtOAc/hexanes, 0/100 to 30/70) to yield 230 mg (85% yield) of (59) as a yellow solid.

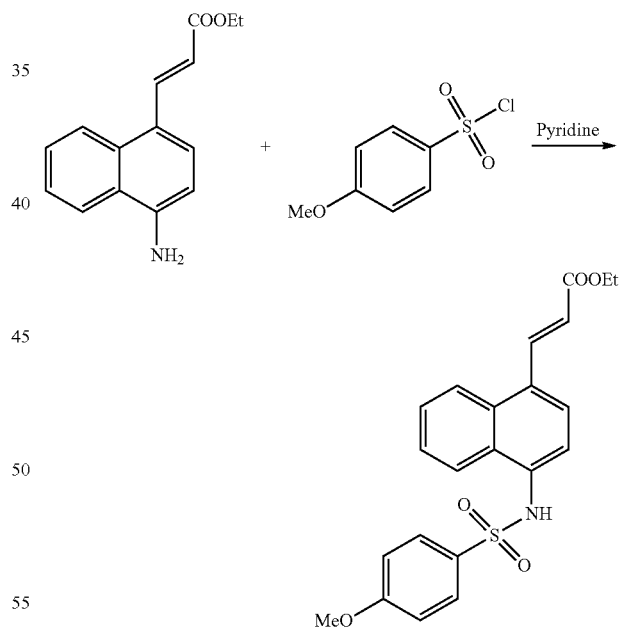

Ethyl (E)-3-(4-((4-methoxyphenyl)sulfonamido) naphthalen-1-yl)acrylate (60)

In a 10 mL round bottomed flask ethyl (E)-3-(4-aminonaphthalen-1-yl)acrylate (59) (80 mg, 0.33 mmol) was dissolved in pyridine (1 mL) and 4-methoxybenzenesulfonyl chloride (83 mg, 0.40 mmol) was added to the resulting solution. The reaction was stirred overnight. No starting material was present by LC-MS and the reaction was quenched with 2 N HCl (10 mL). The mixture was extracted with EtOAc (2×20 mL), the combined organics were washed with 2N HCl (2×20 mL), brine (20 mL), dried over Na₂SO₄, and concentrated to yield the title compound.

Example 22. Synthesis of (E)-3-(4-((4-methoxyphenyl)sulfonamido)naphthalen-1-yl)acrylic acid

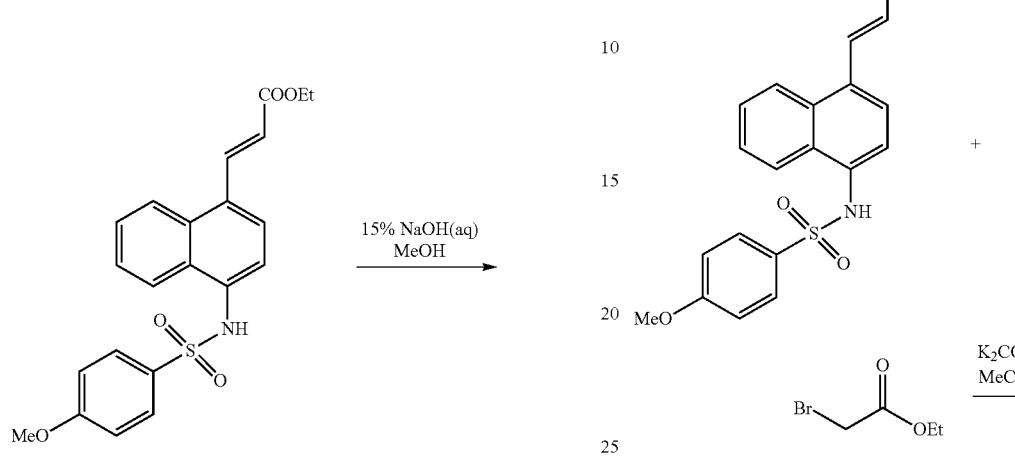

(E)-3-(4-((4-methoxyphenyl)sulfonamido)naphthalen-1-yl)acrylic acid (61)

In a 20 mL screw cap vial, Ethyl (E)-3-(4-((4-methoxyphenyl)sulfonamido)naphthalen-1-yl)acrylate (60) (50 mg, 0.12 mmol) was dissolved in MeOH (3 mL) and 15% NaOH(aq) (0.5 mL) was added. The reaction was stirred at room temperature for 4 hours. Upon completion methanol was removed under reduced pressure and the residue was diluted with 10 mL water. The solution was acidified with 2 N HCl(aq) to pH 4. The resulting suspension was extracted with EtOAc (3×10 mL), combined organics were washed with brine (20 mL) and dried over Na₂SO₄. Solvent was removed under reduced pressure to afford the title compound.

Example 23. Synthesis of Ethyl (E)-3-(4-((N-(2-ethoxy-2-oxoethyl)-4-methoxyphenyl) sulfonamido) naphthalen-1-yl)acrylate

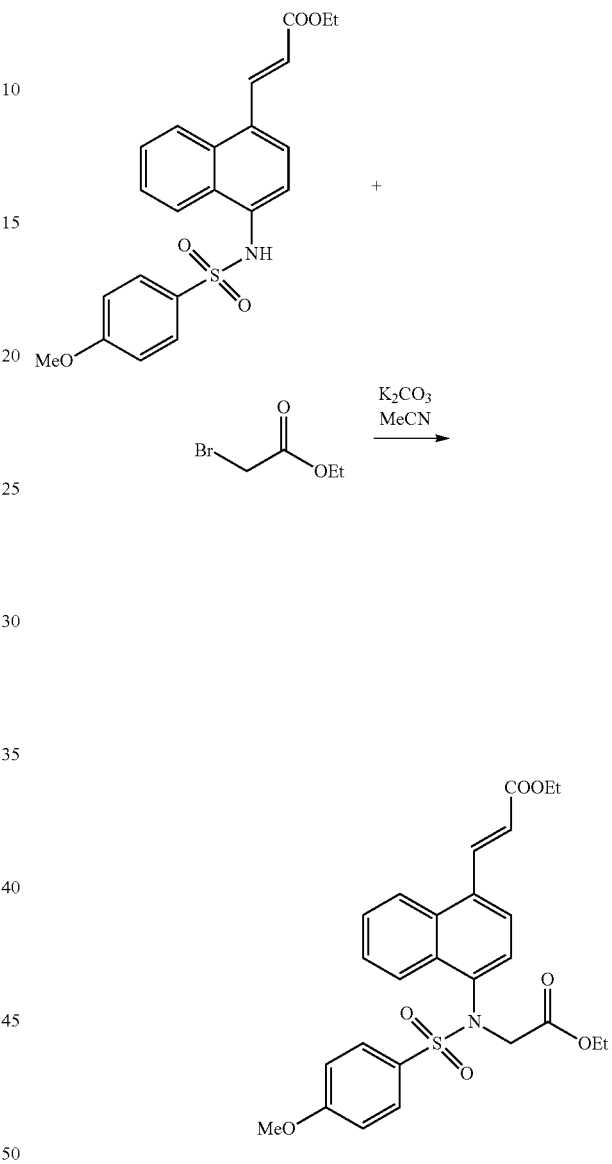

Ethyl (E)-3-(4-((N-(2-ethoxy-2-oxoethyl)-4-methoxyphenyl)sulfonamido)naphthalen-1-yl)acrylate (62)

In a 4 mL screw cap vial ethyl (E)-3-(4-((4-methoxyphenyl)sulfonamido)naphthalen-1-yl)acrylate (60) (70 mg, 0.17 mmol) and K₂CO₃ (28.2 mg, 0.2 mmol) were placed and MeCN (1 mL) was added followed by ethyl bromoacetate (28.3 μL, 0.26 mmol). The reaction was stirred overnight. Upon completion the reaction was diluted with ethyl acetate and filtered through celite. The filtrate was concentrated under reduced pressure to a yellow oil. The crude product was purified by column chromatography (silica gel; EtOAc/Hexanes, 0:100 to 40:60) to yield the title compound.

Example 24. Synthesis of (E)-3-(4-((N-(carboxymethyl)-4-methoxyphenyl)sulfonamido) naphthalen-1-yl)acrylic acid

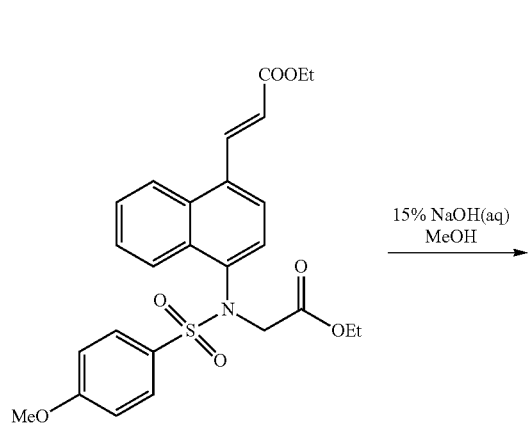

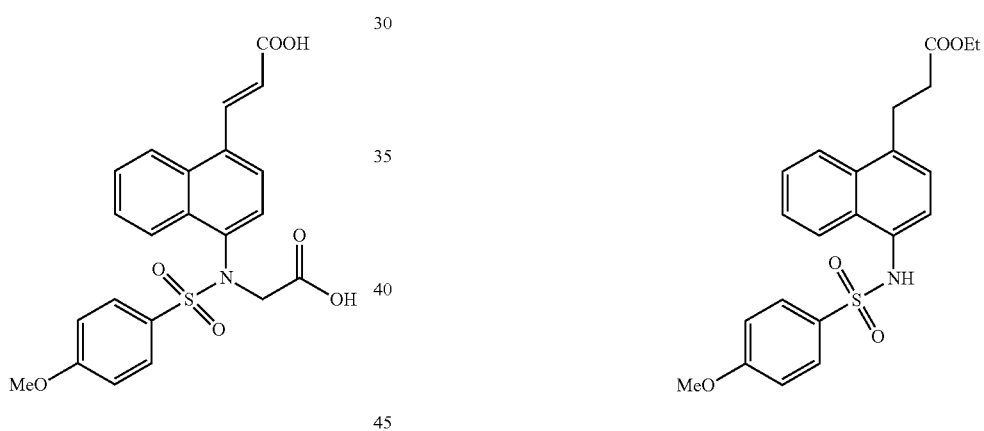

(E)-3-(4-((N-(carboxymethyl)-4-methoxyphenyl)sulfonamido)naphthalen-1-yl)acrylic acid (63)

In a 20 mL screw cap vial, ethyl (E)-3-(4-((N-(2-ethoxy-2-oxoethyl)-4-methoxyphenyl)sulfonamido)naphthalen-1-yl)acrylate (62) (64 mg, 0.13 mmol) was dissolved in MeOH (3 mL) and 15% NaOH(aq) (0.5 mL) was added. The reaction was stirred at room temperature for 4 hours. Upon completion methanol was removed under reduced pressure and the residue was diluted with 10 mL water. The solution was acidified with 2 N HCl(aq) to pH 4. The resulting suspension was extracted with EtOAc (3×10 mL), combined organics were washed with brine (20 mL) and dried over $Na_2SO_4$. Solvent was removed under reduced pressure to afford the title compound.

Example 25. Synthesis of Ethyl 3-(4-((4-methoxyphenyl)sulfonamido)naphthalen-1-yl)propanoate

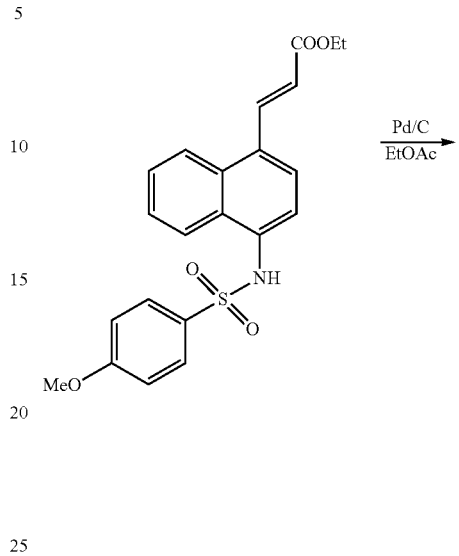

Ethyl 3-(4-((4-methoxyphenyl)sulfonamido)naphthalen-1-yl)propanoate (64)

In a 500 mL parr flask (E)-3-(4-((4-methoxyphenyl)sulfonamido)naphthalen-1-yl)acrylate (60) (114 g, 0.28 mmol) was placed and dissolved in EtOAc (3 mL). 10% Pd/C (18 mg) was added and the flask was purged with argon. The flask was placed on the parr shaker, purged with $H_2$, and shaken overnight under an atmosphere of $H_2$ (40 PSI). The crude reaction mixture was filtered through a pad of celite and the pad was washed with EtOAc. The solution was concentrated under reduced pressure to yield XX mg of an off white solid. The crude product was purified by column chromatography (silica gel; EtOAc/Hexanes, 0:100 to 30:70) to yield the title compound.

Example 26. Synthesis of 3-(4-((4-methoxyphenyl)sulfonamido)naphthalen-1-yl)propanoic acid

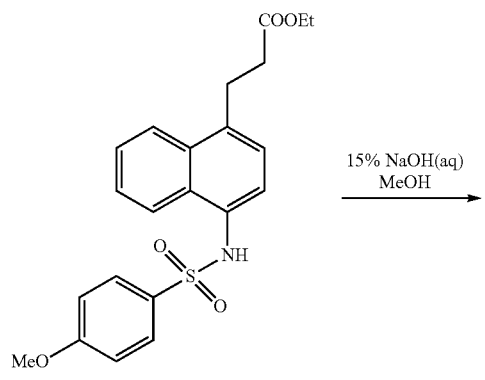

3-(4-((4-methoxyphenyl)sulfonamide)naphthalen-1-yl)propanoic acid (65)

In a 20 mL screw cap vial, ethyl 3-(4-((4-methoxyphenyl)sulfonamido)naphthalen-1-yl)propanoate (64) (50 mg, 1.21 mmol) was dissolved in MeOH (3 mL) and 15% NaOH(aq) (1 mL) was added. The reaction was stirred at room temperature for 4 hours. Upon completion methanol was removed under reduced pressure and the residue was diluted with 10 mL water. The solution was acidified with 2 N HCl(aq) to pH 4. The resulting suspension was extracted with EtOAc (3×10 mL), combined organics were washed with brine (20 mL) and dried over $Na_2SO_4$. Solvent was removed under reduced pressure to afford the title compound.

Example 27. Synthesis of Ethyl 3-(4-((N-(2-ethoxy-2-oxoethyl)-4-methoxyphenyl) sulfonamido)naphthalen-1-yl)propanoate

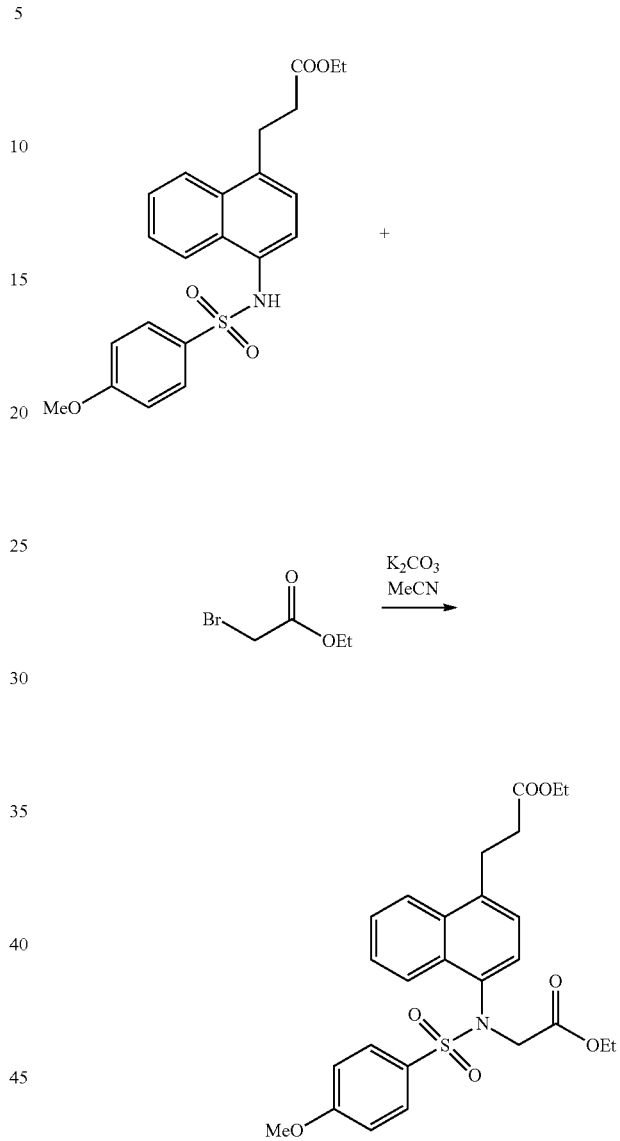

Ethyl 3-(4-((N-(2-ethoxy-2-oxoethyl)-4-methoxyphenyl)sulfonamido)naphthalen-1-yl)propanoate (66)

In a 4 mL screw cap vial ethyl 3-(4-((4-methoxyphenyl)sulfonamido)naphthalen-1-yl)propanoate (64) (114 mg, 0.28 mmol) and $K_2CO_3$ (57.2 mg, 0.41 mmol) were placed and MeCN (2 mL) was added followed by ethyl bromoacetate (46 µL, 0.42 mmol). The reaction was stirred overnight. Upon completion the reaction was diluted with ethyl acetate and filtered through celite. The filtrate was concentrated under reduced pressure to a light yellow oil. The crude product was purified by column chromatography (silica gel; EtOAc/Hexanes, 0:100 to 40:60) to yield the title compound.

Example 28. Synthesis of 3-(4-((N-(carboxymethyl)-4-methoxyphenyl)sulfonamido) naphthalen-1-yl)propanoic acid

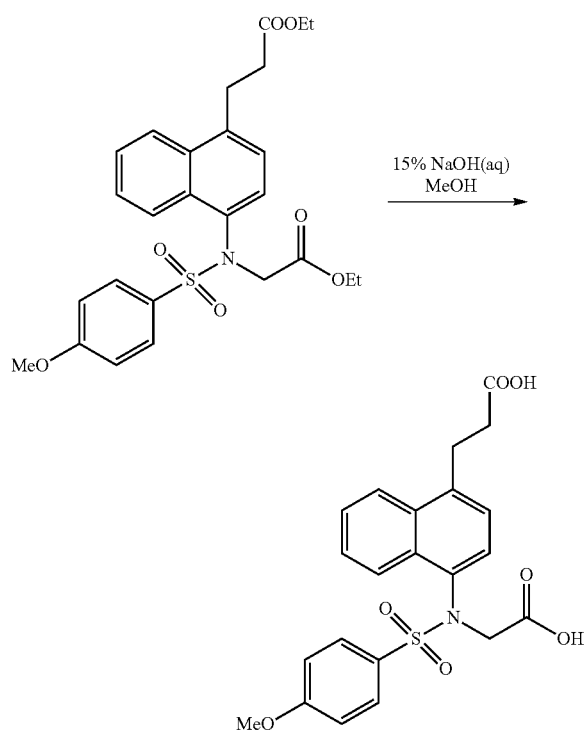

3-(4-((N-(carboxymethyl)-4-methoxyphenyl)sulfonamido)naphthalen-1-yl)propanoic acid (67)

In a 20 mL screw cap vial, ethyl 3-(4-((N-(2-ethoxy-2-oxoethyl)-4-methoxyphenyl)sulfonamido)naphthalen-1-yl)propanoate (66) (114 mg, 0.23 mmol) was dissolved in MeOH (4 mL) and 15% NaOH(aq) (0.5 mL) was added. The reaction was stirred at room temperature for 4 hours. Upon completion methanol was removed under reduced pressure and the residue was diluted with 10 mL water. The solution was acidified with 2 N HCl(aq) to pH 4. The resulting suspension was extracted with EtOAc (3×10 mL), combined organics were washed with brine (20 mL) and dried over $Na_2SO_4$. Solvent was removed under reduced pressure to afford the title compound.

Example 29. Synthesis of 4-methoxy-N-(4-(4-methoxyphenethyl)naphthalen-1-yl)benzenesulfonamide

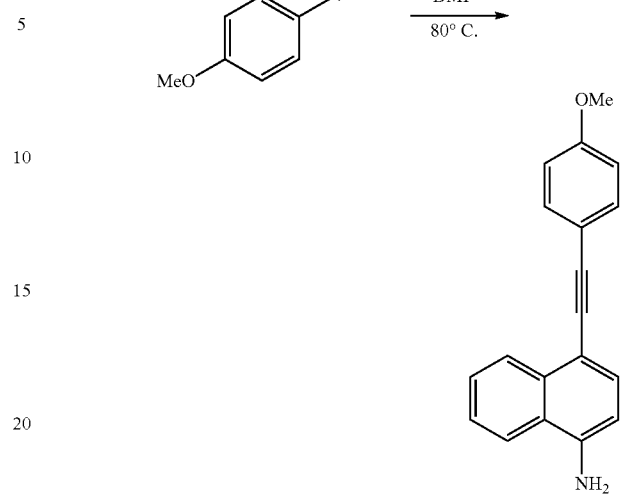

4-((4-methoxyphenyl)ethynyl)naphthalen-1-amine (68)

1-amino-4-bromonaphthalene (150 mg, 0.68 mmol), $Pd(PPh_3)_4$ (39 mg, 0.034 mmol), CuI (12.9 mg, 0.068 mmol) and 4-Ethynely anisole (116 mg, 0.88 mmol) were added to a flame dried shlenk tube. The tube was purged with argon and trimethylamine (207 µL, 1.5 mmol) and dimthylformamide (1.5 mL) were added under a positive pressure of argon. The tube was sealed and heated to 80° C. for 18 hours. Upon completion the reaction was poured into $H_2O$/ice (50 mL) and extracted with EtOAc (3×25 mL). the combined organic layers were washed with water (3×50 mL), brine (2×50 mL), dried over $Na_2SO_4$ and concentrated under a reduced pressure to yield a brown oil. The crude product was purified by column chromatography (silica gel; EtOAc/hexanes, 0/100 to 30/70) to yield 58 mg (31% yield) of (68) as a light yellow solid.

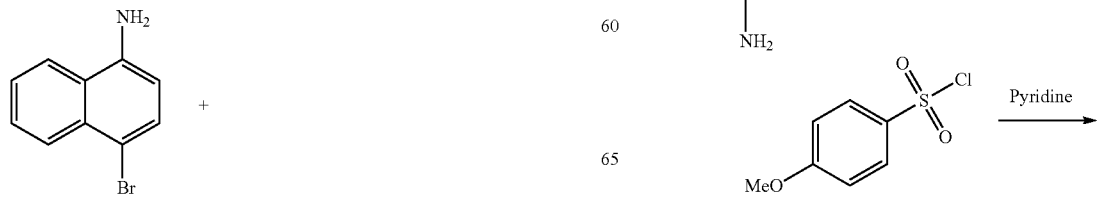

4-methoxy-N-(4-((4-methoxyphenyl)ethynyl)naph-thalen-1-yl)benzenesulfonamide (69)

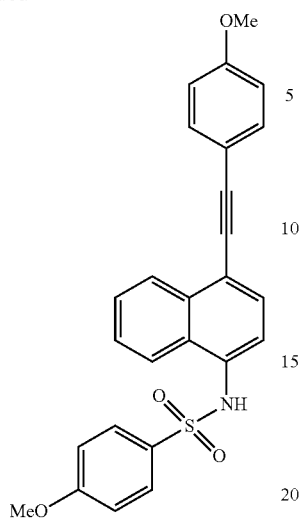

In a 4 mL screw cap vial 4-((4-methoxyphenyl)ethynyl) naphthalen-1-amine (68) (58 mg, 0.21 mmol) was dissolved in pyridine (0.75 mL) and 4-methoxybenzenesulfonyl chloride (49.6 mg, 0.24 mmol) was added to the resulting solution. The reaction was stirred overnight. No starting material was present by LC-MS and the reaction was quenched with 2 N HCl (10 mL). The mixture was extracted with EtOAc (2×20 mL), the combined organics were washed with 2N HCl (2×20 mL), brine (20 mL), dried over Na$_2$SO$_4$, and concentrated to yield 93 mg (99% yield) of (69) as a light brown solid. Product did not require purification.

4-methoxy-N-(4-(4-methoxyphenethyl)naphthalen-1-yl)benzenesulfonamide (70)

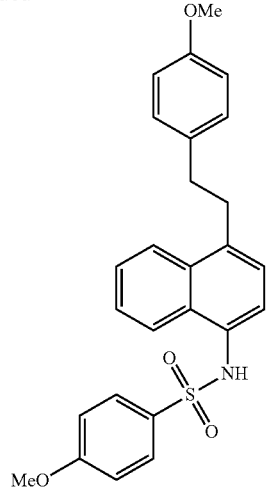

In a 500 mL parr flask 4-methoxy-N-(4-((4-methoxyphenyl)ethynyl)naphthalen-1-yl)benzenesulfonamide (69) (20 mg, 0.045 mmol) was placed and dissolved in EtOAc (3 mL). 10% Pd/C (4 mg) was added and the flask was purged with argon. The flask was placed on the parr shaker, purged with H$_2$, and shaken overnight under an atmosphere of H$_2$ (40 PSI). The crude reaction mixture was filtered through a pad of celite and the pad was washed with EtOAc. The solution was concentrated under reduced pressure to yield 20 mg of an off white solid. The crude product was purified by column chromatography (silica gel; EtOAc/Hexanes, 0:100 to 30:70) to yield the title compound.

Example 30. Synthesis of Ethyl N-(4-(4-methoxyphenethyl)naphthalen-1-yl)-N-((4-methoxyphenyl)sulfonyl)glycinate

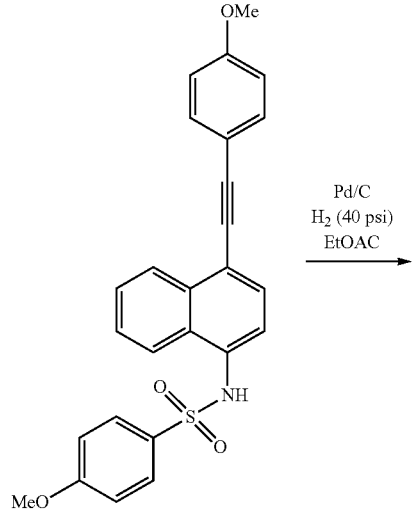
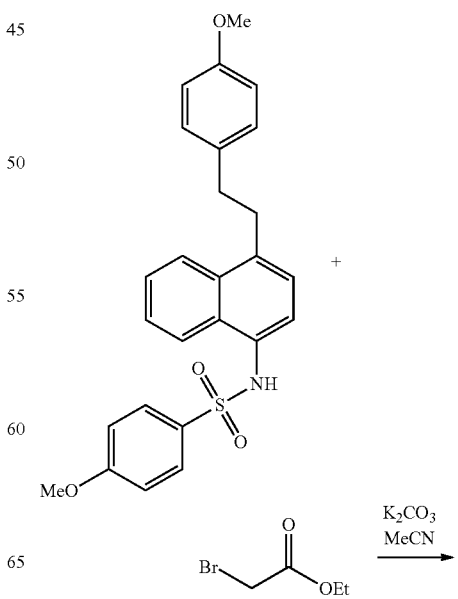

109
-continued

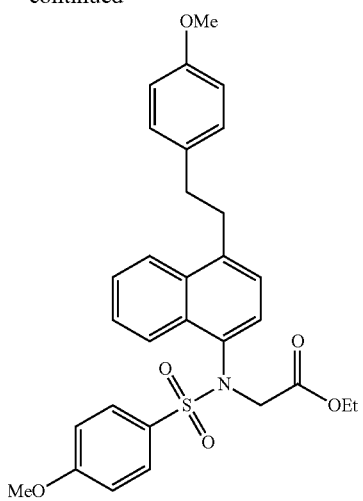

Ethyl N-(4-(4-methoxyphenethyl)naphthalen-1-yl)-
N-((4-methoxyphenyl)sulfonyl)glycinate (71)

In a 4 mL screw cap vial 4-methoxy-N-(4-(4-methoxyphenethyl)naphthalen-1-yl)benzenesulfonamide (70) (30 mg, 0.067 mmol), potassium carbonate (11.1 mg, 0.08 mmol) and acetonitrile (0.5 mL) was added followed by the addition of ethyl bromoacetate (9 μL, 0.08). The reaction was stirred at room temperature overnight. The reaction was diluted with ethylacetate (2 mL) and filtered through a small pad of celite, washing with ethyl acetate. The filtrate was concentrated to an orange oil and purified by column chromatography (silica gel; ethyl acetate/Hexanes, 0:100 to 40:60) to yield the title compound.

Example 31. Synthesis of N-(4-(4-methoxyphenethyl)naphthalen-1-yl)-N-((4-methoxyphenyl)sulfonyl)glycine

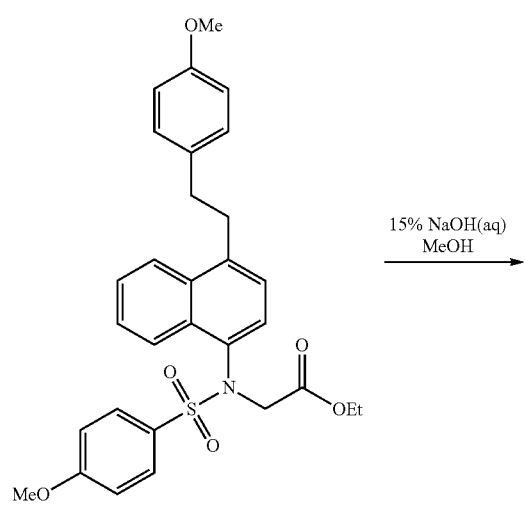

15% NaOH(aq)
MeOH
→

110
-continued

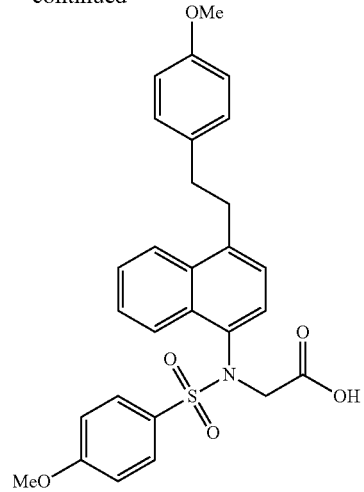

N-(4-(4-methoxyphenethyl)naphthalen-1-yl)-N-((4-methoxyphenyl)sulfonyl)glycine (72)

In a 20 mL screw cap vial ethyl N-(4-(4-methoxyphenethyl)naphthalen-1-yl)-N-((4-methoxyphenyl)sulfonyl) glycinate (71) (35 mg, 0.066 mmol) was dissolved in MeOH (3 mL) and 15% NaOH$_{(aq)}$ (0.5 mL) was added. The reaction was stirred at room temperature for 4 hours. Once the reaction was complete by TLC methanol was removed under reduced pressure. The residual suspension was diluted with water (10 mL) and acidified with 2 N HCl$_{(aq)}$ to pH 2. The resulting suspension was extracted with EtOAc (3×10 mL), combined organics were washed with brine (20 mL) and dried over Na$_2$SO$_4$. Solvent was removed under reduced pressure to afford an off white solid. Compound was purified by preparative HPLC (C18; MeCN/H$_2$O+0.1% FA, 60:40 to 95:5) to yield the title compound.

ASPECTS OF THE DISCLOSURE

1. In one aspect the disclosure provides a compound, or pharmaceutically acceptable salt thereof, having the structure of Formula (I):

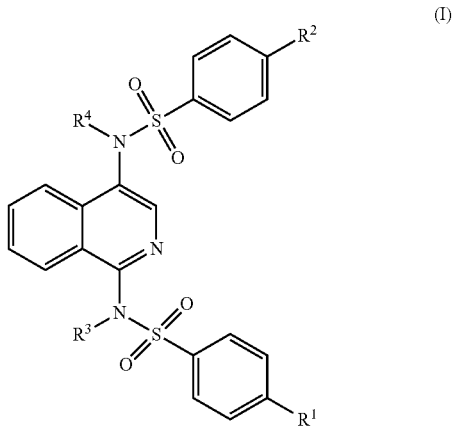

(I)

wherein
each of $R^1$ and $R^2$ independently is halo, OH, CN, $C_{1-6}$haloalkyl, $C_{1-6}$alkoxy, $C_{1-6}$haloalkoxy, or C(O)$R^6$;

each of $R^3$ and $R^4$ independently is H, $C_{1-6}$alkyl, deuterated $C_{1-6}$alkyl, $C_{1-6}$haloalkyl, $C_{1-6}$alkylene-CN, $C_{0-6}$alkylene-$C_{1-5}$heteroaryl having 1, 2, 3, or 4 heteroatoms selected from N, O, and S, $C_{0-6}$alkylene-C(O)$R^6$, $C_{0-6}$alkylene-N($R^5$)SO$_2$$R^7$, $C_{0-6}$alkylene-C(O)N($R^5$)SO$_2$$R^7$, $C_{0-6}$alkylene-C(O)NHOH, or $C_{0-6}$alkylene-C=N(OH)N($R^5$)$_2$;

each $R^5$ independently is H or $C_{1-6}$alkyl;

$R^6$ is OH, $C_{1-6}$haloalkyl, or $C_{1-6}$alkoxy; and $R^7$ is $C_{1-6}$alkyl or N($R^5$)$_2$.

2. The compound or salt of aspect 1, wherein at least one of $R^1$ and $R^2$ is halo.

3. The compound or salt of aspect 2, wherein each of $R^1$ and $R^2$ is halo.

4. The compound or salt of aspect 2 or 3, wherein halo is F or Cl,

5. The compound or salt of any one of aspects 1 to 3, wherein halo is F.

6. The compound or salt of aspect 1, wherein at least one of $R^1$ and $R^2$ is OH.

7. The compound or salt of aspect 6, wherein each of $R^1$ and $R^2$ is OH.

8. The compound or salt of aspect 1, wherein at least one of $R^1$ and $R^2$ is CN.

9. The compound or salt of aspect 8, wherein each of $R^1$ and $R^2$ is CN.

10. The compound or salt of aspect 1, wherein at least one of $R^1$ and $R^2$ is $C_{1-6}$alkoxy.

11. The compound or salt of aspect 10, wherein each of $R^1$ and $R^2$ is $C_{1-6}$alkoxy.

12. The compound or salt of aspect 10 or 11, wherein $C_{1-6}$alkoxy is OCH$_3$.

13. The compound or salt of aspect 1, wherein at least one of $R^1$ and $R^2$ is COOH or C(O)$C_{1-6}$alkoxy.

14. The compound or salt of aspect 13, wherein each of $R^1$ and $R^2$ is COOH.

15. The compound or salt of aspect 1, wherein at least one of $R^1$ and $R^2$ independently is $C_{1-6}$haloalkyl, $C_{1-6}$haloalkoxy, or C(O)$C_{1-6}$haloalkyl.

16. The compound or salt of aspect 15, wherein each of $R^1$ and $R^2$ independently is $C_{1-6}$ haloalkyl, $C_{1-6}$haloalkoxy, or C(O)$C_{1-6}$haloalkyl.

17. The compound or salt of aspect 15 or 16, wherein is $C_{1-6}$haloalkyl is CF$_3$, $C_{1-6}$ haloalkoxy is OCF$_3$, and C(O)$C_{1-6}$haloalkyl is C(O)CF$_3$.

18. The compound or salt of aspect 1, wherein each of $R^1$ and $R^2$ independently is OCH$_3$, F, Cl, CN, CF$_3$, OCF$_3$, or C(O)CF$_3$.

19. The compound or salt of aspect 18, wherein each of $R^1$ and $R^2$ independently is OCH$_3$ or F.

20. The compound or salt of any aspects 1 to 19, wherein at least one of $R^3$ and $R^4$ is H.

21. The compound or salt of any one of aspects 1 to 19, wherein at least one of $R^3$ and $R^4$ is $C_{1-6}$alkyl or deuterated $C_{1-6}$alkyl.

22. The compound or salt of aspect 21, wherein at least one of $R^3$ and $R^4$ is CH$_3$ or CD$_3$.

23. The compound or salt of any one of aspect 1 to 19, wherein at least one of $R^3$ and $R^4$ is $C_{0-6}$alkylene-C(O)$R^6$.

24. The compound or salt of aspect 23, wherein $R^3$ is CH$_2$COOH or CH(CH$_3$)COOH.

25. The compound or salt of aspect 24, wherein $R^3$ is CH$_2$COOH.

26. The compound or salt of aspect 23, wherein $R^4$ is CH$_2$C(O)CF$_3$.

27. The compound or salt of any one of aspects 1 to 19, wherein at least one of $R^3$ and $R^4$ is $C_{1-6}$haloalkyl or $C_{1-6}$alkylene-CN.

28. The compound or salt of aspect 27, wherein $R^4$ is $C_{1-6}$haloalkyl or $C_{1-6}$alkylene-CN.

29. The compound or salt of aspect 27 or 28, wherein $C_{1-6}$haloalkyl is CF$_3$, CH$_2$CF$_3$, CF$_2$CH$_3$, CH$_2$CF$_2$H, CH$_2$CFH$_2$, or CH$_2$CH$_2$CF$_3$ and $C_{1-6}$alkylene-CN is CH$_2$CN.

30. The compound or salt of aspect 29, wherein $R^4$ is CH$_2$CF$_3$.

31. The compound or salt of any one of aspect 1 to 19, wherein at least one of $R^3$ and $R^4$ is $C_{0-6}$alkylene-$C_{1-5}$ heteroaryl having 1, 2, 3, or 4 heteroatoms selected from N, O, and S.

32. The compound of aspect 31, wherein at least one of $R^3$ and $R^4$ is tetrazolyl, oxadiazolonyl, thiadiazolonyl, oxathadiazolyl oxide, or oxadiazolthionyl.

33. The compound or salt of aspect 32, wherein at least one of $R^3$ and $R^4$ is

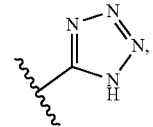

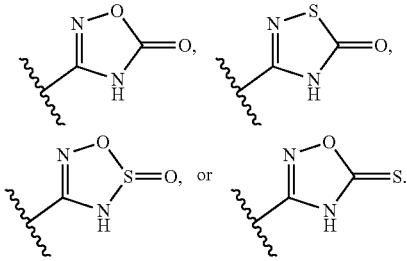

34. The compound or salt of aspect 33, wherein $R^3$ is

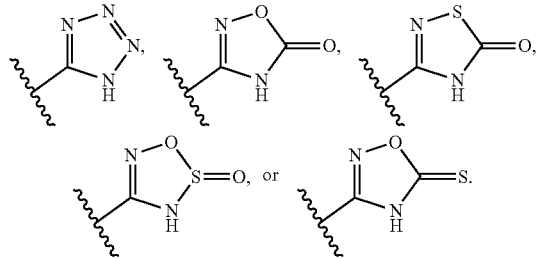

35. The compound of any one of aspects 1 to 19, wherein at least one of $R^3$ and $R^4$ is $C_{0-6}$alkylene-N($R^5$)SO$_2$$R^7$, $C_{0-6}$alkylene-C(O)N($R^5$)SO$_2$$R^7$, $C_{0-6}$alkylene-C(O)NHOH, or $C_{0-6}$alkylene-C=N(OH)N($R^5$)$_2$.

36. The compound or salt of aspect 35, wherein each $R^5$ independently is H or CH$_3$ 37. The compound or salt of aspect 35 or 36, wherein $R^7$ is CH$_3$ or N(CH$_3$)$_2$.

38. The compound or salt of any one of aspects 35 to 37, wherein $R^3$ is CH$_2$C(O)NHOH, CH$_2$C(O)NHSO$_2$CH$_3$, CH₂C(O)NHSO₂N(CH₃)₂, CH₂CH₂NHSO₂CH₃, CH₂CH₂NHSO₂N(CH₃)₂, or CH₂C=N(OH)NH₂.

39. The compound or salt of any one of aspects 1 to 19, wherein R³ is CH₂COOH, CH(CH₃)COOH,

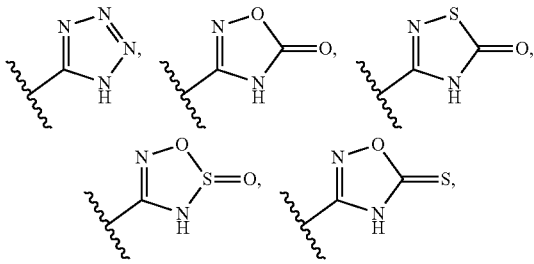

CH₂C(O)NHOH, CH₂C(O)NHSO₂CH₃, CH₂C(O)NHSO₂N(CH₃)₂, CH₂CH₂NHSO₂CH₃, CH₂CH₂NHSO₂N(CH₃)₂, or CH₂C=N(OH)NH₂.

40. The compound or salt of aspect 39, wherein R³ is CH₂COOH
41. The compound or salt of aspect 39 or 40, wherein R⁴ is CF₃, CH₂CF₃, CF₂CH₃, CH₂CF₂H, CH₂CFH₂, CH₂CH₂CF₃, or CH₂CN.
42. The compound or salt of any one of aspects 39 to 41, wherein R⁴ is CH₂C(O)CF₃.
43. The compound or salt of any one of aspects 1 to 19, wherein R³ is CH₂COOH and R⁴ is CH₂CF₃.
44. The compound or salt of aspect 1, wherein:
   each of R¹ and R² independently is halo, OH, CN, C₁₋₆haloalkyl, C₁₋₆alkoxy, C₁₋₆haloalkoxy, or C(O)C₁₋₆haloalkyl;
   R³ is C₀₋₆alkylene-COOH, C₀₋₆alkylene-C(O)C₁₋₆alkoxy, C₀₋₆alkylene-C₁₋₅heteroaryl having 1, 2, 3, or 4 heteroatoms selected from N, O, and S, C₀₋₆alkylene-N(R⁵)SO₂R⁷, C₀₋₆alkylene-C(O)N(R⁵)SO₂R⁷, C₀₋₆alkylene-C(O)NHOH, or C₀₋₆alkylene-C=N(OH)N(R⁵)₂;
   R⁴ is H, C₁₋₆haloalkyl, C₁₋₆alkylene-CN, or C₀₋₆alkylene-C(O)C₁₋₆haloalkyl;
   each R⁵ independently is H or C₁₋₆alkyl; and
   R⁷ is C₁₋₆alkyl or N(R⁵)₂.
45. The compound or salt of aspect 44, wherein:
   each of R¹ and R² independently is OCH₃, F, Cl, CN, CF₃, OCF₃, or C(O)CF₃; R³ is CH₂COOH, CH(CH₃)COOH,

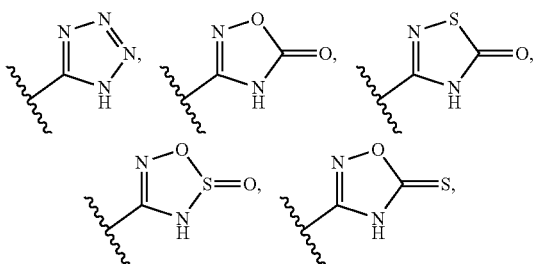

CH₂C(O)NHOH, CH₂C(O)NHSO₂CH₃, CH₂C(O)NHSO₂N(CH₃)₂, CH₂CH₂NHSO₂CH₃, CH₂CH₂NHSO₂N(CH₃)₂, or CH₂C=N(OH)NH₂; and
R⁴ is H, CF₃, CH₂CF₃, CF₂CH₃, CH₂CF₂H, CH₂CFH₂, CH₂CH₂CF₃, or CH₂CN.

46. The compound or salt of aspect 45, wherein:
   each of R¹ and R² independently is OCH₃ or F;
   R³ is CH₂COOH; and
   R⁴ is H or CH₂CF₃.
47. The compound of aspect 1, having a structure as recited in Table A, or a pharmaceutically acceptable salt thereof.
48. The compound of aspect 1, Having a structure as recited in Table B, or a pharmaceutically acceptable salt thereof.
49. The compound of aspect 47 or 48 having a structure selected from the group consisting of,

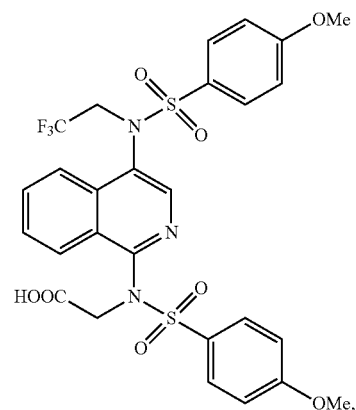

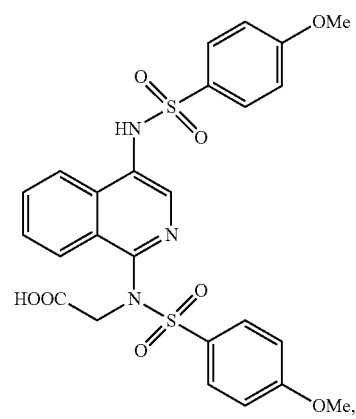

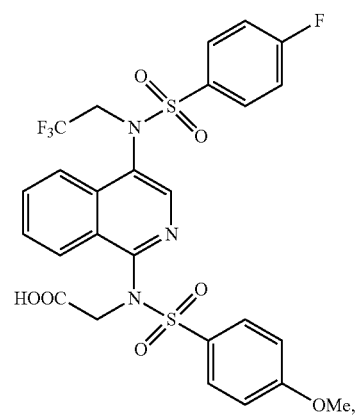

-continued

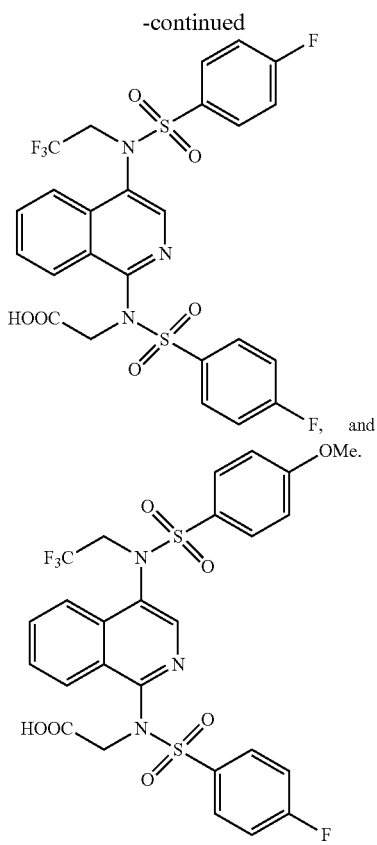

or pharmaceutically acceptable salts thereof.

50. The compound of aspect 49 having a structure

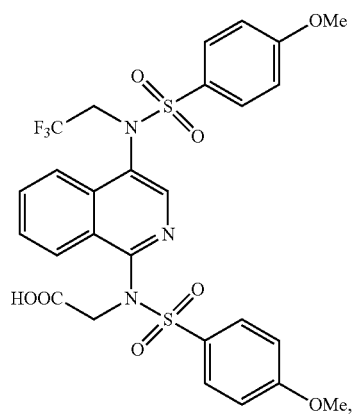 [SMILES: COc1ccc(S(=O)(=O)N(CC(F)(F)F)c2cnc(N(CC(=O)O)S(=O)(=O)c3ccc(OC)cc3)c3ccccc23)cc1]

or a pharmaceutically acceptable salt thereof.

51. A pharmaceutical composition comprising the compound or salt of any one of aspects 1 to 50 and a pharmaceutically acceptable carrier.

52. A method of inhibiting the KEAP-1/NRF2 interaction in a cell comprising contacting the cell with the compound or salt of any one of aspects 1 to 50 or the pharmaceutical composition of aspect 51 in an amount effective to inhibit the KEAP-1/NRF2 interaction.

53. A method of treating a clinical or preclinical disease or disorder associated with dysregulation of the KEAP1-NRF2 interaction comprising administering to a subject in need thereof a therapeutically effective amount of the compound or salt of any one of aspects 1 to 50 or the pharmaceutical composition of aspect 51.

54. The method of aspect 53, wherein the clinical disease or disorder is selected from the group consisting of Alport syndrome, amyotrophic lateral sclerosis, autosomal dominant polycystic kidney disease, bone disease, blood disease, chronic kidney disease, chronic obstructive pulmonary disease, connective tissue disease, dry eye macular degeneration, estrogen receptor-positive breast cancer, eye disease, focal segmental glomerulosclerosis, Friedreich ataxia, immunoglobulin A nephropathy, interstitial lung disease, lung diseases, multiple sclerosis, kidney disease, neurodegenerative disease, primary focal segmental glomerulosclerosis, psoriasis, pulmonary arterial hypertension, retinovascular disease, subarachnoid hemorrhage, type 1 diabetes, and type 2 diabetes mellitus.

55. The method of aspect 53, wherein the preclinical disease or disorder is selected from the group consisting of, autoimmune disease, respiratory disease, gastrointestinal disease, metabolic disease, cardiovascular disease, neurodegenerative disease, skin disease, and cancer chemoprevention.

56. A method of accelerating wound healing comprising administering to a subject in need thereof a therapeutically effective amount of the compound or salt of any one of aspects 1 to 50 or the pharmaceutical composition of aspect 51.

57. The method of aspect 56, wherein the wound is a chronic wound or a diabetic wound.

58. The method of aspect 57, wherein the chronic wound is a venous ulcer or a pressure sore.

59. The method of aspect 57, wherein the diabetic wound is a diabetic foot ulcer.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:

1. A compound, or pharmaceutically acceptable salt thereof, having the structure of Formula I:

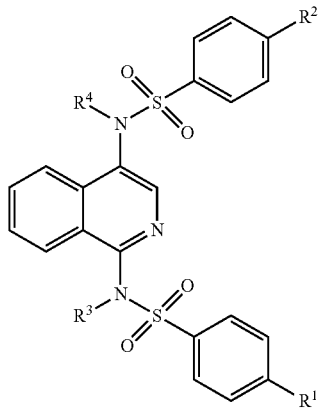

wherein
each of $R^1$ and $R^2$ independently is halo, OH, CN, $C_{1-6}$haloalkyl, $C_{1-6}$alkoxy, $C_{1-6}$haloalkoxy, or $C(O)R^6$;
each of $R^3$ and $R^4$ independently is H, $C_{1-6}$alkyl, deuterated $C_{1-6}$alkyl, $C_{1-6}$haloalkyl, $C_{1-6}$alkylene-CN, $C_{0-6}$alkylene-$C_{1-5}$heteroaryl having 1, 2, 3, or 4 heteroatoms selected from N, O, and S, $C_{0-6}$alkylene-C(O)$R^6$, $C_{0-6}$alkylene-N($R^5$)SO$_2R^7$, $C_{0-6}$alkylene-C(O)N($R^5$)SO$_2R^7$, $C_{0-6}$alkylene-C(O)NHOH, or $C_{0-6}$alkylene-C=N(OH)N($R^5$)$_2$;
each $R^5$ independently is H or $C_{1-6}$alkyl;
$R^6$ is OH, $C_{1-6}$haloalkyl, or $C_{1-6}$alkoxy; and
$R^7$ is $C_{1-6}$alkyl or N($R^5$)$_2$.

2. The compound or salt of claim 1, wherein each of $R^1$ and $R^2$ independently is Cl, F, $C_{1-3}$haloalkyl, $C_{1-3}$alkoxy, $C_{1-3}$haloalkoxy, or C(O)$C_{1-3}$alkoxy.

3. The compound or salt of claim 1, wherein each of $R^1$ and $R^2$ independently is OCH$_3$, F, Cl, CN, CF$_3$, OCF$_3$, or C(O)CF$_3$.

4. The compound or salt of claim 3, wherein each of $R^1$ and $R^2$ independently is OCH$_3$ or F.

5. The compound or salt of claim 1, wherein:
$R^3$ is $C_{0-6}$alkylene-COOH, $C_{0-6}$alkylene-C(O)$C_{1-6}$alkoxy, $C_{0-6}$alkylene-$C_{1-5}$heteroaryl having 1, 2, 3, or 4 heteroatoms selected from N, O, and S, $C_{0-6}$alkylene-N($R^5$)SO$_2R^7$, $C_{1-6}$alkylene-C(O)N($R^5$)SO$_2R^7$, $C_{0-6}$alkylene-C(O)NHOH, or $C_{0-6}$alkylene-C=N(OH)N($R^5$)$_2$;
each $R^5$ independently is H or $C_{1-6}$alkyl; and
$R^7$ is $C_{1-6}$alkyl or N($R^5$)$_2$.

6. The compound or salt of claim 5 wherein $R^3$ is CH$_2$COOH, CH(CH$_3$)COOH,

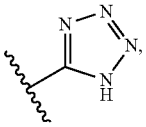 , 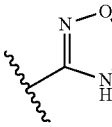 , 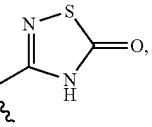 ,

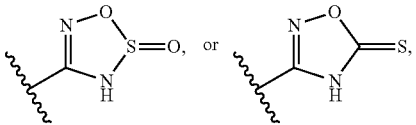

CH$_2$C(O)NHOH, CH$_2$C(O)NHSO$_2$CH$_3$, CH$_2$C(O)NHSO$_2$N(CH$_3$)$_2$, CH$_2$CH$_2$NHSO$_2$CH$_3$, CH$_2$CH$_2$NHSO$_2$N(CH$_3$)$_2$, or CH$_2$C=N(OH)NH$_2$.

7. The compound or salt of claim 6, wherein $R^3$ is CH$_2$COOH.

8. The compound or salt of claim 1, wherein $R^4$ is H, $C_{1-6}$haloalkyl, $C_{1-6}$alkylene-CN, or $C_{0-6}$alkylene-C(O)$C_{1-6}$haloalkyl.

9. The compound or salt of claim 8, wherein $R^4$ is H, CF$_3$, CH$_2$CF$_3$, CF$_2$CH$_3$, CH$_2$CF$_2$H, CH$_2$CFH$_2$, CH$_2$CH$_2$CF$_3$, CH$_2$CN, or CH$_2$C(O)CF$_3$.

10. The compound or salt of claim 9, wherein $R^4$ is CH$_2$CF$_3$.

11. The compound of claim 1 having a structure selected from the group consisting of

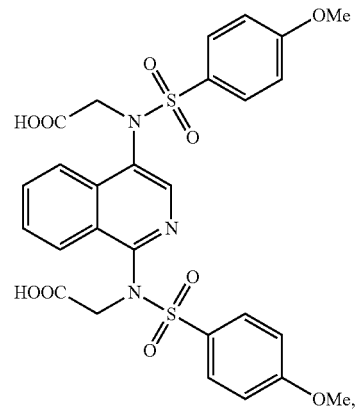

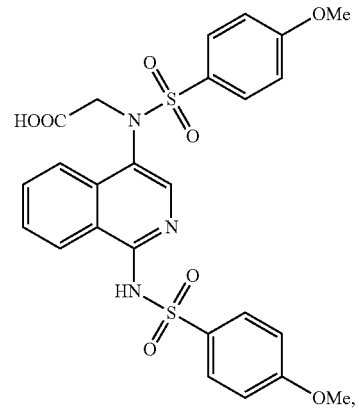

-continued

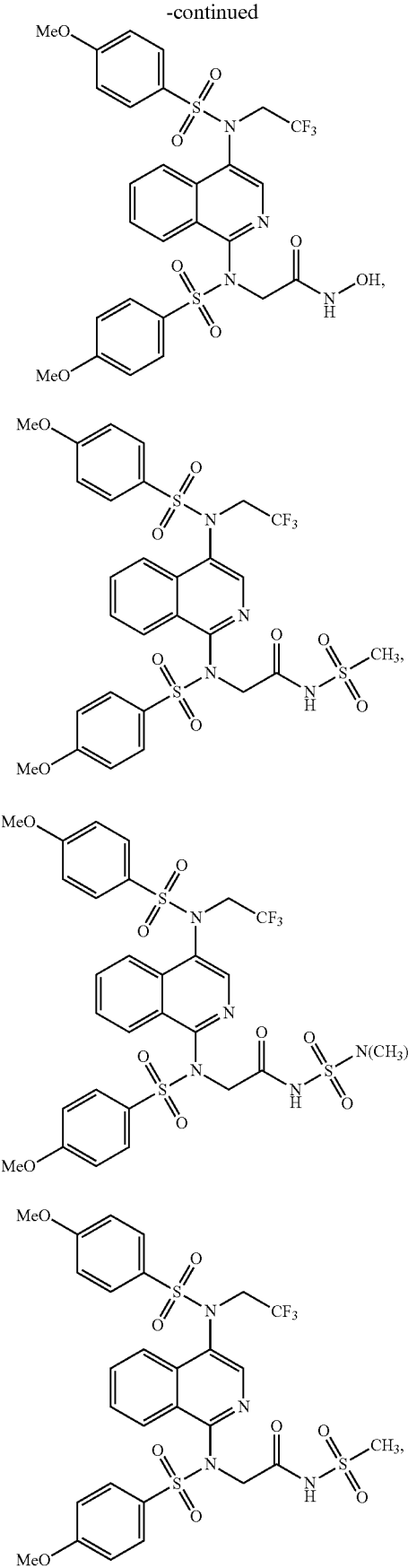
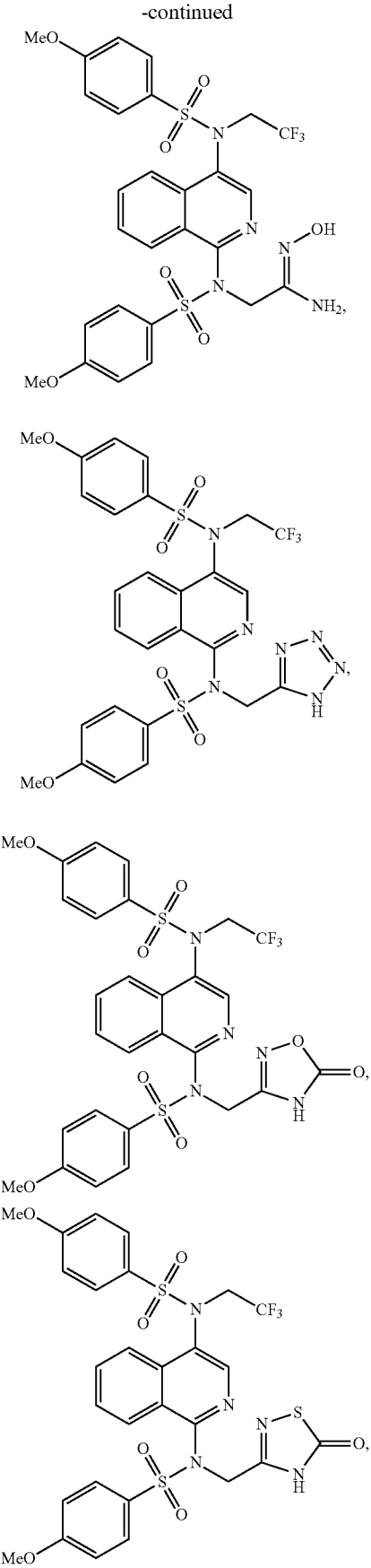

123
-continued
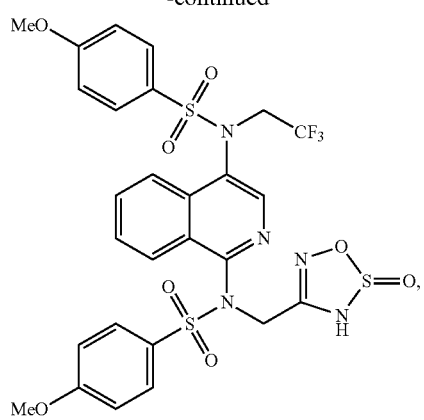
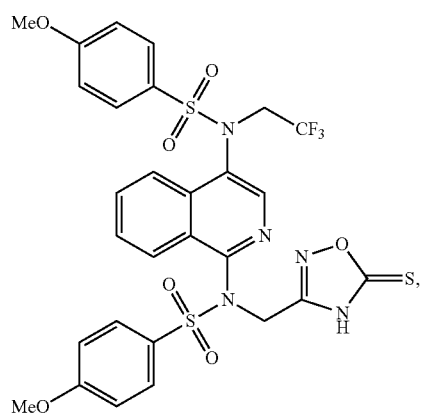
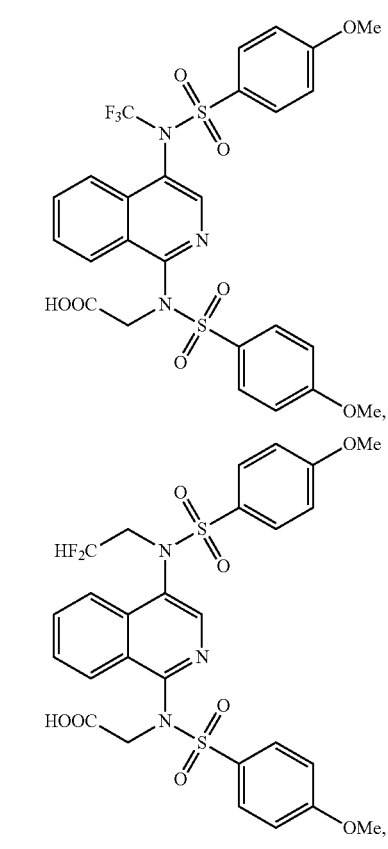
124
-continued
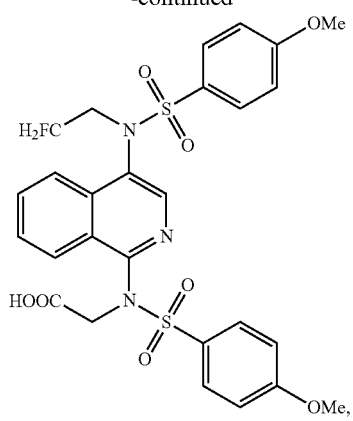
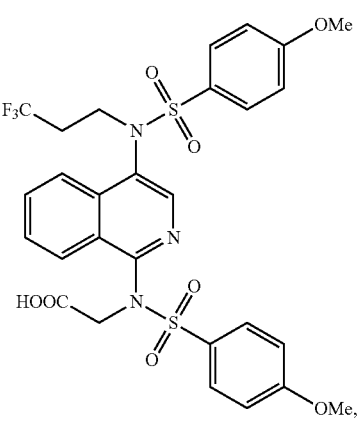
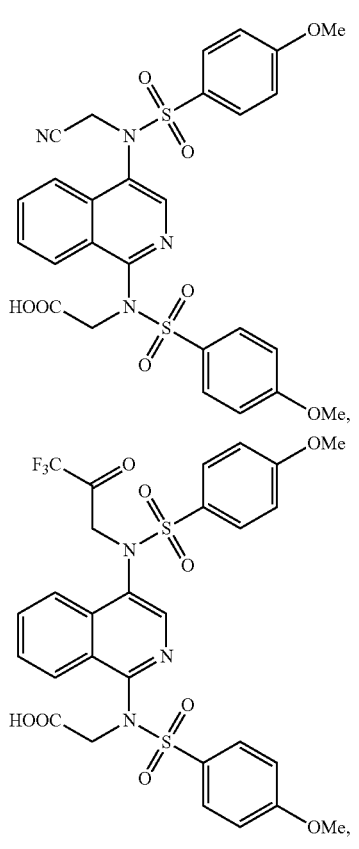
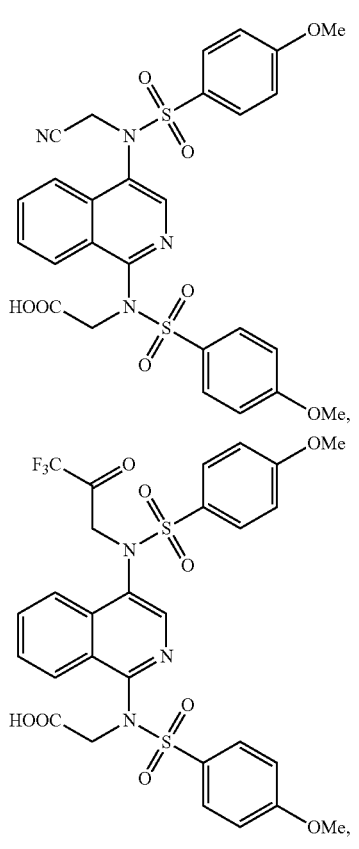
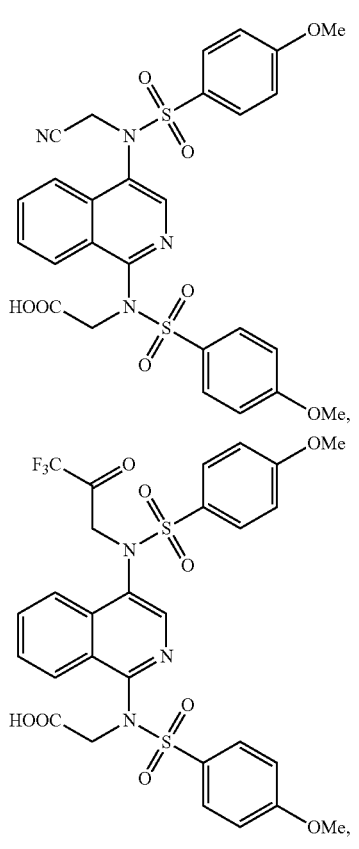

-continued
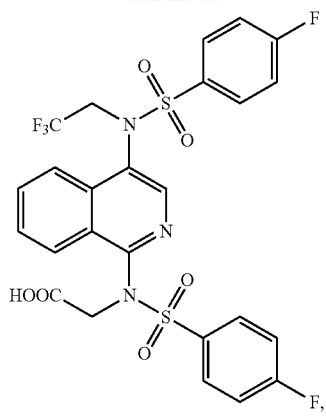
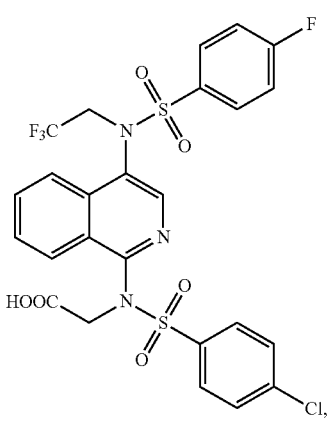
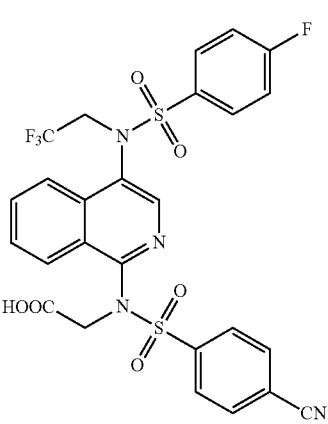
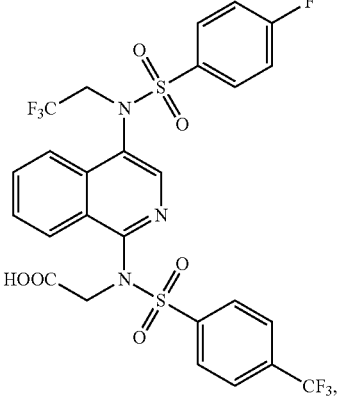
-continued
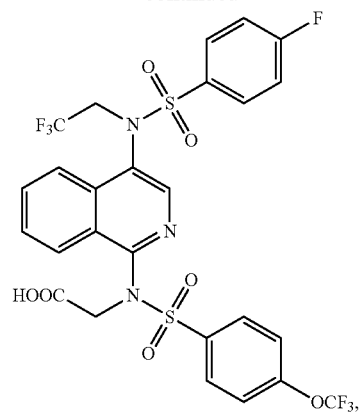
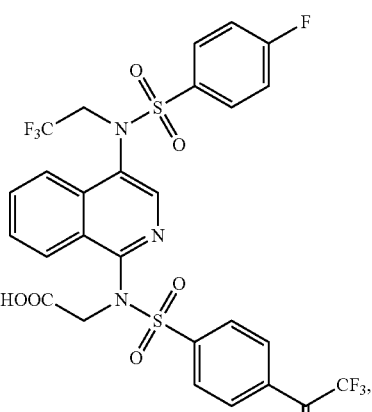
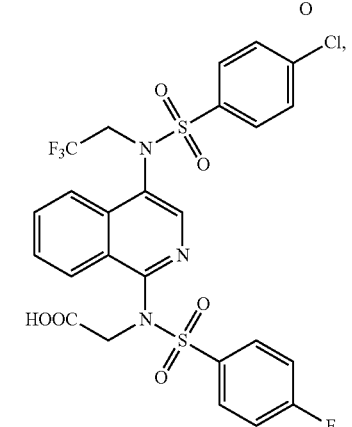
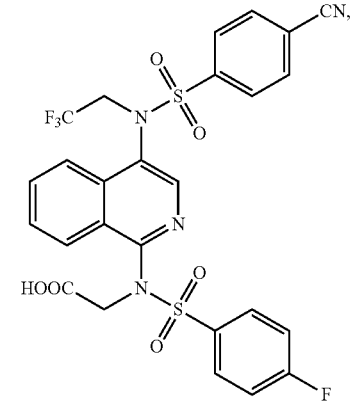

127
-continued
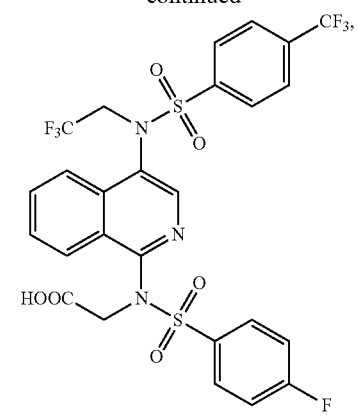
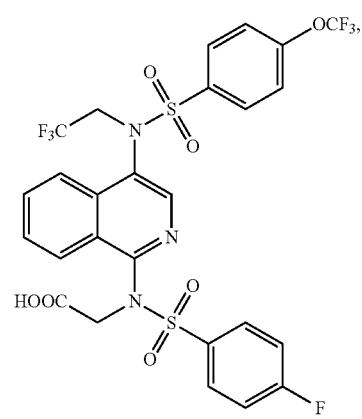
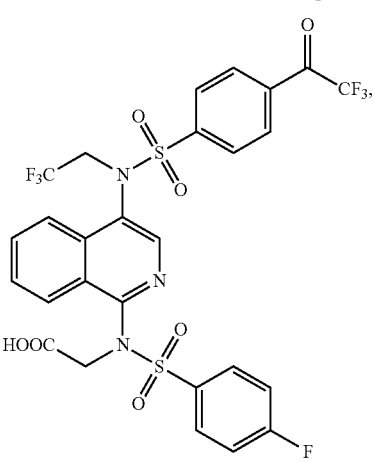
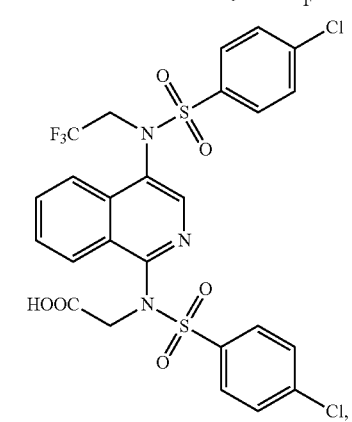
128
-continued
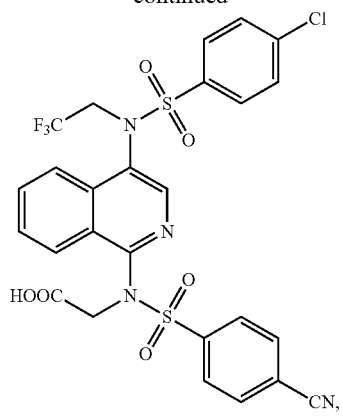
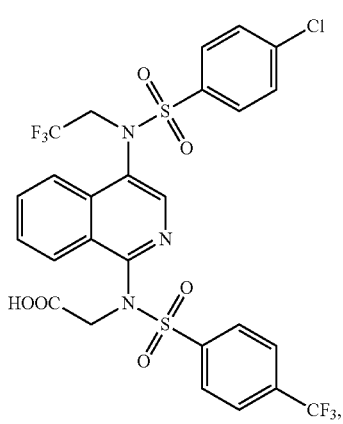
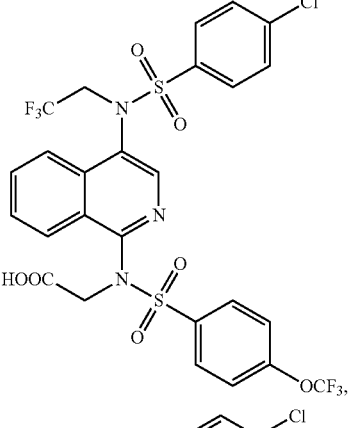
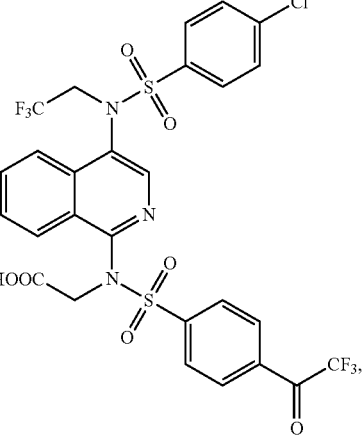

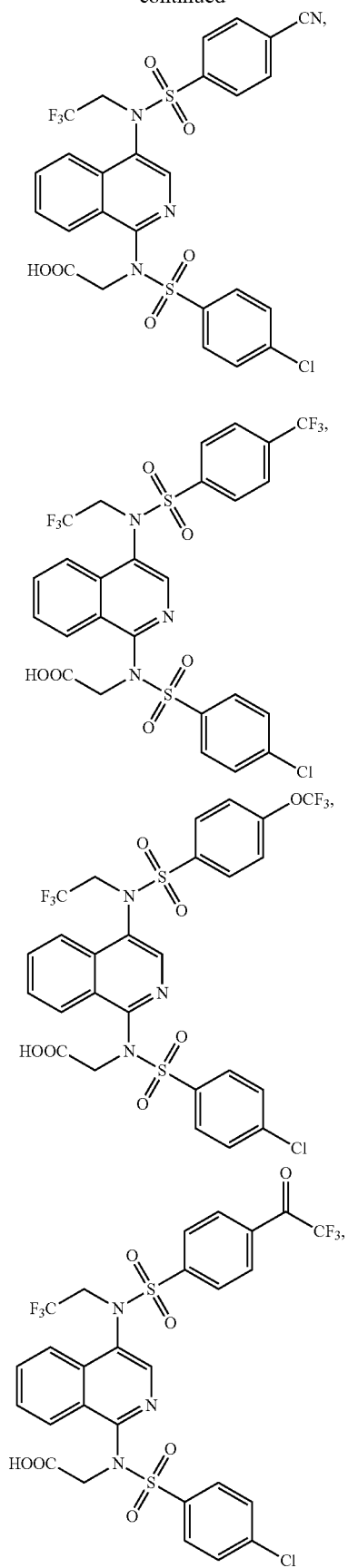
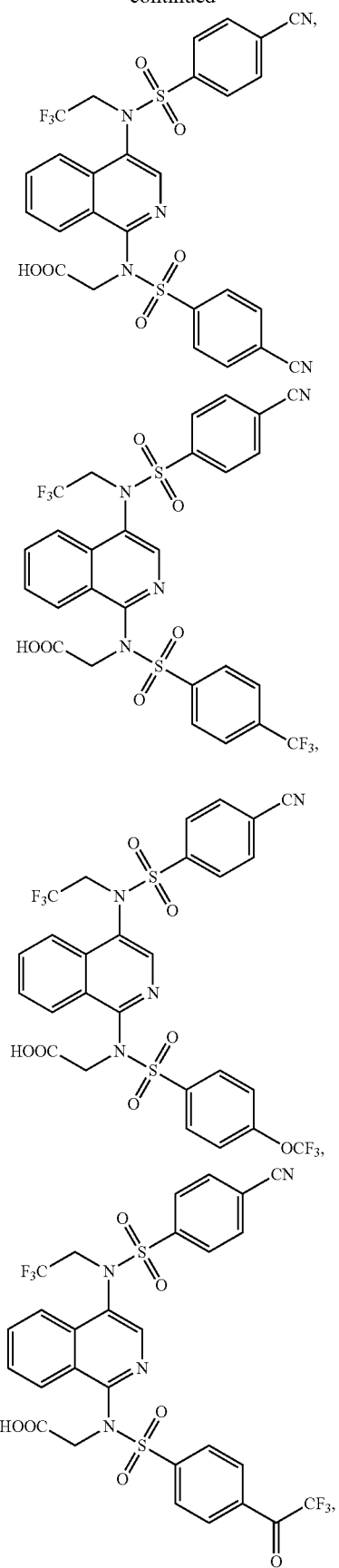

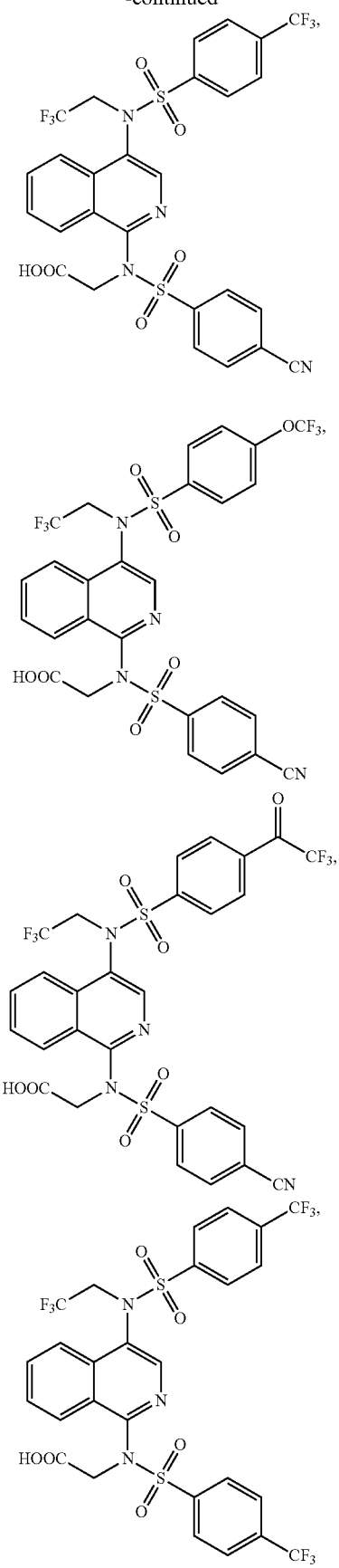
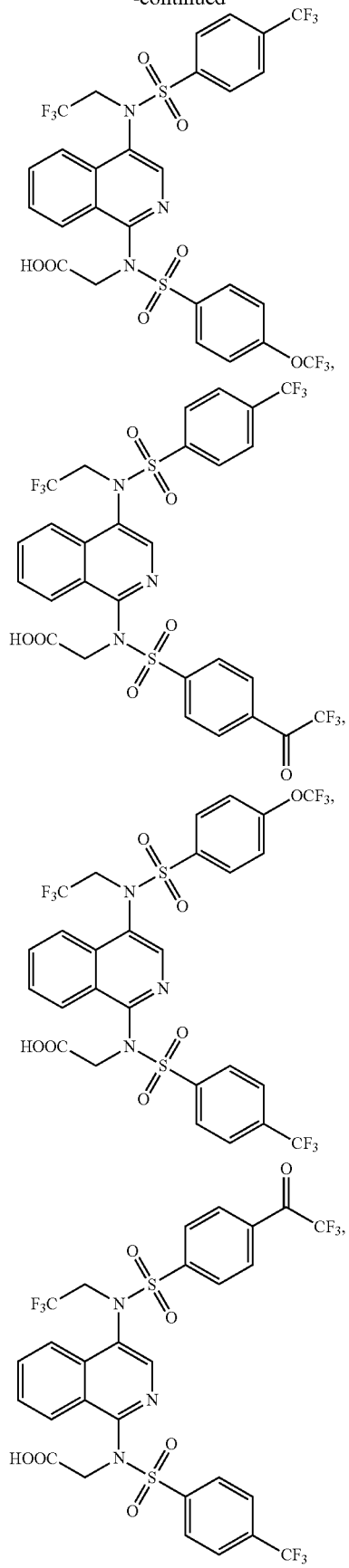

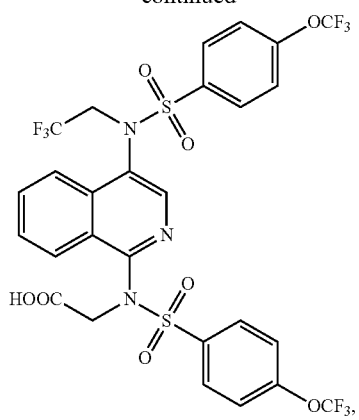
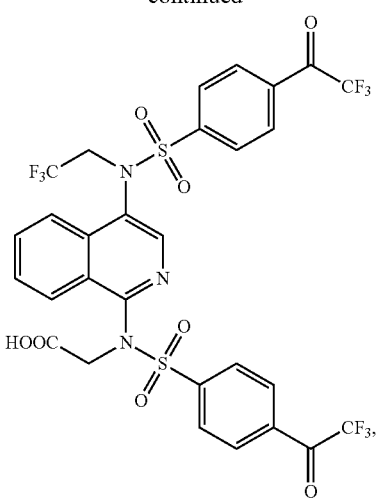
or a pharmaceutically acceptable salt thereof.
12. The compound of claim 11, having a structure selected from the group consisting of:
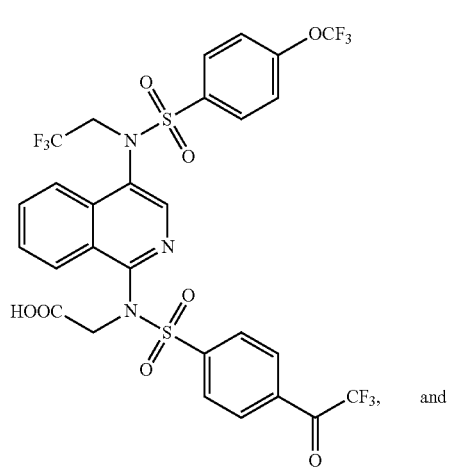 and
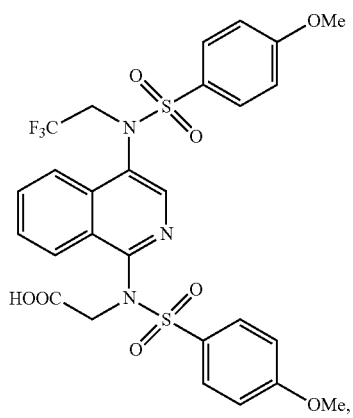
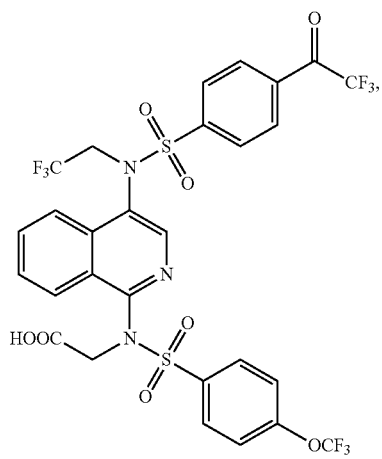
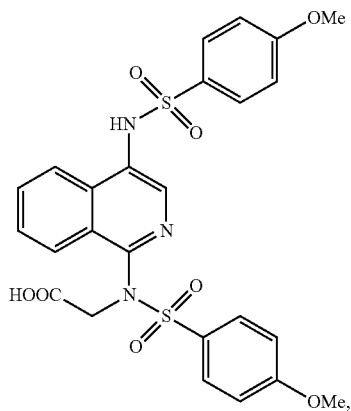

-continued

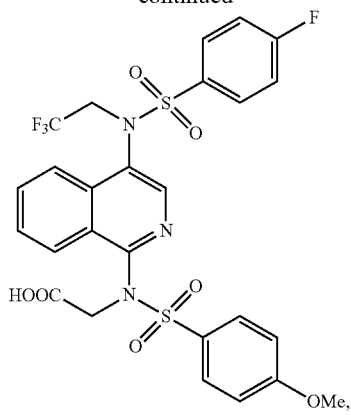

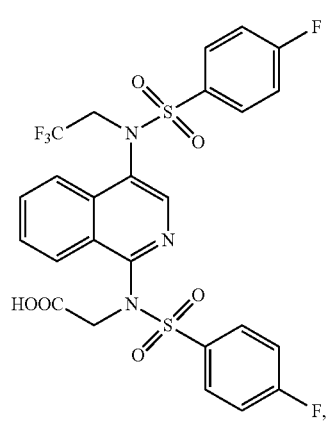

-continued

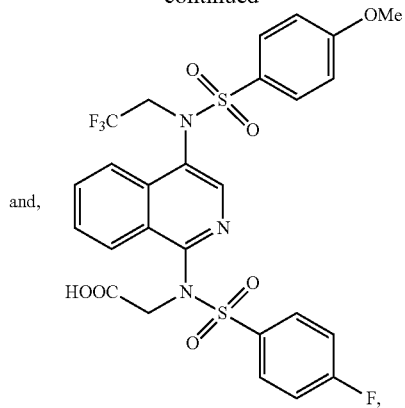

and,

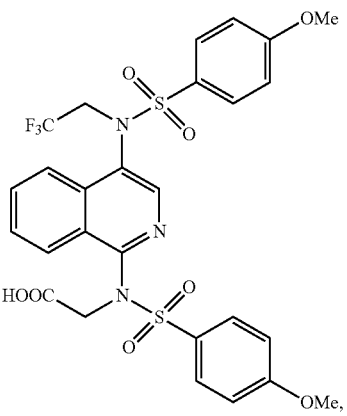

or a pharmaceutically acceptable salts thereof.

13. The compound of claim 12, having a structure

[structure]

or a pharmaceutically acceptable salt thereof.

14. A pharmaceutical composition comprising the compound or salt of claim 1 and a pharmaceutically acceptable carrier.

15. A method of inhibiting the KEAP-1/NRF2 interaction in a cell comprising contacting the cell with the compound or salt of claim 1, in an amount effective to inhibit the KEAP-1/NRF2 interaction.

* * * * *